US007410986B2

(12) United States Patent
Murata et al.

(10) Patent No.: US 7,410,986 B2
(45) Date of Patent: Aug. 12, 2008

(54) 4-6-DIPHENYL PYRIDINE DERIVATIVES AS ANTIINFLAMMATORY AGENTS

(75) Inventors: Toshiki Murata, Ikoma (JP); Sachiko Sasaki, Ikoma (JP); Takashi Yoshino, Nara (JP); Yuka Ikegami, Kyoto-fu (JP); Tsutomu Masuda, Nara (JP); Mitsuyuki Shimada, Nara (JP); Takuya Shintani, Kyoto-fu (JP); Makoto Shimazaki, Kyoto-fu (JP); Timothy B. Lowinger, Wuppertal (DE); Karl B. Ziegelbauer, Haan (DE); Kinji Fuchikami, Kyoto-fu (JP); Masaomi Umeda, Nara (JP); Hiroshi Komura, Nara (JP); Nagahiro Yoshida, Kyoto-fu (JP)

(73) Assignee: Bayer Aktiengesellschaft, Leverkusen (DE)

( * ) Notice: Subject to any disclaimer, the term of this patent is extended or adjusted under 35 U.S.C. 154(b) by 648 days.

(21) Appl. No.: 10/433,377

(22) PCT Filed: Nov. 19, 2001

(86) PCT No.: PCT/EP01/13338

§ 371 (c)(1),
(2), (4) Date: Nov. 3, 2003

(87) PCT Pub. No.: WO02/44153

PCT Pub. Date: Jun. 6, 2002

(65) Prior Publication Data

US 2004/0097563 A1    May 20, 2004

(30) Foreign Application Priority Data

Dec. 1, 2000   (JP) .............................. 2000-366708

(51) Int. Cl.
*A61K 31/4412*   (2006.01)
*A61K 31/4418*   (2006.01)
*C07D 213/61*   (2006.01)
*C07D 213/62*   (2006.01)

(52) U.S. Cl. ...................... 514/352; 546/290; 546/304; 514/344; 514/345

(58) Field of Classification Search ................. 546/304; 514/352
See application file for complete search history.

(56) References Cited

FOREIGN PATENT DOCUMENTS

WO         0224651       3/2002
WO    WO 02/24651 A1 *  3/2002

OTHER PUBLICATIONS

CAPLUS Accession No. 1927:3281, abstract of Dilthey et al, "Pyrylium compounds. XVII. Arylated pyridines," Journal fuer Praktische Chemie (Leipsig), 1926, vol. 114, pp. 153-178.*

Database Chemcats Online!, Chem, Abstract Service, retrived from STN: XP002197384 and "Ambinter: Screening Collection," 2001.*
Database Chemcats Online!, Chem, Abstract Service, retrived from STN: XP002197385 and "AsInEx Compound Collection," 2001.*
Database Chemcats Online!, Chem, Abstract Service, retrived from STN: XP002197386 and "Chem.Folio."*
Ankhiwala, M.D., "Synthesis and Biological Studies of Some 2-Amino-3-Cyano-4-Aryl-6-(2'-Hydroxy-4'-N-Butoxy-5'-H/Nitrophenyl)pyridines," J. Ind. Chem. Soc. 69(3), pp. 166-167 (1992).*
Manna, F. et al, "Anti-inflammatory, Analgesis, and Antipyretic 4,6-disubstituted 3-cyano-2-aminopyridines," Eur. J. Med. Chem., vol. 34, pp. 245-254 (1999).*
Database Chemcats 'Online!, Chemical Abstracts Service, Columbus, Ohio, US, retrieved from STN; XP002197384 & "Ambinter: Screening Collection", May 31, 2001, Ambinter, 75016 Paris, France.
Database Chemcats 'Online!, Chemical Abstracts Service, Columbus, Ohio, US, retrieved from STN; XP002197385 & "AsInEx Compound Collection", May 10, 2001, Asinex, 123182 Moscow, Russia.
Database Chemcats 'Online!, Chemical Abstracts Service, Columbus, Ohio, US, retrieved from STN; XP002197386, order No. TRG08000#09403-D; TRG08000#13126-D; TRG08000#13131-D; TRG08000#13124-D; TRG08000#01963-D; TRG08000#00603-D; TRG08000#13135-D; TRG08000#13121-D; TRG08000#13122-D & "Chem.Folio", Lion BioScience AG, 69027 Heidelberg, Germany.
Ankhiwala, M. D.; "Synthesis and Biological Studies of Some 2-Amino-3-Cyano-4-Aryl-6-(2'-Hydroxy-4'-N-Butoxy-5'-H/Nitrophenyl)pyridines", J. Indian Chem. Soc., 69(3): 166-167 (1992).
Kumar, N., Singh, G., and Yadav, A. K., "Synthesis of some 2-thioxopyrido [2,3-*d*]pyrimidine ribofuranosides and their antimicrobial activity", Phosphorus, Sulfur and Silicon, 175: 217-225 (2001).
Manna, F., Chimenti, F., Bolasco, A. Filippelli, A., Palla, A., Filippelli, W., Lampa, E. and Mercantini, R., "Anti-inflammatory, Analgesic and Antipyretic 4,6-Disubstituted 3-Cyanopyridine-2-ones and 3-Cyano-2-Aminopyridines", Eur. J. Med. Chem., 27: 627-632 (1992).

(Continued)

*Primary Examiner*—Kamal Saeed
*Assistant Examiner*—Janet L Coppins
(74) *Attorney, Agent, or Firm*—Edwards Angell Palmer & Dodge LLP; Barry Kramer; Ralph A. Loren

(57) ABSTRACT

4-aryl pyrimidine compounds of general formula and salts thereof: wherein X is CH or N; R1 is hydrogen, halogen, C1-6 alkyl, C1-6 alkoxy, etc.; R2 is hydrogen or hydroxy; R3 is hydrogen, C1-6 alkyl, etc.; R4 is hydrogen, hydroxy, halogen, amino, etc.; R5 is hydroxy, amino, carboxy, etc.; R6 is hydrogen, carbamoyl, cyano, carboxy, C1-6 alkoxycarbonyl, etc. and R7 is amino or C1-6 alkanoylamino. The compounds (I) or the salts thereof have an excellent anti-inflammatory activity and the like.

9 Claims, No Drawings

OTHER PUBLICATIONS

Manna, F., Chimenti, F., Bolasco, A., Bizzarri, B., Filippelli, W., Filippelli, A., and Gagliardi, L., "Anti-inflammatory, Analgesic and Antipyretic 4,6-Disubstituted 3-Cyano-2-Aminopyridines", Eur. J. Med. Chem., 34: 245-254 (1999).

Lewis, A. J. and Manning, A. M., "New Targets for Anti-Inflammatory Drugs", Current Opinion in Chemical Biology, 3: 489-494 (1999).

* cited by examiner

4-6-DIPHENYL PYRIDINE DERIVATIVES AS ANTIINFLAMMATORY AGENTS

DETAILED DESCRIPTION OF INVENTION

1. Technical Field

The present invention relates to novel 4-aryl pyridine derivatives, processes for preparing them and pharmaceutical preparations containing them. The 4-aryl pyridine derivatives of the present invention inhibit IκB kinase β (IKK-β or IKK-beta) activity, thus inhibit nuclear factor kappa B (NF-κB) activity, and can be used for the prophylaxis and treatment of diseases associated with NF-κB activity, in particular for the treatment of inflammatory diseases.

2. Background Art

Nuclear factor kappa B (NF-κB) belongs to a family of closely related homo- and hetero-dimeric transcription factor complexes composed of various combinations of the Rel/NF-κB family of polypeptides. NF-κB and related family members are involved in the regulation of more than 50 genes relating to immune and inflammatory responses ((Barnes P J, Karin M (1997) N Engl J Med 336, 1066-1071) and (Baeuerle P A, Baichwal V R (1997) Adv Immunol 65, 111-137)). In most cell types, NF-κB is present as a heterodimer comprising a 50 kDa and a 65 kDa subunit (p50/RelA). The heterodimer is sequestered in the cytoplasm in association with inhibitor of NF-κB (IκB)-family of proteins to be kept in an inactive state. IκB-family proteins mask the nuclear translocation signal of NF-κB. Upon stimulation of cells with various cytokines. (e.g. TNF-α, IL-1), CD40 ligand, lipopolysaccharide (LPS), oxidants, mitogens (e.g. phorbol ester), viruses or many others. IκB proteins are phosphorylated at specific serine residues, poly-ubiquitinated, and then degraded through a proteasome-dependent pathway. Freed from IκB, the active NF-κB is able to translocate to the nucleus where it binds in a selective manner to preferred gene-specific enhancer sequences. Among the genes being regulated by NF-κB are many coding for pro-inflammatory mediators, cytokines, cell adhesion molecules, and acute phase proteins. Expression of several of these cytokines and mediators in turn can lead to further activation of NF-κB via autocrine and paracrine mechanisms.

Broad evidence is available that suggests a central role of NF-κB in many inflammatory disorders including airway inflammation and asthma ((Yang L et al., J Exp Med 188 (1998), 1739-1750), (Hart L A et al. Am J Respir Crit Care Med 158 (1998), 1585-1592), (Stacey M A et al., Biochem Biophys Res Commun 236 (1997), 522-526) (Barnes P and Adcock I M, Trends Pharmacol Sci 18 (1997), 46-50)).

Further, it has been shown that glucocorticoids, which are by far the most effective treatment for asthma, inhibit airway inflammation by directly interacting with and inhibiting the activity of the transcription factors NF-κB and activating peptide-1 (AP-1) ((Barnes P (1997) Pulmon Pharmacol Therapeut 10, 3-19) and (Dumont A et al. (1998) Trends Biochem Sci 23, 233-235)).

In general, inhibition of NF-κB activation results in strong anti-inflammatory effects similar or superior to those brought upon by steroids. Consequently, NF-κB inhibition should improve inflammatory symptoms typical for asthma; allergic rhinitis; atopic dermatitis; hives; conjunctivitis; vernal catarrh; rheumatoid arthritis; systemic lupus erythematosus; psoriasis; diabrotic colitis; systemic inflammatory response syndrome; sepsis; polymyositis; dermatomyositis; Polyaritis nodoa; mixed connective tissue disease; Sjoegren's syndrome; gout, and the like.

Further, several studies imply that NF-κB plays an essential role in neoplastic transformation. For example, NF-κB is associated with cell transformation in vitro and in vivo as a result of gene overexpression, amplification, rearrangement, or translocation (Mercurio, F., and Manning, A. M. (1999) Oncogene, 18:6163-6171). In certain human lymphoid tumor cells, the genes of NF-κB family members are rearranged or amplified. Its possible involvement in cancer pathology is also disclosed in Mayo, M. W., Baldwin A. S. (2000) Biochmica et Biophysica Acta 1470 M55-M62. Mayo M. W. et al., discloses the inhibition of NF-κB results in the blockage the initiation and/or progression of certain cancer, particularly colorectal cancer.

Finally, NF-κB may also be involved in the regulation of neuronal cell death. It has been shown that NF-κB becomes activated and promotes cell death in focal cerebral ischemia (Nature medicine Vol. 5 No. 5, May 1999).

Extensive research during the past years led to the identification of an IκB kinase (IKK) complex as being responsible for the signal-induced IκB phosphorylation (Hatada, E. N, et al. (2000) Current Opinion in Immunology, 12:52-58)). This complex is most likely the site of integration of all of the different stimuli leading to NF-κB activation. The IKK-complex (molecular weight 700-900 kDa) is composed of various proteins including two homologous IκB kinases, called IKK-α and IKK-β, an upstream kinase, NIK which induces NF-κB, a scaffold protein called IKAP, which tethers together the three kinases, and a regulatory subunit IKK-γ, which preferentially interacts with IKK-β.

IKK-β is a 756 amino acid serine-threonine kinase showing 52% identity to and the same domain structure as IKK-α ((Mercurio F et al. (1997) Science 278, 860-866. ), (Woronicz J D et al. (1997) Science 278, 866-869. ), (Zandi E et al. (1997) Cell 91, 243-252. ). IKK-β forms homo-dimers and hetero-dimers with IKK-α in vitro and in cells, respectively. IKK-β also interacts with IKK-γ, IKAP, NIK and IκBα. Recombinant IKK-β phosphorylates IκBα and IκBβ at specific serine residues with equal efficacy (Li J et al. (1998) J Biol Chem 273, 30736-30741). IKK-β shows a higher constitutive kinase activity as compared to IKK-α. This is in agreement with data suggesting that over-expression of IKK-β activates the transcription of a NF-κB-dependent reporter gene with a higher efficacy as compared to IKK-α. IKK-β has been shown to be activated in various cell lines or fresh human cells in response to various stimuli including TNF-α, IL-1β, LPS, anti-CD3/anti-CD28 co-stimulation, protein kinase C and calcineurin, B-cell receptor/CD40 ligand stimulation, and vanadate. IKK-β is activated in fibroblast-like synoviocytes (FLS) isolated from the synovium of patients suffering from rheumatoid arthritis or osteoarthritis (Kempiak S J et al. (1999) J Immunol 162, 3176-3187. ). Furthermore, IKK-β can be activated by the structurally related upstream kinases MEKK-1 and NIK, most likely through phosphorylation of specific serine residues within the T-loop (activation loop) and by certain protein kinase C isoforms (Lallena M J et al. (1999) Mol Cell Biol 19, 2180-2188.). A catalytically inactive mutant of IKK-β has been shown to inhibit activation of NF-κB by TNF-α, IL-1β, LPS, anti-CD3/anti-CD28 stimulation (Woronicz J D et al. (1997) Science 278, 866-869). The same effects are observed when MEKK1 or NIK are overexpressed. Additionally, IKK-β mutations in the activation loop inhibited IL-1 and TNF-α signaling (Delhase M et al. (1999) Science 284, 309-313. ). Based on the experimental results described above, there is clear-cut evidence for a pivotal involvement of IKK-β in various pathways leading to NF-κB activation.

In summary, the specific inhibition of IKK-β should result in a strong anti-inflammatory and immuno-modulatory effect in vivo with the potential of improving the underlying causes of asthma and other diseases. In addition, anti-tumor and anti-ischemic effects of an IKK-inhibitor may be expected.

Manna et al., disclose 4,6-disubstituted 3-cyano-2-aminopyridines represented by general formulas:

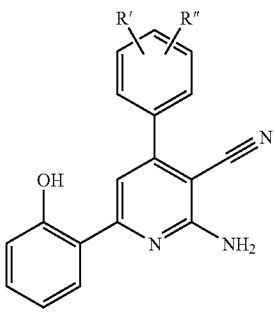

wherein
(R', R'') represent (OCH$_3$, OCH$_3$), (Cl, Cl), (H, Cl), (H, Br), (H, CH$_3$), (H, OCH$_3$), (H, NO$_2$), or (H, N(CH$_3$)$_2$),
and

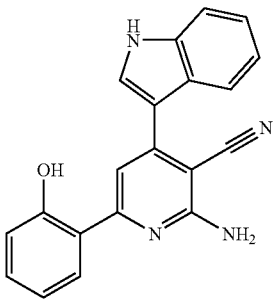

as a general anti-inflammatory, analgesic, and antipyretic agent (Eur J. Med. Chem. 34, 245-254(1999)).

However, the development of a novel compound having effective anti-inflammatory actions based on a specific and selective inhibitory activity to NF-κB has been still desired.

SUMMARY OF THE INVENTION

As a result of extensive studies on chemical modification of pyridine derivatives, the present inventors have found that the compounds of novel chemical structure related to the present invention have unexpectedly excellent NF-κB inhibitory activity based on IKK-β inhibition and cytokine inhibition. The present invention has been accomplished based on these findings.

This invention is to provide a novel 4-aryl pyridine derivatives shown by the following formula (I) and salts thereof.

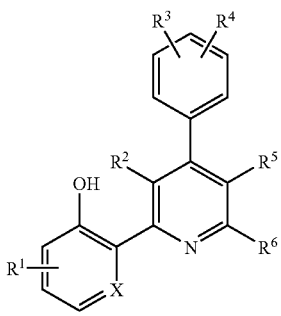

(I)

wherein
X is CH or N;
R$^1$ is hydrogen, hydroxy, halogen, C$_{1-6}$ alkyl, C$_{1-6}$ alkoxy, C$_{1-6}$ alkoxycarbonyl, nitro, amino, mono or di (C$_{1-6}$ alkyl) amino, phenylsulfonylamino, —NHR$^{11}$ or —O—(CH$_2$)$_n$—R$^{12}$,
wherein
R$^{11}$ is phenyl substituted C$_{1-6}$ alkyl, C$_{1-6}$ alkanoyl or C$_{1-6}$alkylsulfonyl,
n represents an integer selected from 0 to 6, and
R$^{12}$ is C$_{2-6}$ alkenyl, benzoyl, mono or di phenyl, mono or di (C$_{1-6}$ alkyl)amino, C$_{1-6}$ alkanoyl, C$_{1-6}$ alkoxycarbonyl, or a 3 to 10 membered saturated or unsaturated ring having 0 to 3 heteroatoms selected from the group consisting of S, O and N, and said ring is optionally substituted by hydroxy, nitro, cyano, mono or di halogen, C$_{1-6}$ alkyl, halogen substituted C$_{1-6}$ alkyl, amino, mono or di (C$_{1-6}$ alkyl)amino, C$_{1-6}$ alkanoylamino, carbamoyl, C$_{1-6}$ alkoxy, C$_{1-6}$ alkoxycarbonyl, or phenyl;
R$^2$ is hydrogen, hydroxy, halogen, or C$_{1-6}$ alkyl;
R$^3$ is hydrogen, hydroxy, halogen, C$_{1-6}$ alkoxy, C$_{3-6}$ cycloalkyl substituted C$_{1-6}$alkyloxy, —NR$^{31}$R$^{32}$, or a 3 to 6 membered saturated ring having 0 to 3 heteroatoms selected from the group consisting of O and N, and said ring is optionally substituted by R$^{33}$;
Wherein
R$^{31}$ is hydrogen or C$_{1-6}$ alkyl
R$^{32}$ is hydrogen, C$_{1-6}$ alkanoyl, or C$_{1-6}$ alkyl optionally substituted by hydroxy or phenyl,
R$^{33}$ is nitro, cyano, C$_{1-6}$ alkyl optionally substituted by hydroxy or amino, C$_{1-6}$ alkoxy, hydroxy substituted C$_{1-6}$ alkyloxy, amino substituted C$_{1-6}$ alkyloxy, C$_{1-6}$ alkanoyl, carbamoyl or —NR$^{33a}$R$^{33b}$
Wherein
R$^{33a}$ is hydrogen or C$_{1-6}$ alkyl
R$^{33b}$ is hydrogen, C$_{1-6}$ alkyl optionally substituted by hydroxy or phenyl, C$_{1-6}$ alkanoyl, C$_{1-6}$ alkylsulfonyl, or trifluoroacetyl,
R$^4$ is hydrogen, hydroxy, carboxy, —CO—NHR$^{41}$, amino, C$_{1-6}$ alkylsulfonylamino, or —NH—COR$^{41}$, C$_{1-6}$ alkyl optionally substituted by R$^{42}$, C$_{1-6}$ alkoxy, R$^{43}$C$_{1-6}$ alkyloxy,
wherein
R$^{41}$ is C$_{1-6}$ alkyl optionally substituted by R$^{41a}$, C$_{1-6}$ alkoxy, oxotetrahydrofuryl, oxopyrrolidinyl, —CH(OH)R$^{41b}$, —CH(NH$_2$)R$^{41c}$, —NHR$^{41c}$, or piperazino optionally substituted by R$^{41d}$,
wherein
R$^{41a}$ is carboxy, C$_{1-6}$ alkoxy, —CH(NH$_2$)carboxy, —NR$^{41a-1}$R$^{41a-2}$, or a 3 to 10 membered saturated ring having 0 to 3 heteroatoms selected from the group consisting of O and N, and said ring is optionally substituted by carboxy, C$_{1-6}$ alkyl optionally substituted by hydroxy or benzodioxane, C$_{3-6}$ cycloalkyl, C$_{1-6}$ alkanoyl, carboxy, benzyl, C$_{1-6}$ alkoxycarbonyl, or furoyl,
wherein
R$^{41a-1}$ is hydrogen or C$_{1-6}$ alkyl optionally substituted by hydroxy, C$_{1-6}$ alkyloxy, C$_{3-8}$ cycloalkyl, or piperidino,
R$^{41a-2}$ is hydrogen or C$_{1-6}$ alkyl optionally substituted by hydroxy, C$_{1-6}$ alkyloxy or C$_{3-6}$ cycloalkyl, C$_{1-6}$ alkoxy or a 3 to 6 membered saturated ring having 0 to 3 heteroatoms selected from the group consisting of O and N, and said ring is optionally substituted by carboxy, C$_{1-6}$ alkyl, C$_{1-6}$ alkanoyl, or C$_{1-6}$ alkyloxy,
R$^{41b}$ is C$_{1-6}$ alkyl optionally substituted by carboxy or C$_{1-6}$ alkyloxy, C$_{1-6}$ alkoxy, or C$_{1-6}$ alkoxycarbonyl, $R^{41c}$ is carboxy, $C_{1-6}$ alkyl optionally substituted by carboxy or a 3 to 6 membered saturated ring having 0 to 3 heteroatoms selected from the group consisting of O and N, or $R^{41d}$ is $C_{1-6}$ alkyl optionally substituted by carboxy or $C_{1-6}$ alkyloxy, or $C_{1-6}$ alkoxy $R^{42}$ is $C_{1-6}$ alkoxy, carboxy, amino, —CH(NH$_2$)-carboxy or a 5 to 7 membered saturated or unsaturated ring having 0 to 3 heteroatoms selected from the group consisting of O and N, and said ring is optionally substituted by hydroxy, nitro, mono or di halogen, $C_{1-6}$ alkyl, halogen substituted $C_{1-6}$ alkyl, amino, mono or di ($C_{1-6}$ alkyl) amino, or carbamoyl;

$R^{43}$ is carboxy, amino, —CH(NH$_2$)-carboxy or a 5 to 7 membered saturated or unsaturated ring having 0 to 3 heteroatoms selected from the group consisting of O and N, and said ring is optionally substituted by hydroxy, nitro, mono or di halogen, $C_{1-6}$ alkyl, halogen substituted $C_{1-6}$ alkyl, amino, mono or di ($C_{1-6}$ alkyl)amino, or carbamoyl;

or $R^3$ and $R^4$ may form, together with the carbon atoms in the benzene ring, a 4 to 6 membered saturated ring having 0 to 3 heteroatoms selected from the group consisting of O and N, and said ring is optionally substituted by one or more substituents selected from the group consisting of hydroxy, nitro, mono or di halogen, $C_{1-6}$ alkyl, halogen substituted $C_{1-6}$ alkyl, oxo, amino, mono or di ($C_{1-6}$ alkyl)amino, and carbamoyl;

$R^5$ is hydrogen, cyano, carboxy, carbamoyl, $C_{1-6}$ alkyl optionally substituted by hydroxy or carbamoyl, and $C_{1-6}$ alkoxycarbonyl, and $R^6$ is —NR$^{61}$R$^{62}$, wherein $R^{61}$ is hydrogen or $C_{1-6}$ alkyl, $R^{62}$ is hydrogen, $C_{1-6}$ alkyl, phenyl, benzyl, $C_{1-6}$ alkanoyl, or NR$^{61}$R$^{62}$ may form, together with the nitrogen atom to which they are attached, a saturated 5-6 membered ring optionally containing NH or O as other heteroatoms than the adjacent N atom or $R^5$ and $R^6$ may form, together with the carbon atoms in the pyridine ring, a 5 to 7 membered saturated or unsaturated ring having 0 to 3 heteroatoms selected from the group consisting of O, S and N, and said ring optionally having substituents selected from the group consisting of halogen, nitro, cyano, oxo, thioxo, $C_{1-6}$ alkyl, $C_{1-6}$ alkylsulfonyl, $C_{1-6}$ alkoxy, $C_{1-6}$ alkoxycarbonyl, phenyl, $C_{1-6}$ alkanoyl, amino, $C_{1-6}$ alkylamino, $C_{1-6}$ alkanoylamino, carbamoyl, $C_{3-8}$ cycloalkylaminocarbonyl, $C_{1-6}$ alkylaminocarbonyl, halogen substituted $C_{1-6}$ alkylaminocarbonyl, di ($C_{1-6}$ alkyl)aminocarbonyl, benzoylamino, phenylsulfonyl, di($C_{1-6}$alkyl)amino$C_{1-6}$ alkylaminocarbonyl, hydroindenylaminocarbonyl, diphenylmethylaminocarbonyl, pyrrolidinocarbonyl, $C_{1-6}$ alkyloxy $C_{1-6}$ alkyl amino carbonyl, morpholinocarbonyl, piperazinocarbonyl, phenyl$C_{1-6}$ alkylaminocarbonyl, carboxy$C_{1-6}$alkylaminocarbonyl, $C_{3-8}$ cycloalkyl$C_{1-6}$alkylaminocarbonyl, hydroxy$C_{1-6}$alkylaminocarbonyl, and methylsulfonylaminocarbonyl or a salt thereof.

The compounds of the present invention surprisingly show excellent IKK-β kinase inhibitory activity and cytokine inhibitory activity. They are, therefore suitable especially as NF-κB inhibitors and in particular for the production of pharmaceuticals or pharmaceutical compositions, which may be useful to treat NF-κB dependent diseases.

More specifically, since the 4-aryl pyridine derivatives of the present invention inhibit IKK-β kinase activity, they are useful for treatment and prophylaxis of diseases involving NF-κB activity as follows: inflammatory symptoms including asthma; allergic rhinitis; atopic dermatitis; hives; conjunctivitis; vernal catarrh; chronic arthrorheumatism; systemic lupus erythematosus; psoriasis; diabrotic colitis; systemic inflammatory response syndrome (SIRS); sepsis; polymyositis; dermatomyositis (DM); polyarthritis nodosa (PN); mixed connective tissue disease (MCTD); Sjoegren's syndrome; gout; and the like.

The compounds of the present invention are also useful for treatment and prophylaxis of diseases like ischemia and tumor, since the diseases also relate to IKK-β kinase and NF-κB activity.

Preferred compounds of the formula (I) are those wherein:

X is CH or N;

$R^1$ is hydrogen, halogen, $C_{1-6}$ alkoxy, or cyclopropyl methoxy;

$R^2$ is hydrogen;

$R^3$ is hydrogen, hydroxy, halogen, amino, mono or di($C_{1-6}$ alkyl)amino, acetamido, $C_{1-6}$alkoxy, cyclopropyl methoxy, $C_{1-6}$ alkyl(hydroxy substituted $C_{1-6}$ alkyl)amino, $C_{1-6}$ alkyl(benzyl)amino, morpholino, piperidino, or pyrrolidino optionally substituted by $C_{1-6}$ alkyl, hydroxy substituted $C_{1-6}$ alkyl, amino, di ($C_{1-6}$ alkyl)amino, or trifluoroacetylamino;

$R^4$ is hydrogen, hydroxy, carboxy, amino, $C_{1-6}$ alkylsulfonylamino, piperazino, $C_{1-6}$ alkyl substituted piperazino, piperidino substituted $C_{1-6}$ alkyloxy, piperidino $C_{1-6}$ alkylaminocarbonyl, or —NH—COR$^{41}$, wherein $R^{41}$ is $C_{1-6}$ alkyl optionally substituted by $R^{41a}$, $C_{1-6}$ alkoxy, oxotetrahydrofuryl, oxopyrrolidinyl, —CH(OH)R$^{41b}$, or —CH(NH$_2$)R$^{41c}$, wherein $R^{41a}$ is $C_{1-6}$ alkoxy, carboxy, —CH(NH$_2$)-carboxy, —NHR$^{41a-1}$ (wherein R$^{41a-1}$ is hydrogen, $C_{1-6}$ alkyl optionally substituted by hydroxy, $C_{3-8}$ cycloalkyl, $C_{1-6}$ alkoxy, or piperidino), —N($C_{1-6}$ alkyl)R$^{41a-2}$ (wherein R$^{41a-2}$ is $C_{1-6}$ alkyl or $C_{1-6}$ alkyl substituted pyrrolidinyl), pyrrolidinyl, piperidino optionally substituted by carboxy or $C_{1-6}$ alkoxycarbonyl, piperidino fused with cyclohexane, or piperazino optionally substituted by $C_{1-6}$ alkyl, hydroxy substituted $C_{1-6}$ alkyl, benzodioxane substituted $C_{1-6}$ alkyl, benzyl, $C_{1-6}$ alkanoyl, cyclohexyl, or furoyl, $R^{41b}$ is $C_{1-6}$ alkyl optionally substituted by carboxy or $C_{1-6}$ alkoxycarbonyl, $R^{41c}$ is $C_{1-6}$ alkyl optionally substituted by carboxy, or $R^3$ and $R^4$ may form —NR$^{401}$—CO—O-(wherein R$^{401}$ is hydrogen or $C_{1-6}$ alkyl);

$R^5$ is hydrogen, carbamoyl, cyano, carboxy, or hydroxymethyl; and $R^6$ is amino or acetamido or $R^5$ and $R^6$ may form —R$^{50}$—CH$_2$—NH—, —R$^{50}$—CO—NH—, —R$^{50}$—SO$_2$—NH—, or —R$^{50}$—C(=S)—NH— wherein $R^{50}$ is —CHR$^{501}$—O—, —CH$_2$—N R$^{501}$—, —CO—NR$^{501}$—, (wherein R$^{501}$ is hydrogen, $C_{1-6}$ alkyl, $C_{1-6}$ alkanoyl, $C_{1-6}$ alkoxycarbonyl, carbamoyl, $C_{1-6}$ alkylsulfonyl, $C_{3-8}$ cycloalkylaminocarbonyl, $C_{1-6}$ alkylaminocarbonyl, di ($C_{1-6}$ alkyl)aminocarbonyl or phenyl)

or a salt thereof.

In the context of the present invention, the substituents, if not stated otherwise, in general have the following meaning:

$C_{1-6}$ alkyl in general represents a straight-chain or branched hydrocarbon radical having 1 to 6 carbon atoms. Non-limiting examples include methyl, ethyl, propyl, isopropyl, butyl, isobutyl, pentyl, isopentyl, hexyl, isohexyl.

$C_{1-6}$ alkoxy in general represents a straight-chain or branched hydrocarbon radical having 1 to 6 carbon atoms and bound via an oxygen atom. Non-limiting examples include methoxy, ethoxy, propoxy, isopropoxy, butoxy, isobutoxy, pentoxy, isopentoxy, hexoxy, isohexoxy.

$C_{3-8}$ cycloalkyl in general represents a cyclic hydrocarbon radical having 3 to 8 carbon atoms. Cyclopropyl, cyclopentyl and cyclohexyl are preferred. Non-limiting examples include cyclopentyl, cyclohexyl, cycloheptyl and cyclooctyl.

$C_{2-6}$ alkenyl stands for straight-chain or branched residues containing one or more double bonds, e.g. vinyl, allyl.

The preferable compounds of the present invention are as follows:

5-({3-[2-amino-3-cyano-6-(2-hydroxyphenyl)-4-pyridinyl]phenyl}amino)-4-hydroxy-5-oxopentanoate;
N-{3-[2-amino-3-cyano-6-(2-hydroxyphenyl)-4-pyridinyl]phenyl}-5-oxotetrahydro-2-furancarboxamide;
N-{3-[2-amino-3-cyano-6-(2-hydroxyphenyl)-4-pyridinyl]phenyl}methanesulfonamide;
$N^4$-{3-[2-amino-3-cyano-6-(2-hydroxyphenyl)-4-pyridinyl]phenyl}-L-asparagine;
$N^1$-{3-[2-amino-3-cyano-6-(2-hydroxyphenyl)-4-pyridinyl]phenyl}-L-asparagine;
N-{3-[2-amino-3-cyano-6-(2-hydroxyphenyl)-4-pyridinyl]phenyl}-3-(1-piperidinyl)propanamide;
5-({4-[2-amino-3-cyano-6-(2-hydroxyphenyl)-4-pyridinyl]phenyl}amino)-4-hydroxy-5-oxopentanoate;
4-[2-amino-3-cyano-6-(2-hydroxyphenyl)-4-pyridinyl]-N-[2-(1-piperidinyl)ethyl]-benzamide;
4-[2-amino-3-cyano-6-(2-hydroxyphenyl)-4-pyridinyl]benzoic acid;
5-({5-[2-amino-3-cyano-6-(2-hydroxyphenyl)-4-pyridinyl]-2-chlorophenyl}amino)-4-hydroxy-5-oxopentanoate;
N-{3-[2-amino-3-cyano-6-(2-hydroxyphenyl)-4-pyridinyl]phenyl}-2-[4-(2-furoyl)-1-piperazinyl]acetamide;
N-{3-[2-amino-3-cyano-6-(2-hydroxyphenyl)-4-pyridinyl]phenyl}-3-(4-ethyl-1-piperazinyl)propanamide;
N-{3-[2-amino-3-cyano-6-(2-hydroxyphenyl)-4-pyridinyl]phenyl}-3-octahydro-1(2H)-quinolinylpropanamide;
$N^1$-{3-[2-amino-3-cyano-6-(2-hydroxyphenyl)-4-pyridinyl]phenyl}-$N^2$-cyclopentylglycinamide;
$N^1$-{3-[2-amino-3-cyano-6-(2-hydroxyphenyl)-4-pyridinyl]phenyl}-$N^2$-(cyclopropylmethyl)glycinamide;
$N^1$-{3-[2-amino-3-cyano-6-(2-hydroxyphenyl)-4-pyridinyl]phenyl}-$N^2$-propylglycinamide;
$N^1$-{3-[2-amino-3-cyano-6-(2-hydroxyphenyl)-4-pyridinyl]phenyl}-$N^2$-(3-hydroxypropyl)glycinamide;
$N^1$-{3-[2-amino-3-cyano-6-(2-hydroxyphenyl)-4-pyridinyl]phenyl}-$N^3$-(cyclopropylmethyl)-β-alaninamide;
$N^1$-{3-[2-amino-3-cyano-6-(2-hydroxyphenyl)-4-pyridinyl]phenyl}-$N^2$,$N^2$-dimethylglycinamide;
N-{3-[2-amino-3-cyano-6-(2-hydroxyphenyl)-4-pyridinyl]phenyl}-2-(1-pyrrolidinyl)acetamide;
$N^1$-{3-[2-amino-3-cyano-6-(2-hydroxyphenyl)-4-pyridinyl]phenyl}-$N^2$-[2-(methyloxy)ethyl]glycinamide;
$N^1$-[5-[2-amino-3-cyano-6-(2-hydroxyphenyl)-4-pyridinyl]-2-(3-amino-1-pyrrolidinyl)phenyl]-β-alaninamide;
$N^1$-[5-[2-amino-3-cyano-6-(2-hydroxyphenyl)-4-pyridinyl]-2-(1-piperidinyl)phenyl]-β-alaninamide;
$N^1$-[5-[2-amino-3-cyano-6-(2-hydroxyphenyl)-4-pyridinyl]-2-(1-pyrrolidinyl)phenyl]-β-alaninamide;
$N^1$-{5-[2-amino-3-cyano-6-(2-hydroxyphenyl)-4-pyridinyl]-2-[ethyl(2-hydroxyethyl)amino]phenyl}-β-alaninamide;
$N^1$-[5-[2-amino-3-cyano-6-(2-hydroxyphenyl)-4-pyridinyl]-2-(4-morpholinyl)phenyl]-β-alaninamide;
$N^1$-[5-[2-amino-3-cyano-6-(2-hydroxyphenyl)-4-pyridinyl]-2-(dimethylamino)phenyl]-β-alaninamide;
N-{3-[2-amino-3-cyano-6-(2-hydroxyphenyl)-4-pyridinyl]-4-chlorophenyl}-3-(1-piperidinyl)propanamide;
2-[2-amino-3-cyano-6-(2-hydroxyphenyl)-4-pyridinyl]benzoic acid;
2-[2-amino-3-cyano-6-(2-hydroxyphenyl)-4-pyridinyl]-N-[2-(1-piperidinyl)ethyl]-benzamide;
$N^1$-{5-[2-amino-3-cyano-6-(2-hydroxyphenyl)-4-pyridinyl]-2-chlorophenyl}-$N^2$-(cyclopropylmethyl)glycinamide;
$N^1$-{5-[2-amino-3-cyano-6-(2-hydroxyphenyl)-4-pyridinyl]-2-chlorophenyl}-$N^2$-(2-methoxyethyl)glycinamide;
$N^1$-{5-[2-amino-3-cyano-6-(2-hydroxyphenyl)-4-pyridinyl]-2-chlorophenyl}-β-alaninamide;
2-amino-4-(4-amino-3-hydroxyphenyl)-6-(2-hydroxyphenyl)nicotinonitrile;
N-{4-[2-amino-3-cyano-6-(2-hydroxyphenyl)-4-pyridinyl]-2-hydroxyphenyl}acetamide;
N-{5-[2-amino-3-cyano-6-(2-hydroxyphenyl)-4-pyridinyl]-2-chlorophenyl}-3-(1-piperidinyl)propanamide;
$N^1$-[5-[2-amino-3-cyano-6-(2-hydroxyphenyl)-4-pyridinyl]-2-(dimethylamino)phenyl]-$N^2$-(cyclopropylmethyl)glycinamide;
N-[5-[2-amino-3-cyano-6-(2-hydroxyphenyl)-4-pyridinyl]-2-(dimethylamino)phenyl]-3-(1-piperidinyl)propanamide;
$N^1$-{5-[2-amino-3-cyano-6-(2-hydroxyphenyl)-4-pyridinyl]-2-[(2S)-2-(hydroxymethyl)-1-pyrrolidinyl]phenyl}-L-leucinamide;
$N^1$-{5-[2-amino-3-cyano-6-(2-hydroxyphenyl)-4-pyridinyl]-2-[(3S)-3-(dimethylamino)-1-pyrrolidinyl]phenyl}-$N^2$-(cyclopropylmethyl)glycinamide;
$N^1$-(5-[2-amino-3-cyano-6-(2-hydroxyphenyl)-4-pyridinyl]-2-{3-[(trifluoroacetyl)amino]-1-pyrrolidinyl}phenyl)-L-leucinamide;
N-(5-[2-amino-3-cyano-6-(2-hydroxyphenyl)-4-pyridinyl]-2-{3-[(trifluoroacetyl)amino]-1-pyrrolidinyl}phenyl)-3-(1-piperidinyl)propanamide;
$N^1$-(5-[2-amino-3-cyano-6-(2-hydroxyphenyl)-4-pyridinyl]-2-{3-[(trifluoroacetyl)amino]-1-pyrrolidinyl}phenyl)-$N^2$-(2-methoxyethyl)glycinamide;
$N^1$-(5-[2-amino-3-cyano-6-(2-hydroxyphenyl)-4-pyridinyl]-2-{3-[(trifluoroacetyl)amino]-1-pyrrolidinyl}phenyl)-$N^2$-(cyclopropylmethyl)glycinamide;
2-amino-6-(2-hydroxyphenyl)-4-(3-hydroxyphenyl)nicotinonitrile;
N-{4-[2-amino-3-cyano-6-(2-hydroxyphenyl)-4-pyridinyl]-2-[2-(1-piperidinyl)ethoxy]phenyl}acetamide;
N-{4-[2-amino-3-(hydroxymethyl)-6-(2-hydroxyphenyl)-4-pyridinyl]-2-hydroxyphenyl}acetamide;
2-[6-amino-4-[4-(ethylamino)-3-hydroxyphenyl]-5-(hydroxymethyl)-2-pyridinyl]-3-(cyclopropylmethoxy)phenol;
N-{4-[2-amino-6-[2-(cyclopropylmethoxy)-6-hydroxyphenyl]-3-(hydroxymethyl)-4-pyridinyl]-2-hydroxyphenyl}acetamide;
7-[2-(cyclopropylmethoxy)-6-hydroxyphenyl]-5-(3-ethyl-2-oxo-2,3-dihydro-1,3-benzoxazol-6-yl)-1,4-dihydro-2H-pyrido[2,3-d][1,3]oxazin-2-one;

and pharmaceutically acceptable salts thereof.

The compound of the formula (I) of the present invention can be, but not limited to be, prepared by combining various known methods. In some embodiments, one or more of the substituents, such as amino group, carboxy group, and hydroxy group of the compounds used as starting materials or intermediates are advantageously protected by a protecting group known to a person skilled in the art. Examples of the protecting groups are described in "Protective Groups in Organic Synthesis ($2^{nd}$ Edition)" by Greene and Wuts.

The typical processes for preparing the compounds (I) of the present invention are explained below.

(1) The compound of the formula (I-a):

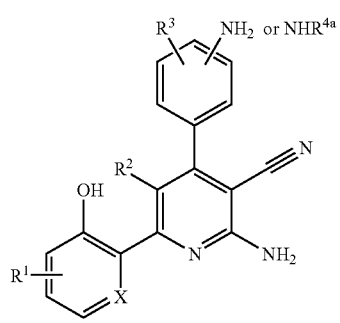

in which

X, $R^1$, $R^2$ and $R^3$ are the same as defined above and $R^{4a}$ is $C_{1-6}$ alkylsulfonyl, or —$COR^{41}$ ($R^{41}$ is the same as defined.), can be prepared, for example, by the following reaction A.

Reaction A

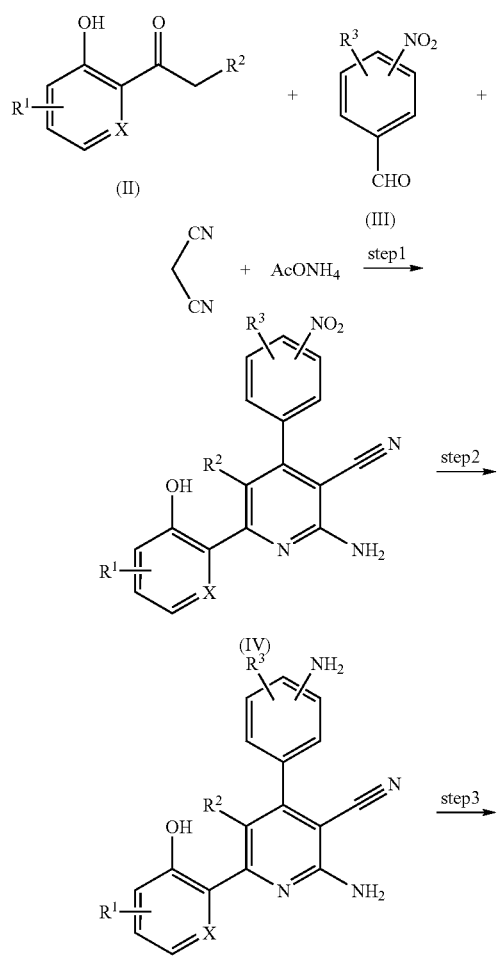

-continued

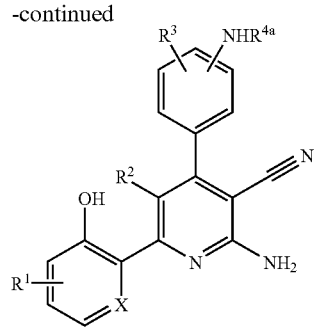

In the step 1, the compound of the formula (II):

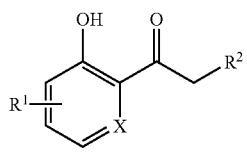

(wherein $R^1$, $R^2$ and X are the same as defined above), is reacted with an aldehyde of the formula (III):

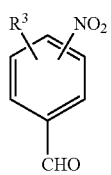

(wherein $R^3$ is the same as defined above), malononitrile, and ammonium acetate to prepare the compound (IV).

In step 2, the nitro group is reduced to convert to the amino group.

In step 3, the amino group is further modified to obtain a desired group (NHR$^{4a}$).

The substituents of the compound (II) or (III) are, if necessary, protected by an appropriate protecting group (e.g., benzyl, silyl) during the reaction, and deprotected afterward.

The step 1 is carried out without a solvent or in a solvent including, for instance, ethers, such as dioxane, and tetrahydrofuran; aromatic hydrocarbons such as benzene, toluene and xylene; nitrites such as acetonitrile; amides such as dimethylformamide (DMF) and dimethylacetamide; sulfoxides such as dimethyl sulfoxide, and others.

The reaction temperature is optionally set depending on the compounds to be reacted. The reaction temperature is usually about 50° C. to 200° C. The reaction is conducted for, usually, 30 minutes to 48 hrs. and preferably 1 to 24 hrs.

The compounds of (II) and (III) can be commercially available, or can be prepared by the use of known techniques.

The step 2 is carried out in the presence of a reducing agent and a hydrogen donor at about room temperature to 120° C. The reaction time and the solvent used in the step 2 are similar as that used in the step 1.

The step 3 is carried out under the condition usually employed by a skilled person in the art to synthesize amides (NHR$^{4a}$).

(2) Alternatively, the compound of the formula (I-b):

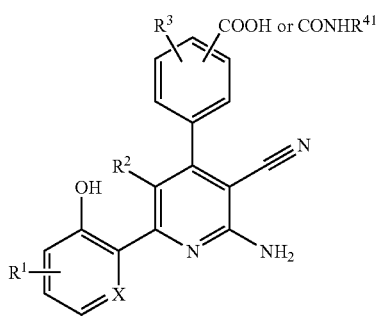

(I-b)

wherein

X, R$^1$, R$^2$, R$^3$ and R$^{41}$ are the same as defined above, can be prepared, for example, by the following reaction B.

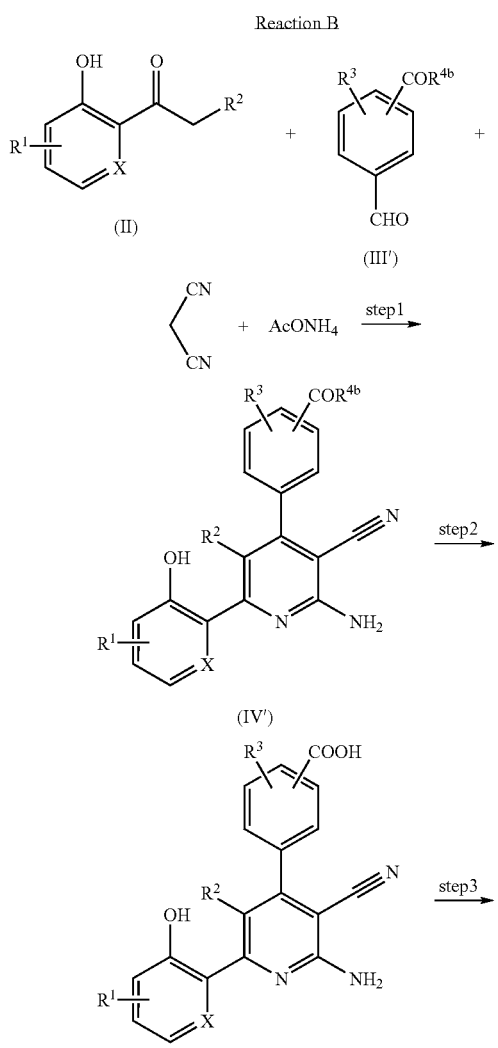

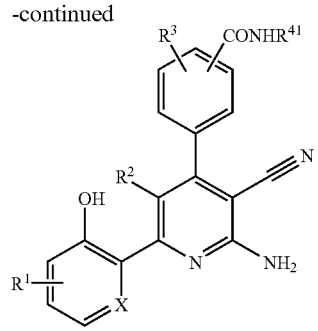

The compound (II) is reacted with an aldehyde of the formula (III'):

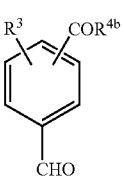

(III')

(wherein

R$^3$ is the same as defined above, and R$^{4b}$ is amino or alkoxy), malononitrile, and ammonium acetate to prepare the compound (IV'). R$^{4b}$ is further modified to obtain a desired group (OH or NHR$^{41}$).

The substituents of the compound of (II) or (III) are, if necessary, protected by an appropriate protecting group (e.g., benzyl, silyl) during the reaction, and deprotected afterward.

The step 1 of the reaction B can be carried out under the similar condition to that of reaction A.

The step 2 in the reaction B can be hydrolysis and can be carried out under the condition usually employed by a skilled person in the art.

The step 3 in the reaction B can be carried out under the condition usually employed by a skilled person in the art to synthesize amides (CONHR$^{41}$).

(3) Alternatively, the compound of the formula (I-c):

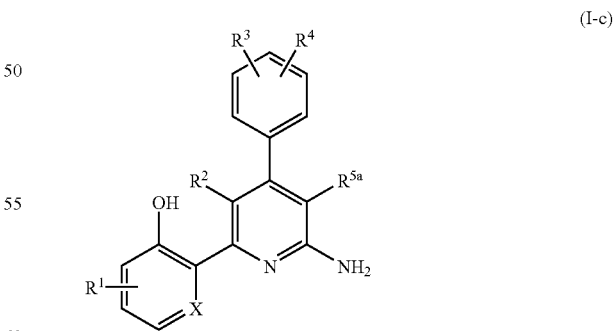

(I-c)

wherein

X, R$^1$, R$^2$, R$^3$ and R$^4$ are the same as defined, and R$^{5a}$ is carboxy, carbamoyl, C$_{1-6}$ alkoxycarbonyl, hydroxy C$_{1-6}$ alkyl, C$_{1-6}$ alkylcarbamoyl, or C$_{1-6}$ alkyl, can be prepared, for example, by the following reaction C.

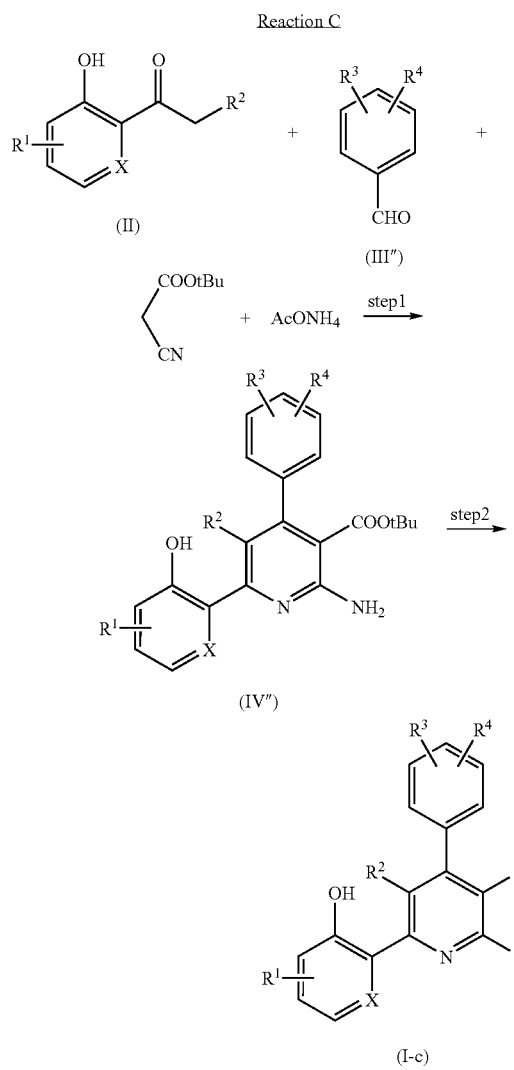

(wherein
R³ and R⁴ are the same defined above), a nitrile of the formula, tBu-OCO—CH₂CN, and ammonium acetate to prepare the compound (IV″). Then COOtBu of the resulting compound (IV″) can be modified to obtain a desired compound ($R^{5a}$).

The substituents of the compound of (II) or (III″) may be protected by an appropriate protecting group (e.g., benzyl, silyl) during the reaction, and deprotected afterward.

The step 1 of the reaction C can be carried out under the similar condition to that of reaction A.

The step 2 of the reaction C can be, for example, a hydrolysis reaction, decarboxylation, reducing reaction, amide synthesis, etc. The conditions of the step 2 can be the same as that usually employed by a skilled person in the art.

The amino group at position 2 of the pyridine ring in the compounds (I-a), (I-b) and (I-c) is, if necessary, modified according to conventional method to prepare other groups such as alkylamino, alcanoylamino, and the like.

Typical procedures for preparing saturated or unsaturated heteroring compounds that are formed by R⁵ and R⁶ in formula I, together with the carbon atoms in the pyridine ring, are as follows.

The starting compound is I-d: wherein X, R¹, R², R³ and R⁴ are the same as defined above.

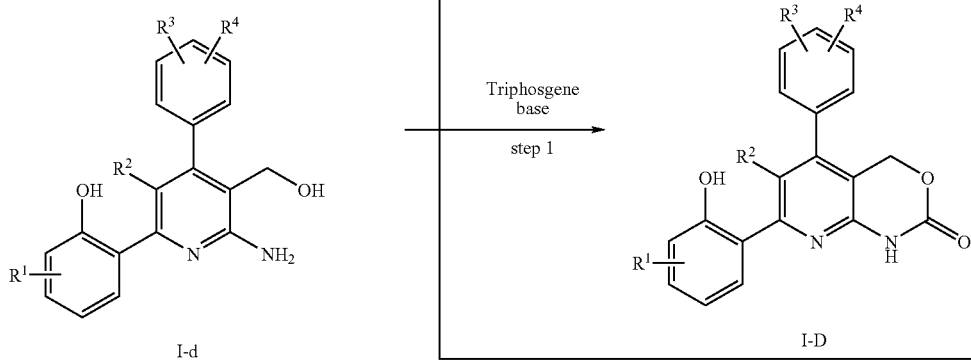

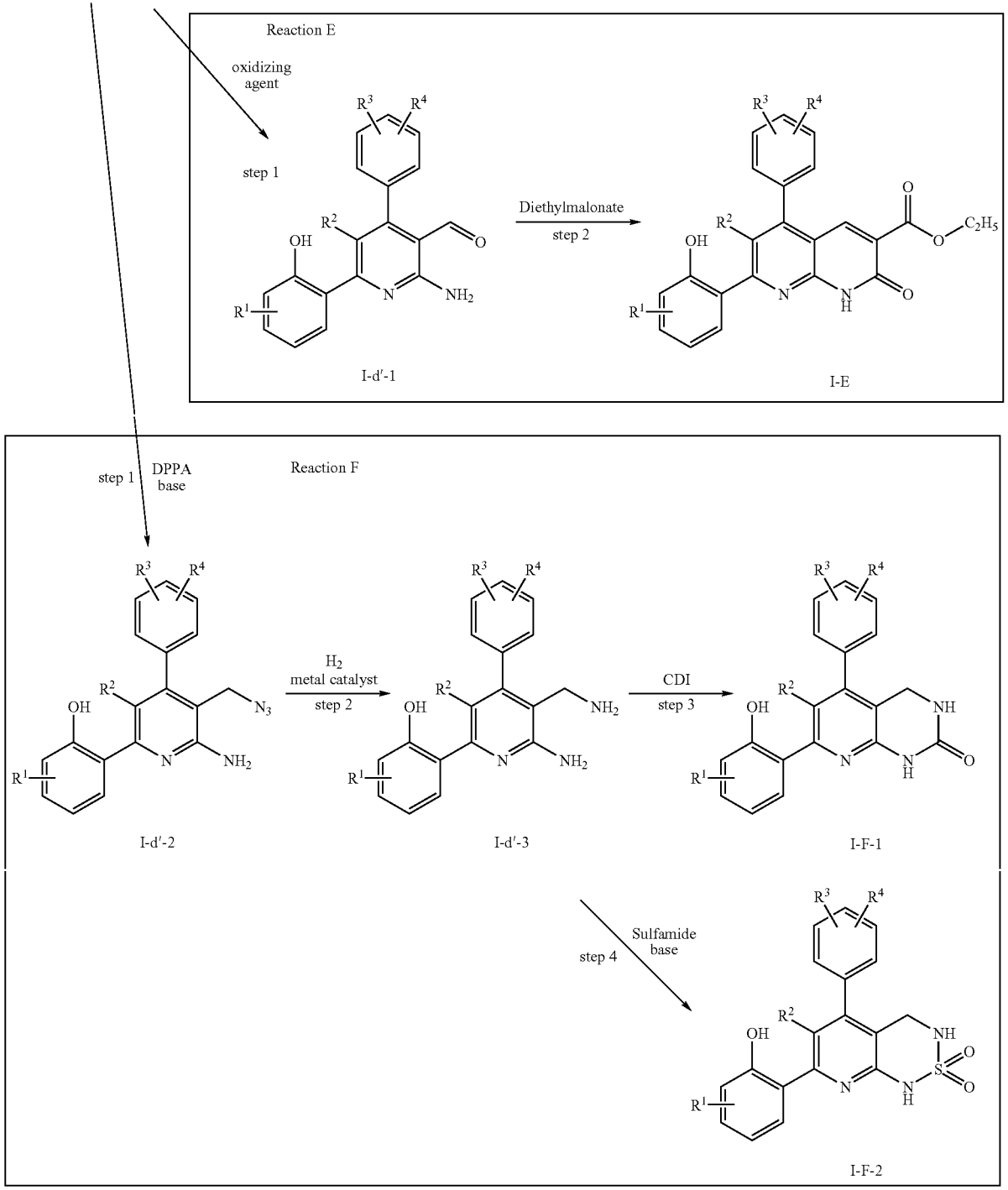

In the step 1 of reaction D, starting compound of formula I-d in a suitable solvent with a suitable organic base can be treated with triphosgene by known method to give a desired compound represented by the formula I-D.

In the step 1 of reaction E, starting compound of formula I-d in a suitable solvent can be treated with oxidizing agent such as manganese dioxide, nitric acid and pyridinium chlorochromate (PCC) for preparing a compound represented by the formula I-d'-1.

In the step 2 of reaction E, a formula I-d'-1 in a suitable solvent can be treated with diethylmalonate and suitable base to give a desired compound represented by the formula I-E.

In the step 1 of reaction F, starting compound of formula I-d in a suitable solvent can be treated with phosphonic ester reagent such as diphenylphosphoryl azide (DPPA) and suitable base for preparing a compound represented by the formula I-d'-2.

In the step 2 of reaction F, compound I-d'-2 can be treated with hydrogen in the presence of a metal catalyst such as palladium on carbon (Pd/C) in a solvent for preparing a compound represented by the formula I-d'-3.

In the step 3 of reaction F, compound I-d'-3 in a suitable solvent can be treated with 1,1'-carbonyldiimidazole (CDI) to give a desired compound formula I-F-1.

In the step 4 of reaction F, compound I-d'-3 can be treated with sulfamide and suitable base to give a desired compound represented by the formula I-F-2.

The suitable solvents for the individual steps in the reactions D to F are not limited, but can be selected from the group consisting of ethers, such as dioxane, diethylether, tetrahydrofuran (THF), glycol dimethyl ether, or alcohols such as, propanol, butanol, isopropanol, ethanol diisopropyl ether or esters, such as ethyl acetate, butyl acetate 1, or aromatic hydrocarbons such as benzene, toluene, xylene, hexane or nitrites such as acetonitrile or amides such as dimethylformamide (DMF), dimethylacetamide or sulfoxides such as dimethyl sulfoxide or halogenated hydrocarbons such as dichloromethane, trichloromethane and others. Having described some examples of suitable solvents, the present examples are illustrative and not restrictive. The suitable solvents for the individual steps can be selected by the person skilled in the art.

The suitable inorganic or organic bases for the individual steps in the reactions D to F are not limited, but can be selected from the group comprising for instance, such as alkaline earth metal or alkali metal hydroxides, alkoxides, acetates, carbonates or bicarbonates, such as, sodium hydroxide, potassium hydroxide or ammonium hydroxide, sodium methoxide, sodium ethoxide, or potassium tert-butoxide, sodium acetate, potassium acetate, calcium acetate or ammonium acetate, sodium carbonate, potassium carbonate or ammonium carbonate, sodium bicarbonate or potassium bicarbonate and also tertiary amines, such as trimethylamine, triethylamine, tributylamine, ethyl-diisopropylamine, N,N-dimethylaniline, N,N-dimethyl-benzylamine, pyridine, picoline, N-methylpiperidine, N-methylmorpholine, N,N-dimethylaminopyridine, diazabicyclooctane (DABCO), diazabicyclononene (DBN) or diazabicycloundecene (DBU). Having described some examples of suitable inorganic and organic bases, the present examples are illustrative and not restrictive. The suitable bases for the individual steps can be selected by the person skilled in the art.

The reaction temperature is optionally set depending on the compounds to be reacted. The reaction temperature is usually about 0° C. to 150° C. The reaction is conducted for, usually, 30 minutes to 48 hrs. and preferably 1 to 24 hrs.

When the compound shown by the formula (I) or a salt thereof has geometrical isomers and/or conformational isomers, each of their separated isomer and mixtures are also included in the scope of the present invention.

When the compound shown by the formula (I) or a salt thereof has an asymmetric carbon(s) in the structure, their optically active compounds and racemic mixtures are also included in the scope of the present invention.

Typical salts of the compound shown by the formula (I) include salts prepared by the reaction of the compound of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydroiodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tri(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

Examples of such salts are sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sevacate, fumarate, maleate, butyne-1,4-dioate, hexyne-1,6-dioate, benzoate, chlorobenzoate, methoxybenzoate, phthalate, sulfonate, xylenesulfonate, phenylacetate, phenylpropionate, phenylbutyrate, citrate, lactate, γ-hydroxybutyrate, glycollate, tartarate, methanesulfonate, propanesulfonate, naphthalene-1-sulfonate, naphthalene-2-sulfonate, mandelate, and the like salts of the compound of formula (I).

The preferred acid addition salts are those formed with mineral acids, such as, without limitation, hydrochloric acid, and hydrobromic acid, and those formed with organic acids, such as without limitation, maleic acid and methanesulfonic acid. The potassium and sodium salt forms are particularly preferred base addition salts.

The compound of the present invention may be administered in oral forms, such as, without limitation normal and enteric coated tablets, capsules, pills, powders, granules, elixirs, tinctures, solution, suspensions, syrups, solid or liquid aerosols and emulsions. They may also be administered in parenteral forms, such as, without limitation, intravenous, intraperitoneal, subcutaneous, intramuscular, and the like forms, well-known to an ordinary skilled person in the pharmaceutical arts.

The compounds of the present invention can be administered in intranasal form via topical use of suitable intranasal vehicles, or from transdermal routes, using transdermal delivery systems well-known to an ordinary skilled person in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically acceptable excipients. Excipients are inert substances such as, without limitation carriers, diluents, flavoring agents, sweeteners, lubricants, solubilizers, suspending agents, binders, tablet disintegrating agents and encapsulating material.

Another embodiment of the present invention is a pharmaceutical formulation comprising the compound of the invention and one or more pharmaceutically acceptable excipients that are compatible with the other ingredients of the formulation and not deleterious to the recipient thereof. Pharmaceutical formulations of the present invention are prepared by combining a therapeutically effective amount of the compound of the invention together with one or more pharmaceutically acceptable excipients therefor. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with non-toxic, pharmaceutically acceptable carriers, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, tragacanth, sodium alginate, carboxymethyl cellulose, polyethylene glycol, waxes, and the like; and, optionally, lubricants, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and a sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

The effects of the compounds of the present invention were examined by the following assays and pharmacological tests.

IKK-β Kinase Inhibitory Assay.

(1) Preparation of IKK-β Kinase Protein.

A cDNA fragment encoding human IKK-β open reading frame was generated by PCR with the use of a pair of primers designed from the published sequence (Woronicz J D et al. (1997) Science 278, 866-869). A template was obtained from Quickclone cDNA (Clontech) using Elongase™ Amplification kit (Life Technologies). The DNA fragments generated by PCR were gel-purified and subcloned into pBluescript. The cDNA fragment cloned in pBluescript was inserted into pcDNA3.1/His C KpnI/NotI, and transferred into pVL1393 SmaI/XbaI (Pharmingen) to construct a baculovirus transfer vector. Then the vector, together with the linearized baculovirus (BaculoGold™, Pharmingen) was used to transfect Sf21 cells (Invitrogen, San Diego, Calif.). Generated recombinant baculovirus was cloned and amplified in Sf21 cells, grown in TNM-FH insect cell medium (Life Technologies, Inc.) supplemented with 10% FCS, 50 g/ml Gentamycin, 0.1% Pluronic F-68 (Life Technologies, Inc.) as suspension culture (200 ml in 1 L Erlenmeyer flask; 27° C.; 130 rpm). Sf21 cells were infected with this amplified virus with a multiplicity of infection of 5 following standard protocols (Crossen R, Gruenwald S (1997) Baculovirus Expression Vector System Instruction Manual, Pharmingen Corporation) and harvested 48 hrs. later. The cells were lysed to obtain the produced chimeric protein of IKK-β kinase fused by histidine (His-tagged IKK-beta).

(2) The Preparation of Purified GST-IκBα Fusion Proteins

An expression vector containing the nucleotide sequence encoding fusion protein of GST with amino acid residues 1 to 54 of IκBα under the control of an IPTG-inducible promoter was constructed. The expression vector was introduced in $E.\ coli$ and the transformant was cultured and lysed to obtain a GST-IκBα fusion protein. Then the resulting GST-IκBα fusion protein was purified and biotinated for kinase assay.

(3) The Measurement of IKK-β Kinase Activity

The 96-well format kinase assay of IKK-β was performed to test the inhibitory activity of the compounds of the present invention. First, 5 μl of a test compound was put in the presence of 2.5% dimethyl sulfoxide (DMSO) in each well in a U-bottomed 96-well plate (Falcon). For control wells of background (BG) and total phosphorylation (TP), 5 μl of 2.5% DMSO was put. Recombinant IKK-β (final 0.6 μg/ml) and bio-GST-IκBα (1-54) (final 0.2 μM) were diluted in 25 μl of 2×kinase buffer β (40 mM Tris-HCl, pH 7.6, 40 mM MgCl$_2$, 40 mM β-glycerophosphate, 40 mM p-nitrophenyl-phosphate, 2 mM EDTA, 40 mM creatine phosphate, 2 mM DTT, 2 mM Na$_3$VO$_4$, 0.2 mg/ml BSA and 0.8 mM phenylmethylsulfonyl fluoride) and transferred to the 96-well plate. Bio-GST-IκBα (1-54) in 25 μl of 2×kinase buffer β without IKK-β was transferred to BG wells. Then 20 μl of 12.5 μM ATP, 62.5 μCi/ml [γ-$^{33}$P] ATP (Amersham Pharmacia Biotech) was added and the resulting mixture was incubated for 2 hrs. at room temperature. The kinase reactions were terminated by the addition of 150 μl of termination buffer (100 mM EDTA, 1 mg/ml BSA, 0.2 mg NaN$_3$). One handred and fifty µl of the sample was transferred to a streptavidin-coated, white MTP (Steffens Biotechniche Analysen GmbH #08114E14. FWD) to capture the biotinylated substrates. After 1 hr. of incubation, non-bound radioactivity was eliminated by washing the wells five times with 300 µl of washing buffer including 0.9% NaCl and 0.1% (w/v) Tween-20 with the use of a MW-96 plate washer (BioTec). The bound radioactivity was determined after the addition of 170 µl MicroScint-PS scintillation cocktail (Packard) using a TopCount scintillation counter.

Syk Tyrosine Kinase Inhibitory Assay for Selectivity.
(1) Preparation of Syk Protein A cDNA fragment encoding human Syk openreading frame was cloned from total RNA of human Burkitt's lymphoma B cell lines, Raji (American Type Culture Collection), with the use of RT-PCR method. The cDNA fragment was inserted into pAcG2T (Pharmingen, San Diego, Calif.) to construct a baculovirus transfer vector. Then the vector, together with the linearized baculovirus (BaculoGold™, Pharmingen), was used to transfect Sf21 cells (Invitrogen, San Diego, Calif.).

Generated recombinant baculovirus was cloned and amplified in Sf21 cells. Sf21 cells were infected with this amplified high titer virus to produce a chimeric protein of Syk kinase fused by glutathione-S-transferase (GST).

The resulting GST-Syk was purified with the use of glutathione column (Amersham Pharmacia Biotech AB, Uppsala, Sweden) according to the manufacturer's instruction. The purity of the protein was confirmed to be more than 90% by SDS-PAGE.

(2) Synthesize of a Peptide

Next, a peptide fragment of 30 residues including two tyrosine residues, KISDFGLSKALRADE-NYYKAQTHGKWPVKW, was synthesized by a peptide synthesizer. The N-terminus of the fragment was then biotinylated to obtain biotinylated activation loop peptide (AL).

(3) The Measurement of Syk Tyrosine Kinase Activity

All reagents were diluted with the Syk kinase assay buffer (50 mM Tris-HCl (pH 8.0), 10 mM MgCl$_2$, 0.1 mM Na$_3$VO$_4$, 0.1% BSA, 1 mM DTT). First, a mixture (35 µl) including 3.2 µg of GST-Syk and 0.5 µg of AL was put in each well in 96-well plates. Then 5 µl of a test compound in the presence of 2.5% dimethyl sulfoxide (DMSO) was added to each well. To this mixture was added 300 µM ATP (10 µl) to initiate the kinase reaction. The final reaction mixture (50 µl) consists of 0.65 nM GST-Syk, 3 µM AL, 30 µM ATP, a test compound, 0.25% DMSO, and a Syk kinase assay buffer.

The mixture was incubated for 1 hr. at room temperature, and the reaction was terminated by the addition of 120 µl of termination buffer (50 mM Tris-HCl (pH 8.0), 10 mM EDTA, 500 mM NaCl, 0.1% BSA). The mixture was transferred to streptavidin-coated plates and incubated for 30 minutes. at room temperature to combine biotin-AL to the plates. After washing the plates with Tris-buffered saline (TBS) (50 mM Tris-HCl (pH 8.0), 138 mM NaCl, 2.7 mM KCl) containing 0.05% Tween-20 for 3 times, 100 µl of antibody solution consisting of 50 mM Tris-HCl (pH 8.0), 138 mM NaCl, 2.7 mM KCl, 1% BSA, 60 ng/ml anti-phosphotyrosine monoclonal antibody, 4G10 (Upstate Biotechnology), which was labeled with europium by Amersham Pharmacia's kit in advance, was added and incubated at room temperature for 60 minutes. After washing, 100 µl of enhancement solution (Amersham Pharmacia Biotech) was added and then time-resolved fluorescence was measured by multilabel counter ARVO (Wallac Oy, Finland) at 340 nm for excitation and 615 nm for emission with 400 msec of delay and 400 msec of window.

The Measurement of RANTES Production in Response to TNF-α from A549 Cells.
(1) Preparation of A549 Cells.

The A549 human lung epithelium cell line (ATCC #CCL-885) was maintained in Dulbecco's modified Eagle's medium (D-MEM, Nikken Biomedical Institute) supplemented with 10% FCS (Gibco), 100U/ml penicillin, 100 µg/ml streptomycin, and 2 mM glutamine (culture medium). Forty thousand ($4 \times 10^4$) cells (80 µl/well) were seeded in each well of 96 well flat-bottom tissue culture plate (Falcon #3072). The plate was allowed to stand for 2 hrs., thus the cells were adhered to the bottom of each well. To the each well was added 10 µl vehicle (1% DMSO), serial dilutions of test compounds in 1% DMSO, or 5 nM Dexamethasone in 1% DMSO as a reference. The mixture (90 µl/well) was incubated for 1 hr. at 37° C. After 1 hr., 1 µg/ml TNF-α (10 µl) in culture medium was added to the mixture to obtain 100 µl of reaction mixture. The reaction mixture was cultured for 24 hrs. to stimulate the cells with 100 ng/ml TNF-α. Cells with vehicle without TNF-α stimulation were also prepared.

(2) Enzyme Immunoassay

Then the concentration of RANTES released from the cells in the supernatants of each well was determined using a quantitative sandwich enzyme immunoassay technique. First, 2 µg/ml mouse anti-huRANTES mAb (R&D Systems, #mAb678) in PBS buffer (pH 7.4, 100 µl) was put in each well of 96-well NUNC fluoro plate (Nalge Nunc, New York USA) (Final 200 ng/well) and the plate was allowed to stand for overnight at 4° C. to be coated by the antibody. Each well of the plate was then washed with 350 µl wash buffer (0.05% Tween-20, 0.85% NaCl, and 25 mM Tris/HCl pH 7.4) for three times. Blocking buffer containing 1% BSA (Sigma 99% pure, 100 g), 5% sucrose (Nacalai tesque, 99% pure, 500 g), and 0.02% azide (Nacalai tesque, 100%, 500 g) were added (200 µl) to each well and then the plate was allowed to stand for 4 hrs. to stabilize the coated antibody.

Next, 50 µl supernatants of cell culture prepared in (1) above were put in each well of the 96-well NUNC fluoro plate with coated antibody. Recombinant Human RANTES (Pepro Tech, Inc. #300-06) was used as the standard for the determination of RANTES production (linear range between 1 and 10 ng/ml). Eu-labelled mouse anti-huRANES mAb (60 ng/ml: R&D Systems, #mAb278) in PBS supplemented by 1% BSA and 0.05% Tween 20 was added (50 µl) to each well. The reaction mixtures were incubated at room temperature for 4 hrs. After washing with wash buffer (0.05% Tween-20, 0.85% NaCl, and 25 mM Tris/HCl pH 7.4, 350 µl/well) for 5 times with the use of a Sera Washer (Bio-Tech, #MW-96R), the enhancement solution (DELFIA, #1244-405, 100 µl/well) was added to each well. The plate was incubated for 10 minutes at room temperature with moderate shaking. Fluorescent intensity was measured using a DELFIA fluorimeter (Wallac). Excitation was performed at 340 nm and emission was measured at 615 nm.

The Measurement of IL-2 Production in Jurkat T Cells in Response to Antibody Stimulation.

IL-2 production was measured in Jurkat T cells (E6-1 clone; ATCC # TIB-152) in response to stimulation with anti-CD3/anti-CD28 antibodies.

(1) Preparation of Immobilized Antibodies

First, anti-CD3 antibodies (400 ng/well Nichirei, NU-T3 4 μg/ml in 100 μl Dulbecco's PBS) were put in each well of 96-well plate (Falcon #3072) and the plate was allowed to stand for 2 hrs. at room temperature to be coated with the antibody. Each well of the plate was then washed with 250 μl PBS 3 times.

(2) Preparation of Jurkat Cell Culture

Jurkat T cells were cultured in RPMI 1640 medium supplemented with 10% heat-inactivated fetal calf serum, 2 mM L-glutamine, 100 U/ml penicillin G, and 100 μg/ml streptomycin (culture medium). Two hundred thousand ($2\times10^5$) cells (190 μl/well) were seeded in each well of 96-well U-bottom tissue culture plates (Falcon #3077). To each well was added 10 μl vehicle (0.2% DMSO), serial dilution of compounds in 0.2% DMSO, or 25 nM cyclosporin A as a reference in 0.2% DMSO. The mixture (200 μl) was incubated for 1 hr. at 37° C. in a humidified 5% $CO_2$ environment.

(3) Stimulation of the Cell

The reaction mixture obtained in (2) (100 μl) was put in the each well of the antibody-immobilized plate prepared in (1). To this well was added anti-CD28 antibodies (Nichirei, KOLT-2, 6 μg/ml in cell culture medium, 50 μl/well) and 2.5 μg/ml goat anti-mouse kappa chain antibodies (Bethyl Laboratories, (Cat#A90-119A) 10 μg/ml in culture medium, 50 μl/well). The reaction mixture in each well was incubated for 24 hrs. at 37° C. to stimulate cells with immobilized anti-CD3 antibodies (400 ng/well) and anti-CD28 antibodies (1.5 μg/ml), and then to cross-link receptors on the cells with anti-mouse kappa chain antibodies (2.5 μg/ml).

(4) Measurement of IL-2 Production

The supernatants of the reaction mixture were then collected. The IL-2 concentration in the supernatants was determined using a DuoSet™ ELISA Development Kit (GenzymeTechne, Minneapolis, USA) following the manufacturer's recommendations. First, 2 μg/ml of mouse anti-huIL-2 Ab in PBS buffer (100 μl) was put in each well of 96-well plate (NUNC, Maxisorp™) and the plate was allowed to stand for overnight at 4° C. to be coated with the antibody. Each well of the plate was then washed 5 times with 350 μl of wash buffer containing PBS, 0.05% Tween 20 (Nakalai tesque) using Sera Washer (Bio-Tech, #MW-96R). To each well was added 250 μl of 1% BSA (Sigma) in PBS, 0.05% Tween 20 (dilution buffer). After 2 hrs. incubation at room temperature, the buffer was discarded, and 50 μl of culture medium was added. Next, 50 μl supernatant of stimulated cell culture prepared (3) above was put in each well of the 96-well plate with coated mouse anti-huIL-2 antibody. Recombinant Human IL-2 (Genzyme Techne) was used as the standard for the determination of IL-2 production (linear range between 200 and 5,400 pg/ml). The reaction mixtures were incubated for 1 hr. at room temperature. After 5 times washing, 100 μl biotinylated rabbit anti-huIL-[2] antibody (Genzyme Techne, 1.25 μg/ml) in dilution buffer was added to each well, and incubated at room temperature for 1 hr. After 5 times washing, 100 μl of Streptavidin-conjugated horseradish-peroxidase (Genzyme Techne, 1/1000 in dilution buffer) was added to each well. After 20 minutes, each well of the plate was washed 5 times with wash buffer (350 μl/well). Substrate and $H_2O_2$ (TMBZ peroxidase detection kit, SUMILON #ML-1120T) were added to the mixture and the mixture was allowed to stand at room temperature. The reaction was terminated after 10 minutes by adding 2N $H_2SO_4$. Optical density at 450 nm was measured with the use of a microplate reader (Labosystems, Multiscan Multisoft). Quantification of IL-2 production in each sample was performed by comparison of optical densities between each sample and the standard curve.

Mouse LPS-induced TNF-α Production

Eight weeks old BALB/c female mice were placed into two groups, a control group and a treated group. A solution containing 200 μg/mouse of LPS in 0.9% physiological salt was administered by intraperitoneal (i.p.) injection into the control mice. Mice in the treated group were first injected i.p. with compounds of the present invention 30 minutes prior to the LPS injection. Under anesthesia with pentobarbital (80 mg/kg, i.p.), blood was collected from the posterior venous cavity) of the treated and control mice at 90 min post-LPS injection into 96-well plate containing 2% EDTA solution. The plasma was separated by centrifugation at 1800 rpm for 10 minutes at 4° C. and then diluted with four times volumes of phosphate buffer saline (pH 7.4) containing 1% bovine serum albumin. TNF-α concentration in the sample was determined using an ELISA kit (Pharmingen, San Diego, Calif.)

The mean TNF-α level in 5 mice from each group was determined and the percent reduction in TNF-α levels was calculated. The treated mice showed significant decrease in the level of TNF-α as compared to the control mice. The result indicates that the compounds of the present invention can restrain LPS-induced cytokine activity.

The results of a in vitro test and cellular assay tests (A549 and Jurkat) are shown in the tables in the Examples below. The data corresponds to the compounds as yielded by solid phase synthesis and thus to levels of purity of about 40 to 90%. For practical reasons, the compounds are grouped in four classes of activity as follows:

In vitro $IC_{50}$=A 0.5 μM<B 2 μM<C 10 μM<D

Cellular $IC_{50}$=A 1 μM<B 10 μM<C

The compounds of the present invention also show excellent selectivity, and strong activity in vivo assays.

EXAMPLES

The present invention will be described in detail below in the form of examples, but they should by no means be construed as defining the metes and bounds of the present invention.

In the examples below, all quantitative data, if not stated otherwise, relate to percentages by weight. $^1$H NMR spectra were recorded using either Bruker DRX-300 (300 MHz for $^1$H) spectrometer in $CDCl_3$. Chemical shifts are reported in parts per million (ppm) with tetramethylsilane (TMS) as an internal standard at zero ppm. Coupling constant (J) are given in hertz and the abbreviations s, d, t, q, m, and br refer to singlet, doblet, triplet, quartet, multiplet, and broad, respectively. The mass determinations were carried out by MAT95 (Finnigan MAT).

Preparing Method of Starting Compounds:

Starting Compound 1A: 2-Benzyloxyacetophenone

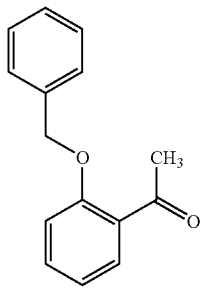

A mixture of 2'-hydroxyacetophenone (68.1 g, 0.500 mol), benzylbromide (65.4 ml, 94.1 g, 0.550 mol) and $K_2CO_3$ (103 g, 0.750 mol) in acetone (1.00L) was stirred and heated to reflux overnight. The resulting mixture was concentrated under reduced pressure to obtain a residue. The obtained residue was dissolved in the mixture of AcOEt and water and then extracted with AcOEt. The extract was washed with brine, dried over magnesium sulfate, filtered, and concentrated under reduced pressure to give a crude material. The crude material was purified by distillation under reduced pressure to give starting compound 1A as a colorless oil (100 g, yield 88%).

Starting Compound 1A'; 1-{2-(cyclopropyl-methoxy)-6-[(4-methoxybenzyl)oxy]phenyl}ethanone

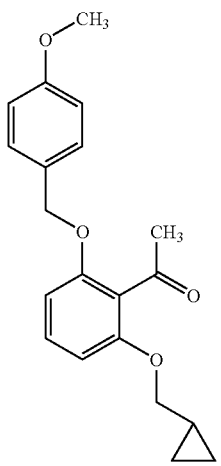

To a stirred solution of 1-(2,6-dihydroxyphenyl)ethanone (50.0 g, 328 mmol) in acetone (1000 mL) was added potassium carbonate (227 g, 1643 mmol) and (bromomethyl)cyclopropane (35.1 mL, 361 mmol). The mixture was stirred at 50° C. for 2 days. The reaction mixture was filtrated on celite, and then the filtrate was concentrated under reduced pressure. The residue was diluted with water and extracted with ethyl acetate. The separated organic phase was washed with water and brine, dried over $MgSO_4$, filtered and concentrated under reduced pressure. The residue was suspended in hexane. Then the suspension was stirred at 80° C. for 30 minuets. The solution was filtered and the filtrate was allowed to cool to room temperature. The resulting white solid was collected by filtration, washed with hexane, and dried under reduced pressure to give 1-{2-[(cyclopropylmethyl)oxy]-6-hydroxyphenyl}ethanone as a pale yellow solid (56.3 g, yield; 83%).

To a stirred solution of 1-{2-[(cyclopropylmethyl)oxy]-6-hydroxyphenyl} ethanone (56.3 g, 272 mmol) in acetone (1000 mL) was added potassium carbonate (188 g, 1364 mmol), 4-methoxybenzyl chloride (40.9 mL, 300 mmol) and tetrabutylammonium iodide (20.2 g, 54.6 mmol). The mixture was stirred at reflux overnight. The reaction mixture was allowed to cool to room temperature, filtered on Celite, and then the filtrate was concentrated under reduced pressure. The residue was diluted with water and extracted with ethyl acetate. The separated organic phase was washed with brine, dried over $MgSO_4$, filtered and concentrated under reduced pressure. Then the resulting white solid was recrystallized from ethanol, collected by filtration, washed with ethanol, and dried under reduced pressure to give starting compound 1A' as a white solid (79.2 g, yield; 89%).

Starting Compound 1B: 2'-[tert-butyl(dimethyl)silyl]oxyacetophenone

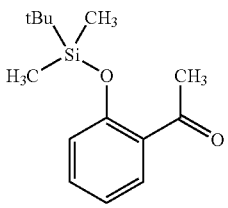

To a stirred solution of 2'-hydroxyacetophenone (10.00 g, 73.45 mmol) in DMF (150 mL) were added imidazole (6.00 g, 88.14 mmol) and tert-butyl dimethylchlorosilane (12.18 g, 80.79 mmol). The mixture was stirred at room temperature for 60 hrs., and then diluted with diethyl ether. The resulting organic phase was washed with water, aqueous potassium hydrogen sulfate solution, and brine, successively. Then the washed organic phase was dried over magnesium sulfate, filtered, and concentrated under reduced pressure. The residue was purified by column chromatography on silica-gel (hexane:ethyl acetate, 9:1-4:1) to give starting compound 1B as a colorless oil (19.83 g, yield 92%).

Starting Compound 1C: 3-Benzyloxypicolinonitrile

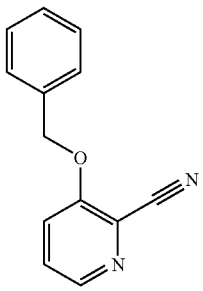

A suspension of 3-hydroxypicolinonitrile (3.00 g, 25.0 mmol), which was prepared according to Synthesis 316

(1983) and J. Org. Chem. 48,1375(1983), potassium carbonate (5.40 g, 39.1 mmol) and benzyl bromide (5.10 g, 29.8 mmol) in acetone (150 mL) was stirred at room temperature for 20 hrs. The reaction mixture was filtrated and the filtrate was evaporated. The residue was purified by column chromatography on silica gel (ethyl acetate:n-hexane=1:3 to 1:2) and recrystallization from ethyl acetate:n-hexane=1:4 to give starting compound 1C as a colorless powder (4.354 g, yield 83%).

Starting Compound 1D:
2-Acetyl-3-benzyloxypyridine

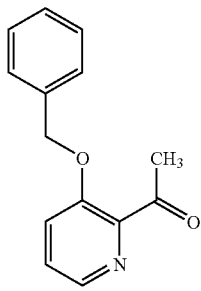

To a cold solution (0° C.) of 3-benzyloxy-picolinonitrile (2.50 g, 11.9 mmol) in tetrahydrofuran (100 mL) was added 0.92M methylmagnesium bromide in tetrahydrofuran (150 mL, 138 mmol) and stirred at 0° C. for 30 minutes then at room temperature for 4 hrs. The reaction mixture was poured into water (2 L) and acidified by 10% sulfuric acid (500 mL). After stirring for 30 minutes, the reaction mixture was added to sodium bicarbonate (100 g) slowly and extracted into ethyl acetate. The resulting organic phase was washed with saturated sodium chloride, dried anhydrous $Na_2SO_4$, filtrated, and evaporated. The residue was purified by column chromatography on silica gel (ethyl acetate:n-hexane, 1:3) to give starting compound 1D as a colorless oil (2.49 g, yield 92%).

Starting Compound 2: 2-amino-4-(3-aminophenyl)-6-(2-{[tert-butyl(dimethyl)silyl]oxy}phenyl)nicotinonitrile

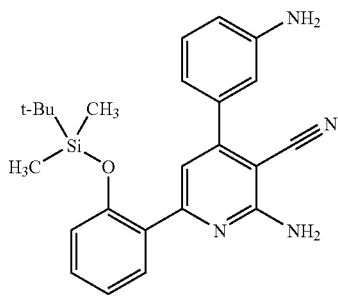

A mixture of 2'-[tert-butyl(dimethyl)silyl]-oxyacetophenone (starting compound 1B, 20.0 g, 79.9 mmol), 3-nitrobenzaldehyde (12.1 g, 79.9 mmol), malononitrile (5.3 g, 79.9 mmol), ammonium acetate (9.2 g, 119.8 mmol) and toluene (25 mL) was stirred under reflux for 3 hrs. The reaction mixture was extracted with ethyl acetate and water. The separated organic phase was dried over $Na_2SO_4$, filtrated, and concentrated under reduced pressure. The crude product was purified by column chromatography on silica gel (hexane/ethyl acetate, 9:1-4:1) to give 2-amino-6-(2-{[tert-butyl(dimethyl)silyl]-oxy}phenyl)-4-(3-nitrophenyl)nicotinonitrile as a white solid (6.5 g, 18%).

A mixture of 2-amino-6-(2-{[tert-butyl(dimethyl)-silyl]oxy}phenyl)-4-(3-nitrophenyl)nicotinonitrile (3.2 g, 7.2 mmol), 10% Pd—C (0.25 g) and ethyl acetate (1 L) was stirred at room temperature for 12 hrs. under a hydrogen atmosphere (2.5 atm). The reaction mixture was filtered on Celite Pad and the filtration was concentrated under reduced pressure to give starting compound 2, which was used for the next step without further purification (2.6 g, yield 87%).

Starting Compound 3: 2-amino-4-[3-amino-4-(1-pyrrolidinyl)phenyl]-6-(2-benzyloxyphenyl)nicotinonitrile

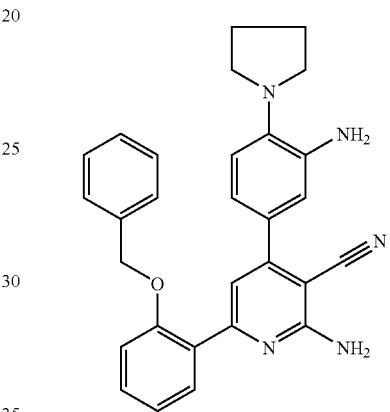

A mixture of 2-benzyloxyacetophenone (5.00 g, 22.10 mmol), 4'-chloro-3'-nitrobenzaldehyde (8.20 g, 44.19 mmol), malononitrile (2.92 g, 44.19 mmol), and ammonium acetate (8.52 g, 110.48 mmol) in toluene (15 mL) was stirred at 130° C. for 3 hrs. After cooled to room temperature, the mixture was diluted with ethyl acetate and THF. The organic phase was washed twice with water, dried over $Na_2SO_4$, filtered, and concentrated under reduced pressure. The residue was suspended in ethanol. The precipitate was collected by filtration, washed with ethyl acetate, and dried under reduced pressure to give 2-amino-6-(2-benzyloxyphenyl)-4-(4-chloro-3-nitrophenyl)nicotinonitrile as a white solid (6.40 g, yield 63%).

To a cold (0° C.) solution of 2-amino-6-(2-benzyloxyphenyl)-4-(4-chloro-3-nitrophenyl)nicotinonitrile (1.000 g, 2.189 mmol) in DMF (10 mL) was added pyrrolidine (0.778 g, 10.943 mmol). The mixture was stirred at room temperature for 2 hrs. and then at 60° C. for 2 hrs. The reaction mixture was partitioned between ethyl acetate and water. The separated organic phase was washed with brine, dried over $Na_2SO_4$, filtered, and concentrated under reduced pressure. The residue was suspended in ethanol, and the precipitate was collected by filtration, washed with ethyl acetate and dried under reduced pressure to give 2-amino-6-(2-benzyloxyphenyl)-4-[3-nitro-4-(1-pyrrolidinyl)phenyl]nicotinonitrile as a yellow solid (0.990 g, yield 92%).

To a suspension of 2-amino-6-(2-(benzyloxy)phenyl)-4-[3-nitro-4-(1-pyrrolidinyl)phenyl]nicotinonitrile (1.000 g, 2.034 mmol) and Fe powder (3.000 g) in ethanol (180 mL) were added water (10 mL) and then ammonium chloride (1.000 g). The mixture was stirred under reflux for 3 hrs. The mixture was filtered on Celite Pad and the filtrate was concentrated under reduced pressure. The residue was suspended in ethanol, and the precipitate was collected by filtration, washed with ethyl acetate, and dried under reduced pressure to give starting compound 3 as a white solid (0.700 g, yield 75%).

Starting Compound 4: 2-amino-4-[3-amino-4-(dimethylamino)phenyl]-6-{2-[(4-methoxybenzyl)oxy]phenyl}nicotinonitrile

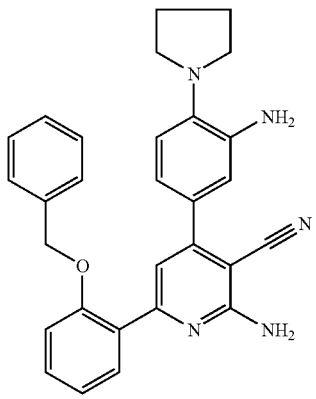

A mixture of 2-(4-methoxybenzyloxy)acetophenone (5.663 g, 22.097 mmol), 4'-chloro-3'-nitrobenzaldehyde (8.201 g, 44.193 mmol), malononitrile (2.920 g, 44.193 mmol), and ammonium acetate (8.516 g, 110.486 mmol) in toluene (15 mL) was stirred at 130° C. for 4 hrs. The reaction mixture was partitioned between ethyl acetate and water. The separated organic phase was washed with brine, dried over Na$_2$SO$_4$, filtered, and concentrated under reduced pressure. The residue was suspended with ethanol. The resulting solid was collected by filtration, washed with ethanol, ethyl acetate and diethyl ether, and dried under reduced pressure to give 2-amino-4-(4-chloro-3-nitrophenyl)-6-{2-[(4-methoxybenzyl)oxy]phenyl}-nicotinonitrile as a white solid (5.560 g, yield 52%).

To a stirred solution of 2-amino-4-(4-chloro-3-nitrophenyl)-6-{2-[(4-methoxybenzyl)oxy]phenyl}-nicotinonitrile (0.850 g, 1.746 mmol) in DMF (5 mL) including triethylamine (1.2 mL) was added dimethylamine hydrochloride (0.996 g, 12.220 mmol), and the mixture was stirred at 70° C. for 3 hrs. The reaction mixture was quenched with water and extracted with ethyl acetate. The organic phase was washed with brine, dried over Na$_2$SO$_4$, filtered, and concentrated under reduced pressure. The residue was suspended in ethanol. The resulting solid was collected by filtration, washed with ethanol, and dried under reduced pressure to give 2-amino-4-[4-(dimethylamino)-3-nitrophenyl]-6-{2-[(4-methoxybenzyl)-oxy]phenyl}nicotinonitrile as an orange oil (0.820 g, yield 95%).

To a stirred suspension of 2-amino-4-[4-(dimethylamino)-3-nitrophenyl]-6-{2-[(4methoxybenzyl) oxy] phenyl}nicotinonitrile (0.815 g, 1.654 mmol) in ethanol (150 mL) were added Fe powder (5.000 g), water (20 mL) and ammonium chloride (1.000 g). The mixture was stirred under reflux for 12 hrs. The reaction mixture was cooled to room temperature, filtered on Celite Pad. The filtrate was concentrated under reduced pressure. The residue was suspended in ethanol. The resulting solid was collected by filtration, washed with ethanol and water, and dried under reduced pressure to give starting compound 4 as an orange solid (0.500 g, yield 65%).

Starting Compound 5: 3-(2-amino-3-cyano-6-{2-[(4-methoxybenzyl)oxy]phenyl}-4-pyridinyl)benzoic acid

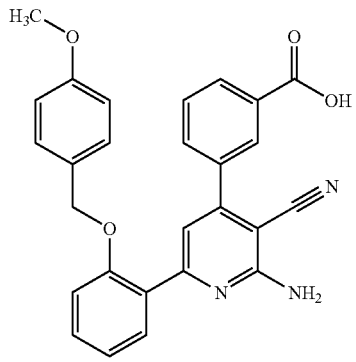

A mixture of 2-{(4-methoxybenzyl)oxy}acetophenone (0.26 g, 1.00 mmol), methyl 3-formbenzoate (0.16 g, 1.00 mmol), malononitrile (0.07 g, 1.00 mmol), and ammonium acetate (0.23 g, 3.00 mmol) in xylene (10 mL) was heated at 120° C. (bath temperature) overnight. The resulting mixture was concentrated under reduced pressure, and the residue was diluted with water and extracted with ethyl acetate. The separated organic phase was washed with brine, dried over MgSO$_4$, filtered, and concentrated under reduced pressure. The crude material was purified by column chromatography on silica gel (hexane:ethyl acetate, 70:30) to give 2-amino-6-{2-[(4-methoxybenzyl)oxy]phenyl}-4-(3-methoxycarbonylphenyl)-nicotinonitrile (0.200 g, yield 43%).

A mixture of 2-amino-6-{2-[(4-methoxybenzyl)-oxy]phenyl}-4-(3-methoxycarbonylphenyl)-nicotinonitrile (0.20 g, 0.43 mmol), 4N NaOH solution (1.0 mL), and THF (5.0 mL) was stirred at room temperature overnight. The reaction mixture was poured into water and extracted with ethyl ether twice. To the separated aqueous phase was added 1N KHSO$_4$ solution until the mixture became acidic. The resulting precipitate was collected by filtration and dried under reduced pressure to give the stating compound 5 as a gray powder (0.16 g, yield 81%).

Starting Compound 6: tert-butyl 2-amino-4-(3-aminophenyl)-6-(2-hydroxyphenyl)nicotinate

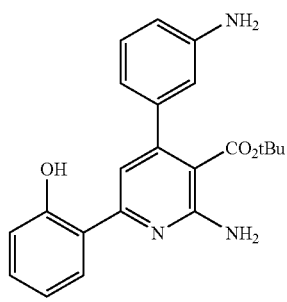

A mixture of 2'-benzyloxyacetophenone (3.00 g, 13.25 mmol), 3'-nitrobenzaldehyde (2.00 g, 13.25 mmol), tert-butyl cyanoacetate (1.87 g, 13.25 mmol), ammonium acetate (3.07 g, 39.77 mmol) in p-xylene (10 mL) was stirred at 120° C. for 2 hrs. After cooled to room temperature, the reaction mixture was partitioned between ethyl acetate and water. The separated organic phase was washed with brine, dried over $Na_2SO_4$, filtrated, and concentrated under reduced pressure. The crude product was purified by column chromatography on silica-gel (hexane:ethyl acetate, 5:1-2:1) to give tert-butyl 2-amino-6-[2-(benzyloxy)phenyl]-4-(3-nitrophenyl)nicotinate as a yellow oil (2.51 g, yield 38%).

A mixture of tert-butyl 2-amino-6-[2-(benzyloxy)-phenyl]-4-(3-nitrophenyl)nicotinate (2.50 g, 5.02 mmol) and 10% Pd—C (0.20 g) in ethyl acetate (20 mL) was stirred at 2 atm under a hydrogen atmosphere for 5 hrs. The mixture was filtered on Celite Pad to remove Pd—C and washed with ethyl acetate. The filtrate was concentrated under reduced pressure, and the residue was purified by column chromatography on silica-gel (hexane:ethyl acetate, 4:1-3:2) to give starting compound 6 as a pale yellow oil (1.05 g, yield 56%).

Example 1-1

N-{3-[2-amino-3-cyano-6-(2-hydroxyphenyl)-4-pyridinyl]phenyl}-5-oxotetrahydro-2-furancarboxamide

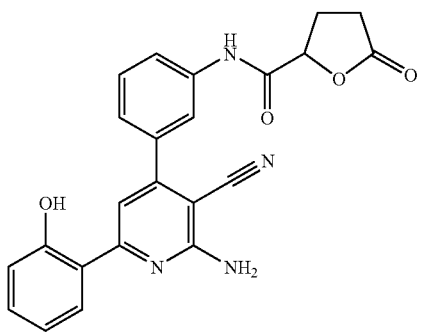

To a cold (0° C.) mixture of pyridine (0.20 mL, 2.424 mmol), 2-amino-4-(3-aminophenyl)-6-(2-{[tert-butyl(dimethyl)silyl]oxy}phenyl)nicotinonitrile (starting compound 2, 1.010 g, 2.424 mmol), acetonitrile (10 mL) and THF (2 mL) was added dropwise a solution of 5-oxotetrahydro-2-furancarbonyl chloride (0.360 g, 2.424 mmol) in acetonitrile (4 mL). The mixture was stirred for 2 hrs., allowed to warm to room temperature, stirred for 1 hr., and extracted with ethyl acetate and water. The separated organic phase was washed with brine, dried over $Na_2SO_4$, filtered and concentrated under reduced pressure. The residue was purified by column chromatography on silica-gel (hexane:Ethyl acetate, 7:3-5:5) to give N-{3-[2-amino-6-(2-{[tert-butyl(dimethyl)silyl]oxy}phenyl)-3-cyano-4-pyridinyl]phenyl}-5-oxotetrahydro-2-furancarboxamide as a white solid (0.982 g, yield 77%).

To a cold (0° C.) solution of N-{3-[2-amino-6-(2-{[tert-butyl(dimethyl)silyl]oxy}phenyl)-3-cyano-4-pyridinyl]phenyl}-5-oxotetrahydro-2-furancarboxamide (0.400 g, 0.757 mmol) in THF (5 mL) was added dropwise a solution n-tetrabutylammonium fluoride in THF (1M, 2 mL). After being stirred for 30 minutes, the mixture was quenched with water (5 mL). The resulting precipitate was collected by filtration, washed with water and ethanol, and dried under reduced pressure to give N-{3-[2-amino-3-cyano-6-(2-hydroxyphenyl)-4-pyridinyl]phenyl}-5-oxotetrahydro-2-furancarboxamide as a white solid (0.293 g, yield 93%).

Molecular weight: 414.424

Mass spectrometry: 415

Melting point: 155 dec

In vitro activity grade: B

Cellular activity grade: (A954)-B $^1$H-NMR (300 MHz, DMSO-d6): 2.23-2.38 (2H, m), 2.55-2.59 (2H, m), 5.08-5.12 (1H, m), 6.87-6.93 (2H, m), 7.32-7.47 (4H, m), 7.50-7.56 (2H, m), 7.82 (1H, d, J=8.3 Hz), 7.91 (1H, s), 8.02 (1H, d, J=8.0 Hz), 10.47 (1H, s).

Example 1-2

Sodium 5-({3-[2-amino-3-cyano-6-(2-hydroxyphenyl)-4-pyridinyl]phenyl}amino)-4-hydroxy-5-oxopentanoate

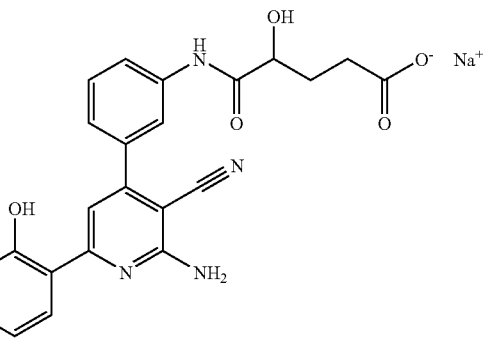

To a suspension of N-{3-[2-amino-3-cyano-6-(2-hydroxyphenyl)-4-pyridinyl]phenyl}-5-oxotetrahydro-2-furancarboxamide (0.250 g, 0.603 mmol) in methanol (10 mL) was added dropwise 2N NaOH solution (0.3 mL). After the mixture was stirred for 10 minutes, insoluble solid was filtered off. The filtrate was concentrated under reduced pressure and the residue was crystallized from methanol and ethyl ether. The resulting solid was collected by filtration under an argon atmosphere, washed with ethyl ether, and dried under reduced pressure to give Sodium 5-({3-[2-amino-3-cyano-6-(2-hydroxyphenyl)-4-pyridinyl]phenyl}amino)-4-hydroxy-5-oxopentanoate as a pale yellow solid (0.165 g, yield 60%).

Molecular weight: 454.421

Mass spectrometry: 433

Melting point: 199 dec

In vitro activity grade: B

Cellular activity grade: (A954)-C $^1$H-NMR (300 MHz, DMSO-d6): 1.72-1.98 (2H, m), 2.18-2.25 (2H, m), 4.01 (1H, dd, J=3.2, 7.5 Hz), 6.60-6.85 (2H, m), 7.09-7.30 (3H, m), 7.32 (1H, d, J=7.9 Hz), 7.46 (1H, t, J=7.9 Hz), 7.67 (1H, br), 7.93 (1H, d, J=8.2 Hz), 8.01-8.05 (2H, m), 9.91 (1H, s), 10.38 (1H, br s).

Examples 1-03 to 1-23

In the similar manners as described in Example 1-01 and Example 1-02 above, compounds in Examples 1-03 to 1-23 as shown in Table 1 were synthesized.

TABLE 1
| EX No | STRUCTURE | mol weight | MS | A549 | invitro |
|---|---|---|---|---|---|
| 1-03 | 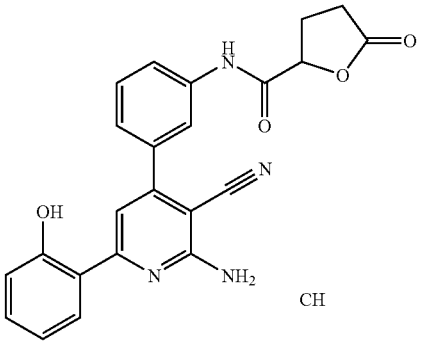 | 450,885 | 415 | C | B |
| 1-04 | 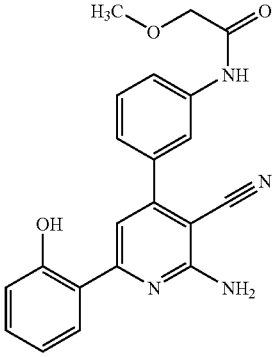 | 374,403 | 375 | C | B |
| 1-05 | 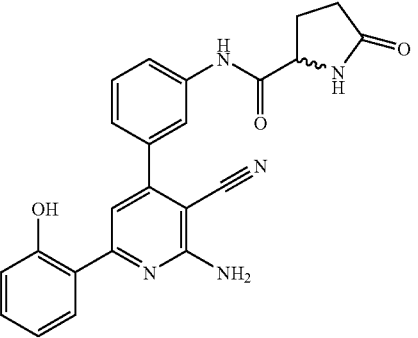 | 413,440 | 414 | C | C |
| 1-06 | 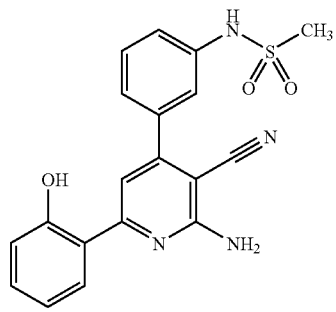 | 380,428 | 381 | B | C |

TABLE 1-continued
| EX No | STRUCTURE | mol weight | MS | A549 | invitro |
|---|---|---|---|---|---|
| 1-07 | 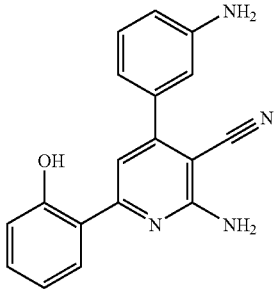 | 375,260 | 303 | C | C |
| 1-08 | 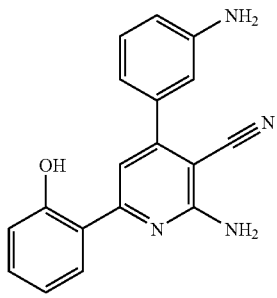 | 302,338 | 303 | C | D |
| 1-09 | 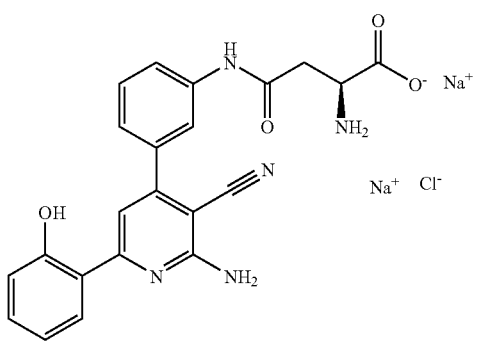 | 497,852 | 418 | C | A |
| 1-10 | 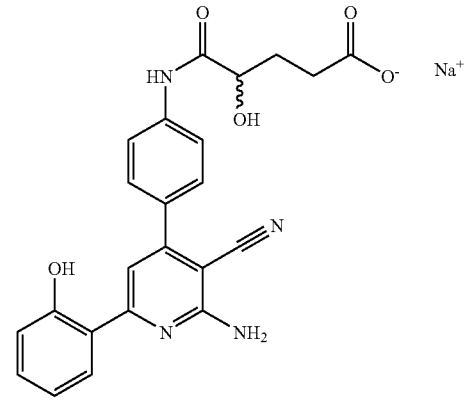 | 454,421 | 432 | C | A |

TABLE 1-continued
| EX No | STRUCTURE | mol weight | MS | A549 | invitro |
|---|---|---|---|---|---|
| 1-11 | 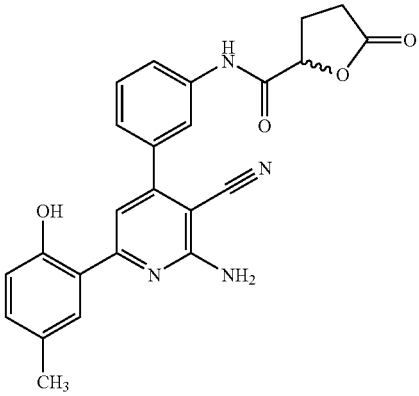 | 428,451 | 429 | C | D |
| 1-12 | 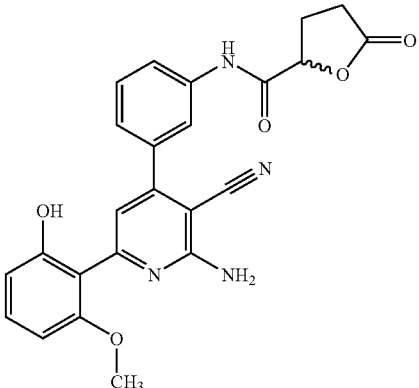 | 444,451 | 445 | C | B |
| 1-13 | 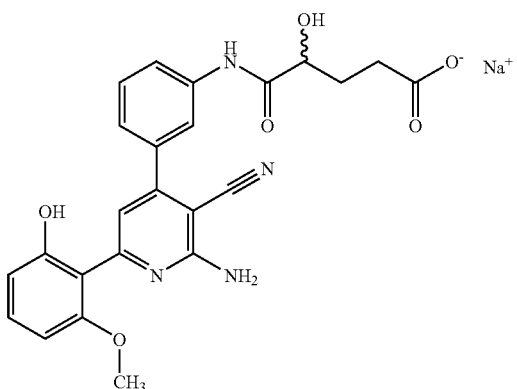 | 484,448 | 463 | C | B |
| 1-14 | 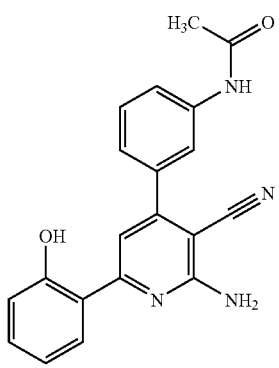 | 344,376 | 345 | C | D |

TABLE 1-continued

| EX No | STRUCTURE | mol weight | MS | A549 | invitro |
|---|---|---|---|---|---|
| 1-15 | 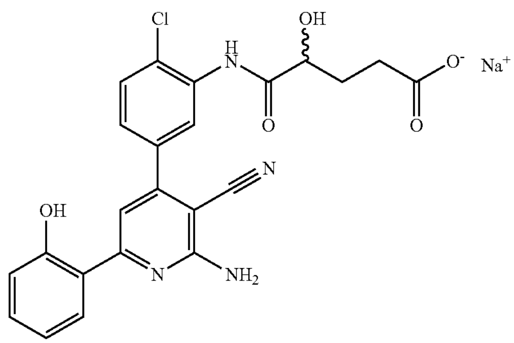 | 488.867 | 467 | C | A |
| 1-16 | 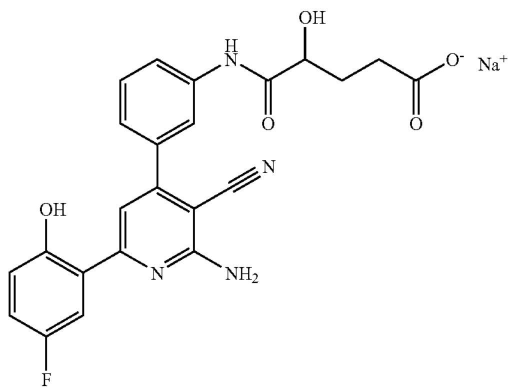 | 472.412 | 451 | C | B |
| 1-17 | 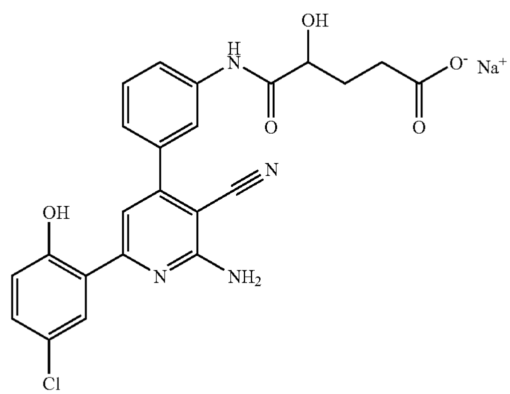 | 488.867 | 467 | C | C |
| 1-18 | 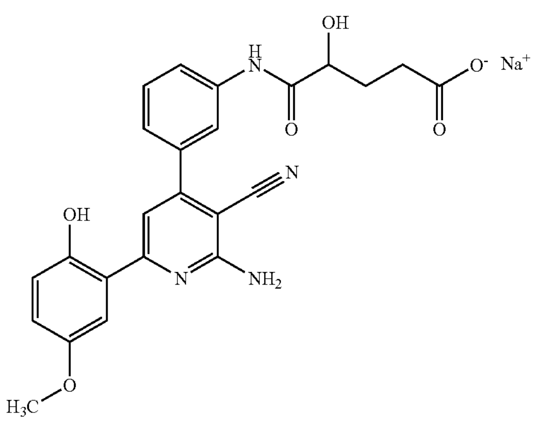 | 484.448 | 463 | C | C |

TABLE 1-continued
| EX No | STRUCTURE | mol weight | MS | A549 | invitro |
|---|---|---|---|---|---|
| 1-19 | 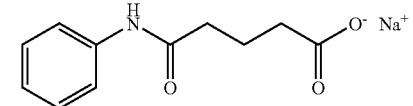 | 438,422 | 417 | C | B |
| 1-20 | 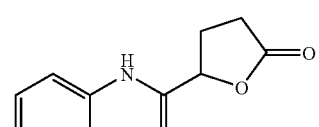 | 415,412 | 416 | C | C |
| 1-21 | 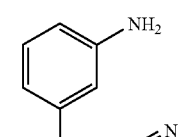 | 303,326 | 304 | B | C |
| 1-22 | 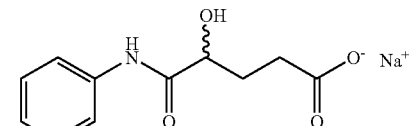 | 455,409 | 434 | C | B |

TABLE 1-continued

| EX No | STRUCTURE | mol weight | MS | A549 | invitro |
|---|---|---|---|---|---|
| 1-23 | | 417,347 | 304 | B | A |

Example 2-1

N-{3-[2-amino-3-cyano-6-(2-hydroxyphenyl)-4-pyridinyl]phenyl}-3-(1-piperidinyl)propanamide hydrochloride

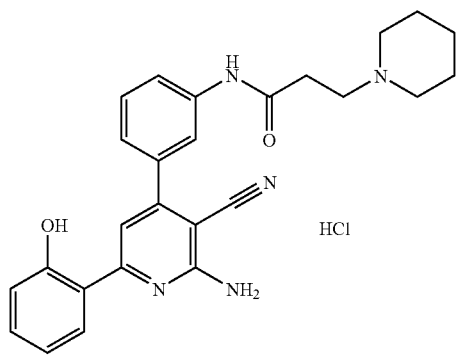

To a cold (0° C.) solution of 3-(1-piperidinyl)-propanoic acid (0.676 g, 3.601 mmol) in dichloromethane was added oxalyl chloride (0.471 mL, 5.401 mmol) and stirred at room temperature for 12 hrs. The mixture was concentrated under reduced pressure. The residue was added to the solution of 2-amino-4-(3-aminophenyl)-6-(2-{[tert-butyl(dimethyl)silyl]oxy}-phenyl)nicotinonitrile (starting compound 2, 1.500 g, 3.601 mmol) in acetonitrile (3 mL), and the resulting mixture was stirred at 0° C. for 1 hr. The reaction mixture was extracted with ethyl acetate and water. The separated organic phase was washed with brine, dried over $Na_2SO_4$, filtered and concentrated under reduced pressure. Purification was carried out by silica gel column chromatography (chloroform/methanol=10/1) to give N-{3-[2-amino-6-(2-{[tert-butyl(dimethyl)silyl]oxy}phenyl)-3-cyano-4-pyridinyl]phenyl}-3-(1-piperidinyl)propanamide as a white solid (0.860 g, yield 45%).

To a stirred solution of N-{3-[2-amino-6-(2-{[tert-butyl(dimethyl)silyl]oxy}phenyl)-3-cyano-4-pyridinyl]-phenyl}-3-(1-piperidinyl)propanamide (0.150 g, 0.270 mmol) in 1,4-dioxane (5 mL) was added 4N HCl in dioxane (2 mL). The mixture was stirred at room temperature for 12 hrs. The resulting precipitate was collected by filtration, washed with ethanol, and dried under reduced pressure to give N-{3-[2-amino-3-cyano-6-(2-hydroxyphenyl)-4-pyridinyl]phenyl}-3-(1-piperidinyl)propanamide hydrochloride (0.011 g, yield 9%).

Molecular weight: 477.998
Mass spectrometry: 442
In vitro activity grade: B
Cellular activity grade: (A954)-B
$^1$H-NMR (300 MHz, DMSO-d6): 1.38-1.50 (1H, m), 1.71-1.84 (5H, m), 2.76-3.04 (4H, m), 3.35-3.51 (4H, m), 6.90-6.98 (2H, m), 7.38-7.41 (3H, m), 7.54 (1H, t, J=7.9 Hz), 7.83 (1H, d, J=8.2 Hz), 7.95 (1H, s), 8.06 (1H, dd, J=1.3, 8.2Hz), 10.42 (1H, brs), 10.64 (1H, brs).

Examples 2-02 to 2-19

In the similar manners as described in Example 2-01 above, the compounds in Examples 2-02 to 2-19 as shown in Table 2 were synthesized.

TABLE 2

| EX No | STRUCTURE | mol weight | MS | A549 | invitro |
|---|---|---|---|---|---|
| 2-02 | 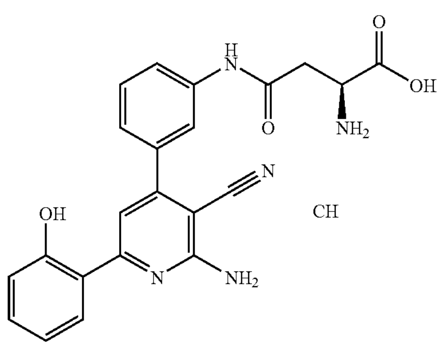 | 453,889 | 418 | C | B |

TABLE 2-continued
| EX No | STRUCTURE | mol weight | MS | A549 | invitro |
|---|---|---|---|---|---|
| 2-03 | 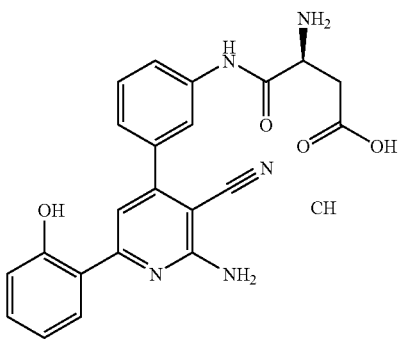 | 453,889 | 418 | C | B |
| 2-04 | 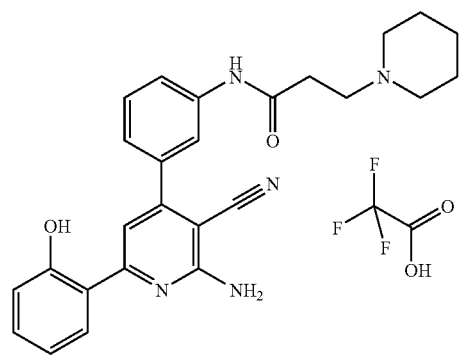 | 555,562 | 442 | B | B |
| 2-05 | 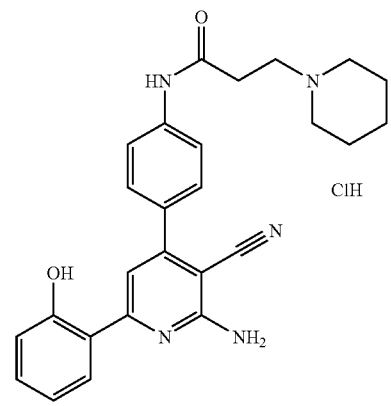 | 477,998 | 442 | C | B |
| 2-06 | 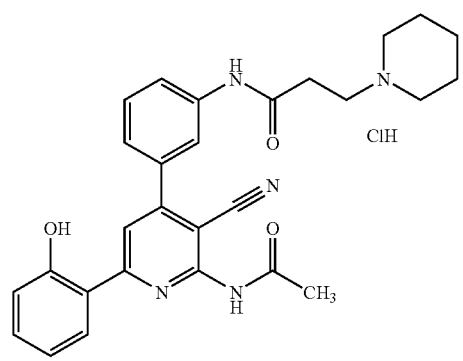 | 520,036 | 484 | C | D |

TABLE 2-continued
| EX No | STRUCTURE | mol weight | MS | A549 | invitro |
|---|---|---|---|---|---|
| 2-07 | 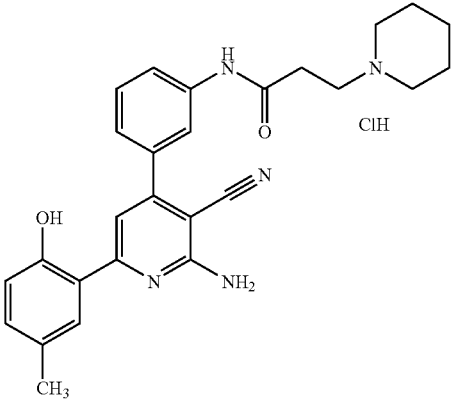 | 492,025 | 456 | C | C |
| 2-08 | 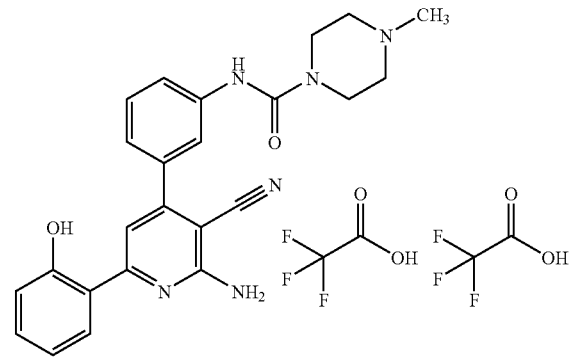 | 656,546 | 429 | B | C |
| 2-09 | 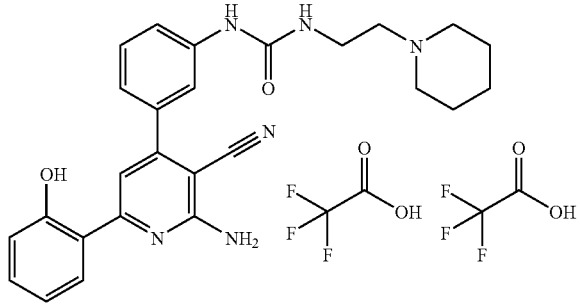 | 684,601 | 457 | B | B |
| 2-10 | 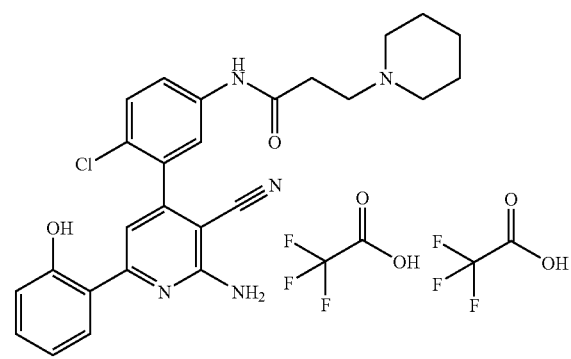 | 704,031 | 476 | B | B |

TABLE 2-continued
| EX No | STRUCTURE | mol weight | MS | A549 | invitro |
|---|---|---|---|---|---|
| 2-11 | 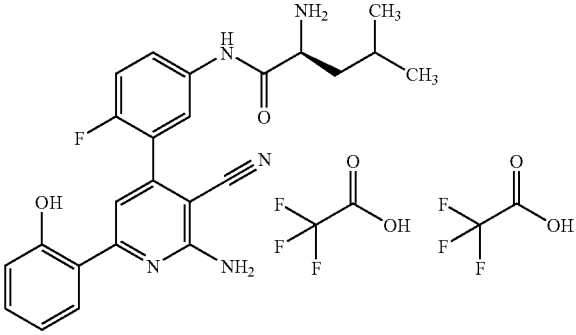 | 661,538 | 434 | B | B |
| 2-12 | 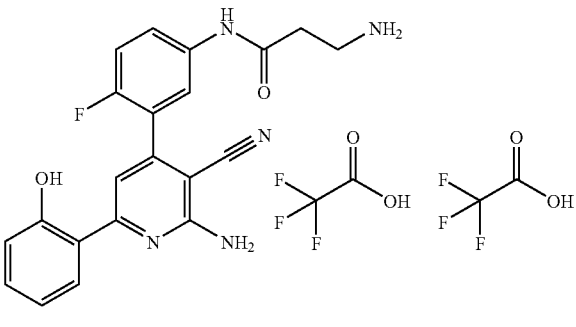 | 619,457 | 392 | C | C |
| 2-13 | 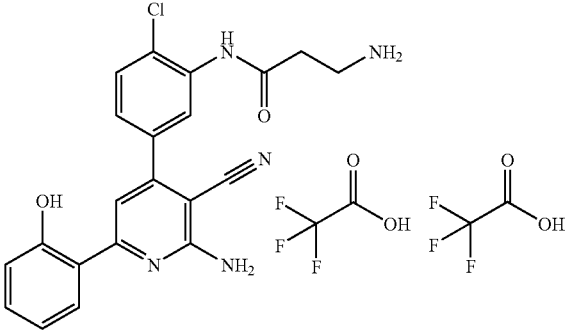 | 635,911 | 408 | B | A |
| 2-14 | 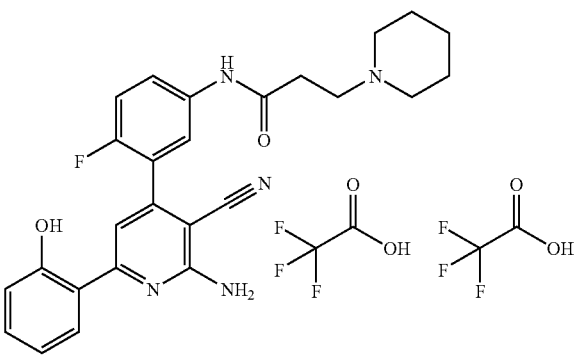 | 687,576 | 460 | B | B |

TABLE 2-continued

| EX No | STRUCTURE | mol weight | MS | A549 | invitro |
|---|---|---|---|---|---|
| 2-15 | 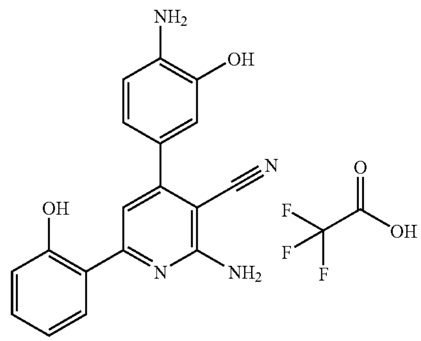 | 432,362 | 319 | B | A |
| 2-16 | 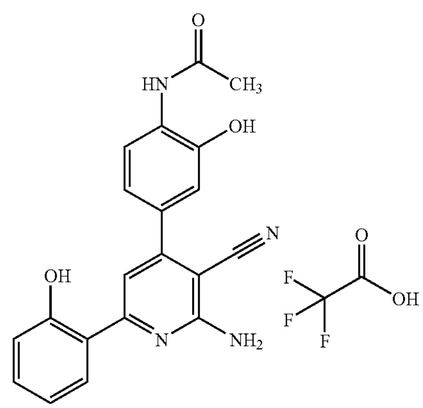 | 474,400 | 361 | B | A |
| 2-17 | 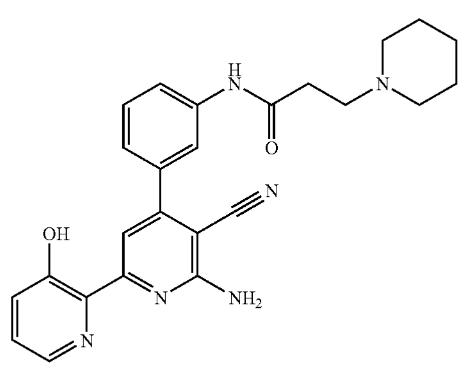 | 442,525 | 443 | C | B |
| 2-18 | 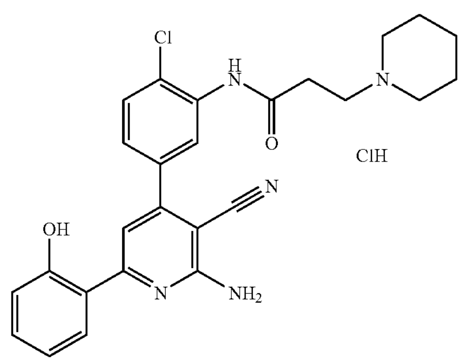 | 512,443 | 476 | C | B |

TABLE 2-continued

| EX No | STRUCTURE | mol weight | MS | A549 | invitro |
|---|---|---|---|---|---|
| 2-19 | 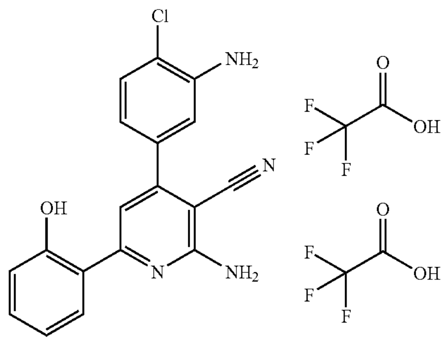 | 564,832 | 337 | B | D |

Example 3-1

N-[5-[2-amino-3-cyano-6-(2-hydroxyphenyl)-4-pyridinyl]-2-(1-pyrrolidinyl)phenyl]-3-(1-piperidinyl) propanamide hydrochloride

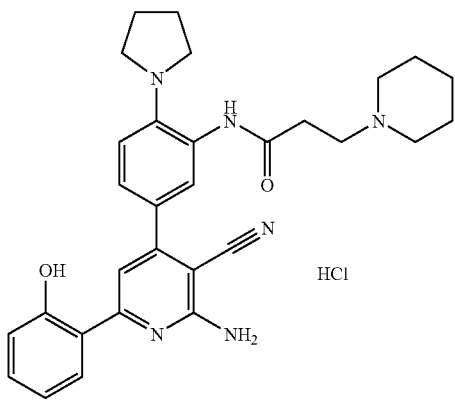

To a stirred solution of 2-amino-4-[3-amino-4-(1-pyrrolidinyl)phenyl]-6-[2-(benzyloxyphenyl)]nicotinonitrile (starting compound 3, 0.166 g, 0.360 mmol) in pyridine (3 mL) was added 3-(1-piperidinyl)propanoyl chloride hydrochloride (0.153 g, 0.719 mmol) at room temperature and the stirring was continued for 3 hrs. The reaction mixture was extracted with ethyl acetate and water. The separated organic phase was washed with brine, dried over $Na_2SO_4$, filtered, and concentrated under reduced pressure. The residue was suspended in ethyl acetate and ethanol, and then the precipitate was collected by filtration, washed with ethanol, and dried under reduced pressure to give N-[5-[2-amino-6-(2-benzyloxyphenyl)-3-cyano-4-pyridinyl]-2-(1-pyrrolidinyl)phenyl]-3-(1-piperidinyl)propanamide as a white solid (0.070 g, yield 32%).

A mixture of N-[5-[2-amino-6-(2-benzyloxyphenyl)-3-cyano-4-pyridinyl]-2-(1-pyrrolidinyl)phenyl]-3-(1-piperidinyl)propanamide (0.140 g, 0.233 mmol), 100% Pd—C (0.150 g), ethyl acetate, and acetic acid (2.000 mL) was stirred at room temperature under a hydrogen atmosphere for 12 hrs. The reaction mixture was filtered on Celite Pad and the filtrate was concentrated under reduced pressure. The residue was dissolved in THF (3 mL) and 4N HCl in 1,4-dioxane (0.5 mL) was added to the solution. The resulting yellow solid was collected by filtration, washed with THF, and dried under reduced pressure to give N-[5-[2-amino-3-cyano-6-(2-hydroxyphenyl)-4-pyridinyl]-2-(1-pyrrolidinyl)phenyl]-3-(1-piperidinyl)propanamide hydrochloride (0.110 g, yield 86%).

Molecular weight: 547.105
Mass spectrometry: 511
Melting point: 152
In vitro activity grade: B
Cellular activity grade: (A954)-B $^1$H-NMR (300 MHz, DMSO-d6): 1.35-1.40 (1H, m), 1.67-1.80 (6H, m), 1.92 (4H, s), 2.89-2.98 (4H, m), 3.29-3.57 (8H, m), 3.58-3.60 (1H, m), 6.87-6.95 (2H, m), 7.02 (1H, d, J=7.9 Hz), 7.30-7.37 (3H, m), 7.53-7.56 (2H, m), 7.98 (2H, d, J=7.2 Hz), 9.85 (1H, s), 10.45 (1H, brs).

Examples 3-02 to 3-17

In the similar manners as described in Example 3-01 above, the compounds in Examples 3-02 to 3-17 as shown in Table 3 were synthesized.

TABLE 3

| EX No | MOLSTRUCTURE | mol weight | MS | A549 | invitro |
|---|---|---|---|---|---|
| 3-02 | | 685,588 | 458 | B | A |
| 3-03 | | 684,601 | 457 | B | A |
| 3-04 | | 670,574 | 443 | B | A |

TABLE 3-continued

| EX No | MOLSTRUCTURE | mol weight | MS | A549 | invitro |
|---|---|---|---|---|---|
| 3-05 | | 688,589 | 461 | B | B |
| 3-06 | | 686,573 | 459 | B | B |
| 3-07 | | 644,535 | 417 | B | A |
| 3-08 | | 712,655 | 485 | B | A |

| EX No | MOLSTRUCTURE | mol weight | MS | A549 | invitro |
|---|---|---|---|---|---|
| 3-09 | | 712.655 | 485 | B | C |
| 3-10 | | 752.720 | 525 | B | C |
| 3-11 | | 742.681 | 515 | B | B |
| 3-12 | | 768.720 | 541 | B | B |

TABLE 3-continued

| EX No | MOLSTRUCTURE | mol weight | MS | A549 | invitro |
|---|---|---|---|---|---|
| 3-13 | | 740.709 | 513 | B | C |
| 3-14 | | 753.708 | 526 | B | A |
| 3-15 | | 762.715 | 535 | B | C |

TABLE 3-continued

| EX No | MOLSTRUCTURE | mol weight | MS | A549 | invitro |
|---|---|---|---|---|---|
| 3-16 | | 823,678 | 596 | B | A |
| 3-17 | | 849,717 | 622 | B | A |

Example 4-1

N$^1$-[5-[2-amino-3-cyano-6-(2-hydroxyphenyl)-4-pyridinyl]-2-(dimethylamino)phenyl]-N$^2$-(cyclopropylmethyl)glycinamide hydrochloride

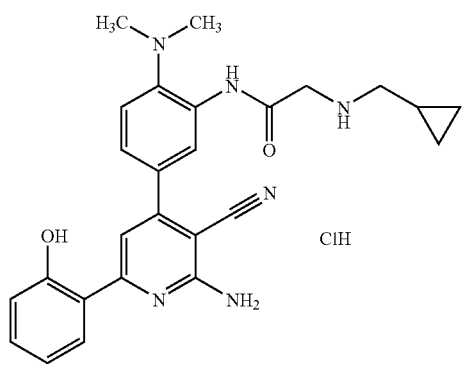

To a cooled (0° C.), stirred solution of 2-amino-4-[3-amino-4-(dimethylamino)phenyl]-6-{2-[(4-methoxybenzyl)-oxy]phenyl}nicotinonitrile (starting compound 4, 0.500 g, 1.724 mmol) in THF (7 mL) under an argon atmosphere was added chloroacetyl chloride (0.121 g, 1.074 mmol). The mixture was stirred at 0° C. for 15 minutes and then partitioned between ethyl acetate and saturated aqueous NaHCO$_3$. The separated organic phase was washed with brine, dried over Na$_2$SO$_4$, filtered, and concentrated under reduced pressure. The residue was suspended in ethyl acetate and ethanol. The resulting solid was collected by filtration, washed with ethanol, and dried under reduced pressure to give N-[5-(2-amino-3-cyano-6-{2-[(4-methoxybenzyl)oxy]-phenyl}-4-pyridinyl)-2-(dimethylamino)phenyl]-2-chloroacetamide as a yellow solid. (0.410 g, yield 70%)

To a stirred solution of N-[5-(2-amino-3-cyano-6-{2-[(4-methoxybenzyl)oxy]phenyl}-4-pyridinyl)-2-(dimethylamino)phenyl]-2-chloroacetamide (0.400 g, 0.738 mmol) in DMF (5 mL) was added aminomethylcyclopropane (0.192 mL, 2.214 mmol). The mixture was stirred at 60° C. for 2 hrs. After cooled to room temperature, the mixture was extracted with ethyl acetate and water. The separated organic phase was washed with brine, dried over Na$_2$SO$_4$, filtered and concentrated under reduced pressure. Purification was carried out by column chromatography on silica gel (chloroform:methanol=100:2, hexane:ethyl acetate=1:2-1:3-1:5, 2 times) to give N$^1$-[5-(2-amino-3-cyano-6-{2-[(4-methoxybenzyl)oxy]phenyl}-4-pyridinyl)-2-(dimethylamino)phenyl]-N$^2$-(cyclopropylmethyl)-glycinamide as a yellow oil (0.130 g, yield 30%).

To a suspension of N$^1$-[5-(2-amino-3-cyano-6-{2-[(4-methoxybenzyl)oxy]phenyl}-4-pyridinyl)-2-(dimethylamino)-phenyl]-N$^2$-(cyclopropylmethyl)glycinamide (0.130 g, 0.448 mmol) in anisole (1 mL) and water (1 mL) was added trifluoroacetic acid (5 mL). The mixture was stirred at room temperature for 20 hrs. The reaction mixture was diluted with toluene and concentrated under reduced pressure. The residue was suspended in hexane and the precipitate was collected by filtration. The solid obtained was dissolved in TB and 4N HCl in 1,4-dioxane was added to the solution. The resulting solid was collected by filtration, washed with THF and 1,4-dioxane, and dried under reduced pressure to give N$^1$-[5-[2-amino-3-cyano-6-(2-hydroxyphenyl)-4-pyridinyl]-2-(dimethylamino)phenyl]-N$^2$-(cyclopropylmethyl) glycinamide hydrochloride as a yellow solid (0.085 g, yield 77%).

Molecular weight: 493.013
Mass spectrometry: 457
In vitro activity grade: B
Cellular activity grade: (A954)-B
$^1$H-NMR (300 MHz, DMSO-d6): 0.35-0.40 (2H, m), 0.57-0.63 (2H, m), 1.05-1.08 (1H, m), 2.80 (6H, s), 2.87-2.91 (2H, m), 4.66-4.68 (2H, m), 6.87-6.94 (2H, m), 7.33-7.40 (4H, m), 7.52-7.55 (1H, m), 7.98 (1H, d, J=7.2 Hz), 8.09 (1H, s), 9.12 (1H, brs), 10.07 (1H, brs).

Examples 4-02 to 4-39

In the similar manners as described in Example 4-01 above, the compounds in Examples 4-02 to 4-39 as shown in Table 4 were synthesized.

TABLE 4

| EX No | MOLSTRUCTURE | mol weight | MS | A549 | invitro |
|---|---|---|---|---|---|
| 4-02 | | 670,574 | 443 | B | B |
| 4-03 | | 636,593 | 523 | B | C |
| 4-04 | | 738,693 | 511 | B | B |

TABLE 4-continued

| EX No | MOLSTRUCTURE | mol weight | MS | A549 | invitro |
|---|---|---|---|---|---|
| 4-05 | | 584,560 | 471 | C | C |
| 4-06 | | 684,601 | 457 | B | B |
| 4-07 | | 656,546 | 429 | B | B |
| 4-08 | | 700,600 | 473 | B | B |

TABLE 4-continued

| EX No | MOLSTRUCTURE | mol weight | MS | A549 | invitro |
|---|---|---|---|---|---|
| 4-09 | | 818,736 | 577 | B | C |
| 4-10 | | 684,601 | 457 | B | B |
| 4-11 | | 760,699 | 533 | B | C |
| 4-12 | | 698,628 | 471 | B | B |

TABLE 4-continued
| EX No | MOLSTRUCTURE | mol weight | MS | A549 | invitro |
|---|---|---|---|---|---|
| 4-13 | 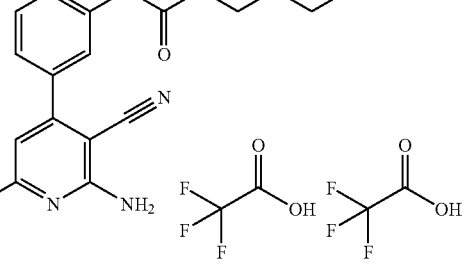 | 714,627 | 487 | B | B |
| 4-14 | 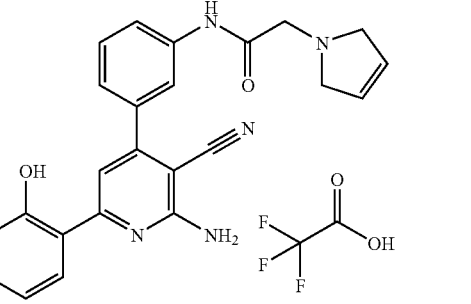 | 525,492 | 412 | B | B |
| 4-15 | 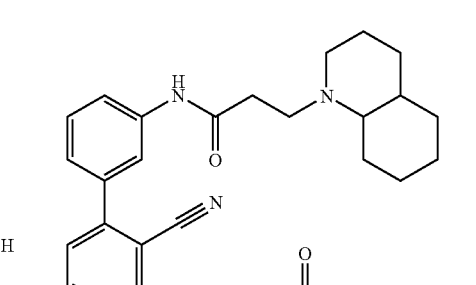 | 609,654 | 496 | B | B |
| 4-16 | 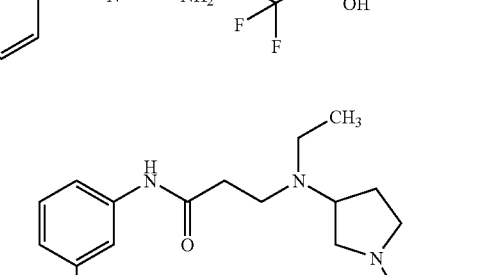 | 726,682 | 499 | B | B |

TABLE 4-continued

| EX No | MOLSTRUCTURE | mol weight | MS | A549 | invitro |
|---|---|---|---|---|---|
| 4-17 | | 655,559 | 428 | B | B |
| 4-18 | | 641,532 | 414 | B | A |
| 4-19 | | 629,521 | 402 | B | B |
| 4-20 | | 645,520 | 418 | C | A |

TABLE 4-continued
| EX No | MOLSTRUCTURE | mol weight | MS | A549 | invitro |
|---|---|---|---|---|---|
| 4-21 | 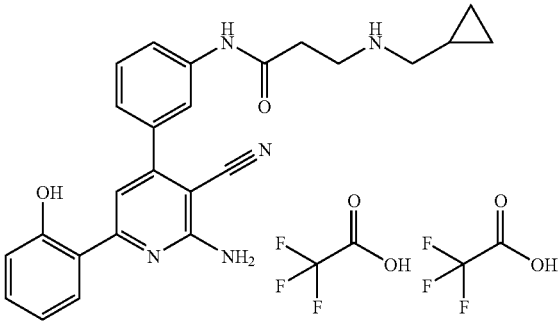 | 655,559 | 428 | B | B |
| 4-22 | 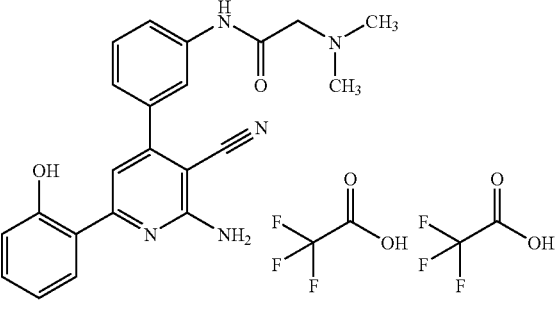 | 615,494 | 388 | B | B |
| 4-23 | 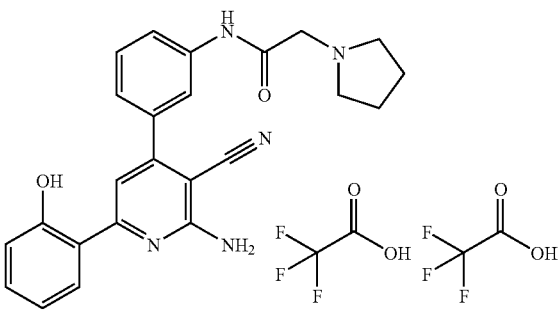 | 641,532 | 414 | B | B |
| 4-24 | 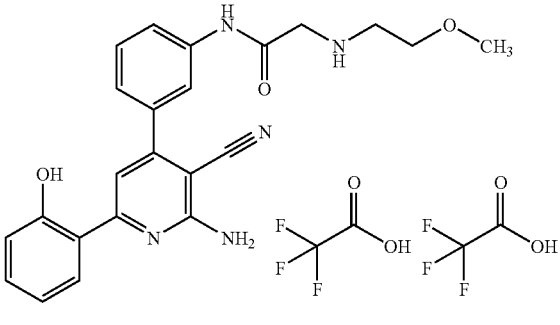 | 645,520 | 418 | C | B |

TABLE 4-continued

| EX No | MOLSTRUCTURE | mol weight | MS | A549 | invitro |
|---|---|---|---|---|---|
| 4-25 | | 679,965 | 452 | C | A |
| 4-26 | | 741,650 | 514 | C | B |
| 4-27 | | 741,650 | 514 | B | C |
| 4-28 | | 507,529 | 486 | C | C |

TABLE 4-continued

| EX No | MOLSTRUCTURE | mol weight | MS | A549 | invitro |
|---|---|---|---|---|---|
| 4-29 | | 507,529 | 486 | C | B |
| 4-30 | | 484,389 | 448 | C | B |
| 4-31 | | 488,377 | 452 | C | A |
| 4-32 | | 715,612 | 488 | B | C |

TABLE 4-continued

| EX No | MOLSTRUCTURE | mol weight | MS | A549 | invitro |
|---|---|---|---|---|---|
| 4-33 | | 713,640 | 486 | C | D |
| 4-34 | | 711,624 | 484 | B | D |
| 4-35 | | 725,651 | 498 | C | D |
| 4-36 | | 521,067 | 485 | B | B |

TABLE 4-continued

| EX No | MOLSTRUCTURE | mol weight | MS | A549 | invitro |
|---|---|---|---|---|---|
| 4-37 | | 825,651 | 598 | B | A |
| 4-38 | | 821,662 | 594 | B | A |
| 4-39 | | 388,473 | 389 | | C |

Example 5-1

Sodium 3-[2-amino-3-cyano-6-(2-hydroxyphenyl)-4-pyridinyl]benzoate

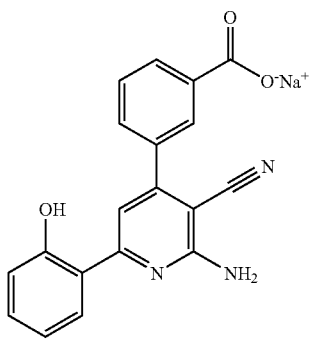

A mixture of 3-(2-amino-3-cyano-6-{2-[(4-methoxybenzyl)oxy]phenyl}-4-pyridinyl)benzoic acid (starting compound 5, 0.16 g, 0.36 mmol), trifluoroacetic acid (3.0 mL), anisole (0.50 mL), and water (0.50 mL) was stirred at room temperature overnight. The reaction mixture was diluted with toluene and concentrated under reduced pressure. The residue was dissolved in THF and then crystallized with hexane. The resulting precipitate was collected by filtration and washed with hexane, and then dried under reduced pressure to give 2-amino-6-(2-hydroxyphenyl)-4-(3-hydroxycarbonylphenyl)nicotinonitrile (0.12 g, yield 74%).

2-amino-6-(2-hydroxyphenyl)-4-(3-hydroxycarbonylphenyl)nicotinonitrile (0.02 g, 0.045 mmol) was dissolved in 4N NaOH solution (2 mL), and the resulting solution was purified by HPLC (ODS reverse phase column, 10% $CH_3CN/H_2O$-90% $CH_3CN/H_2O$) to give Sodium 3-[2-amino-3-cyano-6-(2-hydroxyphenyl)-4-pyridinyl]benzoate as a pale yellow powder (0.015 g, 95%).

Molecular weight: 353.316
Mass spectrometry: 332
Melting point: >270
In vitro activity grade: C
Cellular activity grade: (A954)-C
$^1$H-NMR (300 MHz, DMSO-d6): 6.85-6.93 (2H, m), 7.31-7.56 (5H, m), 7.58 (1H, d, J=3.0 Hz), 7.99-8.06 (2H, m), 8.10 (1H, s), 13.40 (1H, br s).

Examples 5-02 to 5-05

In the similar manners as described in Example 5-01 above, the compounds in Examples 5-02 to 5-05 as shown in Table 5 were synthesized.

TABLE 5

| EX No | MOLSTRUCTURE | mol weight | MS | A549 | invitro |
|---|---|---|---|---|---|
| 5-02 | (structure) | 445,358 | 332 | C | B |
| 5-03 | (structure) | 353,316 | 332 | C | B |

TABLE 5-continued

| EX No | MOLSTRUCTURE | mol weight | MS | A549 | invitro |
|---|---|---|---|---|---|
| 5-04 | | 445,358 | 332 | C | C |
| 5-05 | | 353,316 | 332 | C | B |

Example 6-1

3-[2-amino-3-cyano-6-(2-hydroxyphenyl)-4-pyridinyl]-N-[2-(1-piperidinyl)ethyl]benzamide trifluoroacetate

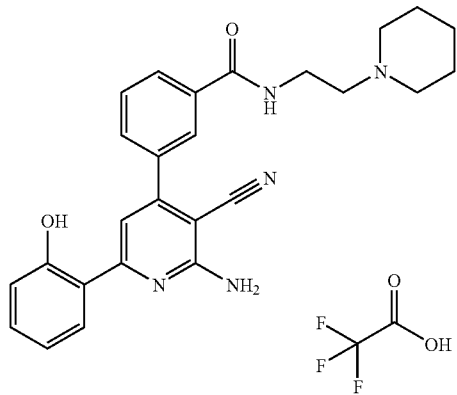

To a cold (0° C.) mixture of 3-(2-amino-3-cyano-6-{2-[(4-methoxybenzyl)oxy]phenyl}-4-pyridinyl)benzoic acid (starting compound 5, 1.35 g, 3.00 mmol), N-(2-aminoethyl)piperidine (0.420 g, 3.30 mmol), and 1-hydroxybenzotriazole (0.490 g, 3.60 mmol) was added 1-ethyl-3-(3-dimethylaminopropyl)carbodiimide hydrochloride (0.69 g, 3.60 mmol) with stirring. The mixture was allowed to warm to room temperature and stirred overnight. The reaction mixture was concentrated under reduced pressure. The residue was dissolved in ethyl acetate and partitioned between ethyl acetate and water. The separated organic phase was washed with brine, dried over $MgSO_4$, filtered and concentrated under reduced pressure. The obtained solid was triturated with ethyl ether and dried under reduced pressure to give 2-(1-piperidinyl)ethyl 3-(2-amino-3-cyano-6-{2-[(4-methoxybenzyl)oxy]phenyl}-4-pyridinyl)benzoate (0.98 g, yield 58%).

A mixture of 2-(1-piperidinyl)ethyl 3-(2-amino-3-cyano-6-{2-[(4-methoxybenzyl)oxy]phenyl}-4-pyridinyl)-benzoate (0.14 g, 0.25 mmol), trifluoroacetic acid (3.00 mL), anisole (0.50 mL) and water (0.50 mL) was stirred at room temperature overnight. The reaction mixture was diluted with toluene and concentrated under reduced pressure. The residue was purified by HPLC (ODS reverse phase column, 10% $CH_3CN/H_2O$-90% $CH_3CN/H_2O$) to give 3-[2-amino-3-cyano-6-(2-hydroxyphenyl)-4-pyridinyl]-N-[2-(1-piperidinyl)ethyl]benzamide trifluoroacetate as a pale yellow solid (0.061 g, yield 44%).

Molecular weight: 555.562

Mass spectrometry: 442

Melting point: 131 dec

In vitro activity grade: C

Cellular activity grade: (A954)-B $^1$H-NMR (300 MHz, DMSO-d6): 1.36-1.86 (6H, m), 2.95 (2H, q, J=10.5 Hz), 3.26-3.28 (2H, m), 3.56 (2H, d, J=12.4 Hz), 3.66 (2H, J=6.6 Hz), 6.88-6.95 (2H, m), 7.01 (1H, t, J=7.91 Hz), 7.45 (1H, s), 7.53 (2H, s), 7.70 (1H, t, J=7.9 Hz), 7.88 (1H, d, J=7.54 Hz), 8.05 (2H, t, J=7.0 Hz), 8.12 (1H, s), 8.84 (1H, t, J=5.7 Hz), 9.02 (1H, br_s), 13.31 (1H, s).

Examples 6-02 to 6-03

In the similar manners as described in Example 6-01 above, compounds in Examples 6-02 and 6-03 as shown in Table 6 were synthesized.

TABLE 6

| EX No | MOLSTRUCTURE | mol weight | MS | A549 | invitro |
|---|---|---|---|---|---|
| 6-02 | | 555,562 | 442 | C | B |
| 6-03 | | 555,562 | 442 | B | A |

Example 7-1

Sodium 2-amino-4-(3-aminophenyl)-6-(2-hydroxyphenyl)nicotinate

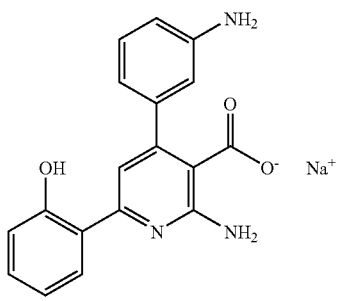

A mixture of tert-butyl 2-amino-4-(3-aminophenyl)-6-(2-hydroxyphenyl)nicotinate (starting compound 6, 0.025 g, 0.066 mmol) and trifluoroacetic acid (1 mL) was stirred at room temperature for 2 hrs. After the mixture was concentrated under reduced pressure, the residue was dissolved in acetonitrile (0.5 mL) and then treated with saturated NaHCO$_3$ solution (0.7 mL). The resulting mixture was purified by HPLC (ODS reverse phase column, 10% CH$_3$CN/H$_2$O-90% CH$_3$CN/H$_2$O) to give Sodium 2-amino-4-(3-aminophenyl)-6-(2-hydroxyphenyl)nicotinate as a pale yellow solid (0.020 g, yield 88%).

Molecular weight: 343.320
Mass spectrometry: 322
Melting point: 140 dec

In vitro activity grade: C
Cellular activity grade: (A954)-D
$^1$H-NMR (300 MHz, DMSO-d6): 4.94 (2H, s), 6.50 (1H, dd, J=1.1, 7.9 Hz), 6.63 (1H, d, J=7.5 Hz), 6.68 (1H, br), 6.73 (2H, s), 6.77-6.83 (2H, m), 6.95 (1H, d, J=7.9 Hz), 6.98 (1H, s), 7.19 (1H, dt, J=1.5, 8.3 Hz), 7.81 (1H, dd, J=1.1, 7.9 Hz), 14.64 (1H, s).

Example 7-2

Sodium 5-({3-[2-amino-3-(aminocarbonyl)-6-(2-hydroxyphenyl)-4-pyridinyl]-phenyl}amino)-4-hydroxy-5-oxopentanoate

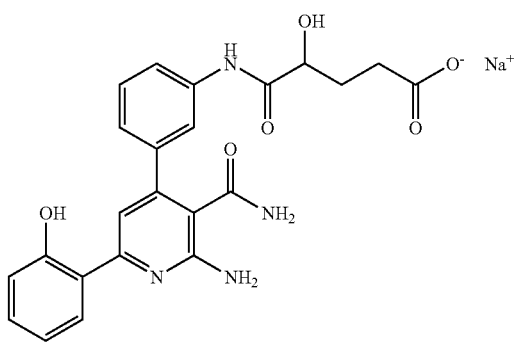

To a cold (0° C.) solution of tert-butyl 2-amino-4-(3-aminophenyl)-6-(2-hydroxyphenyl)nicotinate (starting compound 6, 0.626 g, 1.659 mmol) in THF (7 mL) including pyridine (0.148 mL, 1.824 mmol) was added a solution of 5-oxotetrahydro-2-furancarbonyl chloride (0.271 g, 1.824 mmol) in THF (3 mL). After 1 hr., the mixture was allowed to warm to room temperature and the stirring was continued for 2 hrs. The mixture was partitioned between ethyl acetate and water. The separated organic phase was washed with brine, dried over $Na_2SO_4$, filtered, and concentrated under reduced pressure. The residue was purified by column chromatography on silica-gel (hexane:ethyl acetate, 1:4-1:19) to give tert-butyl 2-amino-6-(2-hydroxyphenyl)-4-(3-{[(5-oxotetrahydro-2-furanyl)carbonyl]amino}-phenyl)-nicotinate as a pale yellow foam (0.677 g, yield 83%).

A mixture of tert-butyl 2-amino-6-(2-hydroxyphenyl)-4-(3-{[(5-oxotetrahydro-2-furanyl)carbonyl]amino}-phenyl)nicotinate (0.025 g, 0.051 mmol) in trifluoroacetic acid (1 mL) was stirred at room temperature for 2 hrs. After the mixture was concentrated under reduced pressure, the residue was dissolved in acetonitrile (0.6 mL) and then treated with saturated $NaHCO_3$ solution (0.2 mL). The resulting mixture was purified by HPLC (ODS reverse phase column, 10% $CH_3CN/H_2O$-90% $CH_3CN/H_2O$) to give sodium 2-amino-6-(2-hydroxyphenyl)-4-(3-{[(5-oxotetrahydro-2-furanyl)carbonyl]amino}phenyl)nicotinate as a pale yellow solid (0.009 g, yield 39%).

To a cold (0° C.) mixture of 2-amino-6-(2-hydroxyphenyl)-4-(3-{[(5-oxotetrahydro-2-furanyl)carbonyl]amino}phenyl)nicotinic acid (0.070 g, 0.15 mmol), ammonium chloride (0.016 g, 0.30 mmol), 1-hydroxybenzotriazole hydrate (0.032 g, 0.24 mmol) in DMF (2 mL) was added 1-ethyl-3-(3-dimethylaminopropyl)carbodiimide hydrochloride (0.034 g, 0.18 mmol) followed by triethylamine (0.042 mL, 0.30 mmol). After 1 hr., the mixture was allowed to warm to room temperature and the stirring was continued overnight. The resulting mixture was diluted with water and extracted with ethyl acetate. The separated organic phase was washed with brine, dried over $Na_2SO_4$, filtered and concentrated under reduced pressure. The residue was purified by HPLC (ODS reverse phase column, 50% $CH_3CN/H_2O$-90% $CH_3CN/H_2O$) to give a carboxamide analog of the starting material. The product was dissolved in acetonitrile (0.7 mL) and then treated with 1N NaOH solution (0.6 mL). The resulting mixture was purified by HPLC (ODS reverse phase column, 10% $CH_3CN/H_2O$-90% $CH_3CN/H_2O$) to give Sodium 5-({3-[2-amino-3-(aminocarbonyl)-6-(2-hydroxyphenyl)-4-pyridinyl]phenyl}amino)-4-hydroxy-5-oxopentanoate as a yellow solid (0.005 g, yield 7%).

Molecular weight: 472.437

Mass spectrometry: 451

Melting point: >260

In vitro activity grade: C

Cellular activity grade: (A954)-C $^1$H-NMR (300 MHz, DMSO-d6): 1.72-1.96 (2H, m), 2.11-2.20 (2H, m), 3.99 (1H, d, J=6.8 Hz), 6.46 (2H, br), 6.82 (2H, br), 7.17 (1H, d, J=7.8 Hz), 7.18 (4H, br), 7.34 (1H, t, J=7.8 Hz), 7.84 (1H, s), 7.87 (1H, d, J=8.0 Hz), 7.95 (1H, dd, J=1.3, 8.0 Hz), 9.75 (1H, s), 10.65 (1H, s), 13.91 (1H, s).

Example 7-3

N-{3-[2-amino-3-(hydroxymethyl)-6-(2-hydroxyphenyl)-4-pyridinyl]phenyl}-3-(1-piperidinyl)propanamide

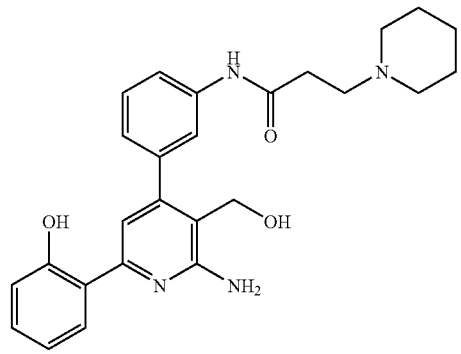

To a cold (0° C.) suspension of lithium aluminum hydride (0.077 g, 1.62 mmol) in THF (3 mL) under an argon atmosphere was added dropwise a solution of tert-butyl 2-amino-4-(3-aminophenyl)-6-(2-hydroxyphenyl)nicotinate (0.353 g, 0.935 mmol) in THF (2 mL) with stirring. After 30 minutes, the mixture was allowed to warm to room temperature, and the stirring was continued at room temperature for 2 hrs. and at 50° C. overnight. After cooled to room temperature, the reaction mixture was quenched with water and extracted with ethyl acetate. The separated organic phase was washed with brine, dried over $Na_2SO_4$, filtered, and concentrated under reduced pressure. The residue was purified by recrystallization from methanol to give 2-[6-amino-4-(3-aminophenyl)-5-(hydroxymethyl)-2-pyridinyl]phenol as a pale yellow solid (0.133 g, yield 45%).

To a cold (0° C.) solution of 2-[6-amino-4-(3-aminophenyl)-5-(hydroxymethyl)-2-pyridinyl]phenol (0.100 g, 0.325 mmol) in THF (3 mL) including pyridine (0.028 mL, 0.34 mmol) was added 3-chloropropionyl chloride (0.043 g, 0.34 mmol). After being stirred for 30 minutes, the mixture was allowed to warm to room temperature and the stirring was continued for 2 hrs. The resulting mixture was diluted with water and extracted with ethyl acetate. The separated organic phase was washed with brine, dried over $Na_2SO_4$, filtered, and concentrated under reduced pressure. The residue was crystallized with ethyl ether. The resulting solid was collected by filtration, washed with ethyl ether, and dried under reduced pressure to give N-{3-[2-amino-3-(hydroxymethyl)-6-(2-hydroxyphenyl)-4-pyridinyl]phenyl}-3-chloropropanamide as a pale yellow solid (0.072 g, yield 56%).

To a solution of N-{3-[2-amino-3-(hydroxymethyl)-6-(2-hydroxyphenyl)-4-pyridinyl]phenyl}-3-chloropropanamide (0.065 g, 0.16 mmol) and sodium iodide (0.007 g, 0.05 mmol) in acetonitrile (5 mL) was added piperidine (0.16 mL, 1.63 mmol), and the mixture was stirred at 75° C. overnight. After cooled to room temperature, the resulting mixture was diluted with water and extracted with ethyl acetate. The separated organic phase was washed with brine, dried over $Na_2SO_4$, filtered and concentrated under reduced pressure. The residue was purified by column chromatography on silica-gel (chloroform:methanol, 85:15) to give N-{3-[2-amino-3-(hydroxymethyl)-6-(2-hydroxyphenyl)-4-pyridinyl]phenyl}-3-(1-piperidinyl)propanamide as a white foam (0.055 g, yield 75%).

Molecular weight: 446.554
Mass spectrometry: 447
Melting point: 133 dec
In vitro activity grade: B
Cellular activity grade: (A954)-B $^1$H-NMR (300 MHz, DMSO-d6): 1.36-1.55 (6H, m), 2.39-2.65 (8H, m), 4.34 (2H, d, J=4.9 Hz), 5.08 (1H, t, J=4.9 Hz), 6.49 (2H, s), 6.78 (1H, dt, J=1.1, 8.3 Hz), 6.85 (1H, dd, J=1.5, 8.67 Hz), 7.10 (1H, s), 7.14 (1H, d, J=7.9 Hz), 7.23 (1H, dt, J=1.5, 8.7 Hz), 7.40 (1H, t, J=7.9 Hz), 7.61 (1H, s), 7.66 (1H, d, J=8.3 Hz), 7.86 (1H, dd, J=1.5, 8.3 Hz), 10.28 (1H, s), 14.22 (1H, s).

Example 8-1

2-[6-amino-4-[4-(ethylamino)-3-hydroxyphenyl]-5-(hydroxymethyl)-2-pyridinyl]-3-(cycloproylmethoxy)phenol hydrochloride

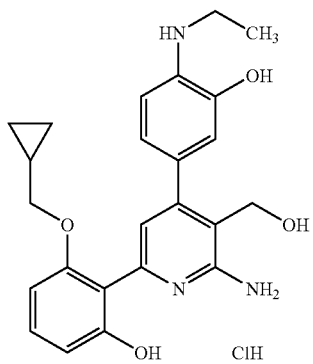

A mixture of 1-{2-(cyclopropylmethoxy)-6-[(4-methoxybenzyl)oxy]phenyl}ethanone (starting compound 1-A' 2.00 g, 6.13 mmol), 3-hydroxy-4-nitrobenzaldehyde (2.05 g, 12.26 mmol), tert-butyl cyanoacetate (1.73 g, 12.26 mmol), ammonium acetate (1.42 g, 18.38 mmol) and 1,2-dimethoxyethane (2.0 mL) was placed in a sealed tube and was stirred at 100° C. for 8 hrs. After being cooled to room temperature, the mixture was concentrated under reduced pressure, and the residue was partitioned between ethyl acetate and water. The separated organic phase was washed with brine, dried over $Na_2SO_4$, filtered, and concentrated under reduced pressure. The residue was purified by flash chromatography on silica gel (hexane:ethyl acetate, 1:1) to give tert-butyl 2-amino-6-{2-(cyclopropylmethoxy)-6-[(4-methoxybenzyl)oxy]phenyl}-4-(3-hydroxy-4-nitrophenyl)nicotinate. (2.32 g, 62%); LC-MS (m/z=614, M+1)

A solution of tert-butyl 2-amino-6-{2-(cyclopropylmethoxy)-6-[(4-methoxybenzyl)oxy]phenyl}-4-(3-hydroxy-4-nitrophenyl)nicotinate (2.32 g, 3.78 mmol) in ethyl acetate (15.0 mL) and THF (15.0 mL) was hydrogenated at 1 atm in the presence of palladium on charcoal (10%, 0.10 g) overnight. The resulting mixture was filtered on Celite and washed with ethyl acetate and THF. The combined filtrate was concentrated under reduced pressure to give tert-butyl 2-amino-4-(4-amino-3-hydroxyphenyl)-6-[2-[(4-methoxybenzyl)oxy-6-(2-methylbutoxy)phenyl]nicotinate. (2.21 g, 100%); LC-MS (m/z=584, M+1)

To a solution of tert-butyl 2-amino-4-(4-amino-3-hydroxyphenyl)-6-[2-[(4-methoxybenzyl)oxy]-6-(2-methylbutoxy)phenyl]nicotinate (2.46 g, 4.21 mmol) was added acetic anhydride (0.44 mL, 4.63 mmol). The mixture was stirred at room temperature for overnight. The mixture was diluted with ethyl acetate and washed with saturated aqueous NaHCO3 and brine. The organic phase was dried over $Na_2SO_4$, filtered and concentrated under reduced pressure to give tert-butyl 4-[4-(acetylamino)-3-hydroxyphenyl]-2-amino-6-{2-(cyclopropylmethoxy)-6-[(4-methoxybenzyl)oxy]phenyl}nicotinate. (2.65 g, 100%); LC-MS (M/z=626, M+1)

To a cold (0° C.) solution of tert-butyl 4-[4-(acetylamino)-3-hydroxyphenyl]-2-amino-6-{2-(cyclopropylmethoxy)-6-[(4-methoxybenzyl)oxy]phenyl}nicotinate (1.00 g, 1.60 mmol) in THF (15.0 mL) under argon atmosphere was added a solution of sodium bis(2-methoxyethoxy)aluminum hydride (3.7 N in toluene, 1.25 mL, 6.39 mmol) in THF (2 mL) dropwise. After being stirred for 5 hrs., a solution of sodium bis(2-methoxyethoxy)aluminum hydride (3.7 N in toluene, 0.833 mL, 4.26 mmol) in THF (1 mL) was added to the mixture at 0° C., then the mixture was allowed to warm to room temperature, and the stirring was continued overnight. The mixture was quenched with ethyl acetate and poured into saturated aqueous sodium potassium tartarate. The extracted organic phase was washed with brine, dried over $Na_2SO_4$, filtered and concentrated under reduced pressure to give 5-[2-amino-6-{2-(cyclopropylmethoxy)-6-[(4-methoxybenzyl)oxy]phenyl}-3-(hydroxymethyl)-4-pyridinyl]-2-(ethylamino)phenol.; LC-MS (m/z=542 M+1)

To a solution of 5-[2-amino-6-{2-(cyclopropylmethoxy)-6-[(4-methoxybenzyl)oxy]phenyl}-3-(hydroxymethyl)-4-pyridinyl]-2-(ethylamino)phenol (0.013 g, 0.023 mmol) in 1,4-dioxane (0.5 mL) was added a solution of HCl in 1,4-dioxane (4N, 1.0 mL). After being stirred overnight, the mixture was diluted with diethyl ether. The resulting precipitate was collected by filtration under argon atmosphere, washed with Et2O, and dried under reduced pressure to give 2-[6-amino-4-[4-(ethylamino)-3-hydroxyphenyl]-5-(hydroxymethyl)-2-pyridinyl]-3-(cyclproylmethoxy)phenol. (0.008 g, 76%); LC-MS (m/z=422 M+1)

Molecular weight: 457.961
Mass spectrometry: 422
Melting point: 232 dec
In vitro activity grade: B
Cellular activity grade: (A954)-

$^1$H-NMR (500 MHz, DMSO-d6): 0.26 (2H, m), 0.47 (2H, m), 1.13 (1H, m), 1.20 (3H, t, J=7.3 Hz), 3.19 (2H, m), 3.57 (1H, s), 3.86 (2H, m), 4.51 (2H, s), 6.64 (2H, m), 6.82 (1H, s), 6.94 (2H, m), 7.28 (2H, m), 10.3 (1H, br), 13.3 (1H, br).

Example 8-2

7-[2-(cyclopropylmethoxy)-6-hydroxyphenyl-5-(3-ethyl-2-oxo-2,3-dihydro-1,3-benzoxazol-6-yl)-1,4-dihydro-2H-pyrido[2,3-d][1,3]oxazin-2-one hydrochloride

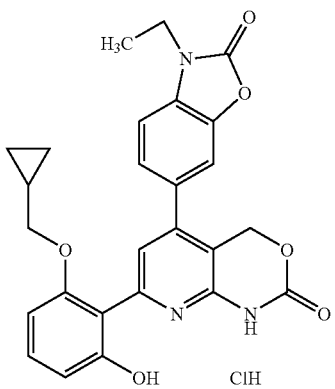

To a cold (0° C.) solution of 5-[2-amino-6-{2-(cyclopropylmethoxy)-6-[(4-methoxybenzyl)oxy]phenyl}-3-(hydroxymethyl)-4-pyridinyl]-2-(ethylamino)phenol (0.150 g, 0.28 mmol) in THF (5.0 mL) including triethylamine (0.12 mL, 0.83 mmol) was added triphosgene (0.099 g, 0.33 mmol). After being stirred for 30 minutes, the mixture was allowed to warm to room temperature, and the stirring was continued overnight. The resulting mixture was quenched with water and extracted with ethyl acetate. The separated organic phase was washed with brine, dried over Na$_2$SO$_4$, filtered and concentrated under reduced pressure. The residue was purified by column chromatography on silica gel (dichloromethane:methanol, 9:1) to give 7-{2-(cyclopropylmethoxy)-6-[(4-methoxybenzyl)oxy]phenyl}-5-(3-ethyl-2-oxo-2,3-dihydro-1,3-benzoxazol-6-yl)-1,4-dihydro-2H-pyrido[2,3-d][1,3]oxazin-2-one. (0.049 g, 30%); LC-MS (m/z=594, M+1)

To a solution of 7-{2-(cyclopropylmethoxy)-6-[(4-methoxybenzyl)oxy]phenyl}-5-(3-ethyl-2-oxo-2,3-dihydro-1,3-benzoxazol-6-yl)-1,4-dihydro-2H-pyrido[2,3-d][1,3]oxazin-2-one (0.036 g, 0.065 mmol) in 1,4-dioxane (1.0 mL) was added a solution of HCl in 1,4-dioxane (4N, 1.0 mL). After being stirred overnight, the mixture was diluted with diethyl ether. The resulting precipitate was collected by filtration under argon atmosphere, washed with Et2O, and dried under reduced pressure to give 7-[2-(cyclopropylmethoxy)-6-(hydroxy)phenyl-5-(3-ethyl-2-oxo-2,3-dihydro-1,3-benzoxazol-6-yl)-1,4-dihydro-2H-pyrido[2,3-d][1,3]oxazin-2-one. (0.025 g, 80%); LC-MS (m/z=436, M+1)

Molecular weight: 509.951

Mass spectrometry: 474

Melting point: 151

In vitro activity grade: C

Cellular activity grade: (A954)-

$^1$H-NMR (500 MHz, DMSO-d6): 0.29 (2H, m), 0.49 (2H, m), 1.20 (1H, m), 1.30 (3H, t, J=7.3 Hz), 3.87 (2H, d, J=6.5 Hz), 3.92 (2H, m), 5.43 (2H, s), 6.55 (2H, d, J=8.2 Hz), 6.92 (0.5 H, d, J=8.5 Hz), 7.19 (1H, t, J=8.2 Hz), 7.33 (2H, m), 7.49 (2H, m), 7.97 (1H, s).

Example 8-3

N-{4-[2-amino-6-[2-(cyclopropylmethoxy)-6-hydroxyphenyl]-3-(hydroxymethyl)-4-pyridinyl]-2-hydroxyphenyl}acetamide hydrochloride

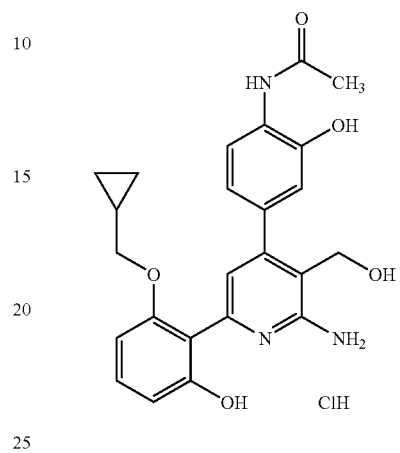

To a cold (0° C.) solution of tert-butyl 4-[4-(acetylamino)-3-hydroxyphenyl]-2-amino-6-{2-(cyclopropylmethoxy)-6-[(4-methoxybenzyl)oxy]phenyl}nicotinate (1.65 g, 2.64 mmol) in THF (25.0 mL) under argon atmosphere was added a solution of sodium bis(2-methoxyethoxy)aluminum hydride (3.7 N in toluene, 4.12 mL, 21.1 mmol) in THF (3 mL) dropwise. After being stirred for 30 minutes, the mixture was quenched with ethyl acetate and poured into saturated aqueous sodium potassium tartarate. The extracted organic phase was washed with brine, dried over Na$_2$SO$_4$, filtered and concentrated under reduced pressure. The residue was purified by column chromatography on silica gel (dichloromethane:methanol, 19:1-9:1) to give N-{4-[2-amino-6-{2-(cyclopropylmethoxy)-6-[(4-methoxybenzyl)oxy]phenyl}-3-(hydroxymethyl)-4-pyridinyl]-2-hydroxyphenyl}acetamide (0.48 g, 33%); LC-MS (m/z=556, M+1).

To a solution of N-{4-[2-amino-6-{2-(cyclopropylmethoxy)-6-[(4-methoxybenzyl)oxy]phenyl}-3-(hydroxymethyl)-4-pyridinyl]-2-hydroxyphenyl}acetamide (0.013 g, 0.023 mmol) in 1,4-dioxane (0.5 mL) was added a solution of HCl in 1,4-dioxane (4N, 1.0 mL). After being stirred overnight, the mixture was diluted with diethyl ether. The resulting precipitate was collected by filtration under argon atmosphere, washed with Et$_2$O, and dried under reduced pressure to give of N-{4-[2-amino-6-[2-(cyclopropylmethoxy)-6-hydroxyphenyl]-3-(hydroxymethyl)-4-pyridinyl]-2-hydroxyphenyl}acetamide. (0.025 g, 80%); LC-MS (m/z=436, M+1)

Molecular weight: 471.945

Mass spectrometry: 436

Melting point: 270 dec

In vitro activity grade: A

Cellular activity grade: (A954)-

$^1$H-NMR (500 MHz, DMSO-d6): 0.27 (2H, m), 0.47 (2H, m), 1.14 (1H, m), 2.14 (3H, s), 3.86 (2H, d, J=7.0 Hz), 4.47 (2H, d, J=11 Hz), 6.64 (2H, dd, J=8.2, 25 Hz), 6.84 (1H, m), 6.94 (1H, m), 7.03 (1H, s), 7.28 (1H, m), 7.56 (1H, br), 7.94 (1H, br), 9.46 (1H, s), 10.2 (1H, br), 13.5 (1H, br).

Examples 8-04 to 8-05

In the similar manners as described in Example 8-01 to 8-03 above, the compounds in Examples 8-04 to 8-05 as shown in Table 8 were synthesized.

TABLE 8

| EX No | STRUCTURE | mol weight | MS | A549 | in-vitro |
|---|---|---|---|---|---|
| 8-04 | 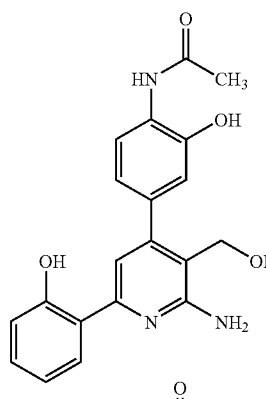 | 365,392 | 366 | A | A |
| 8-05 | 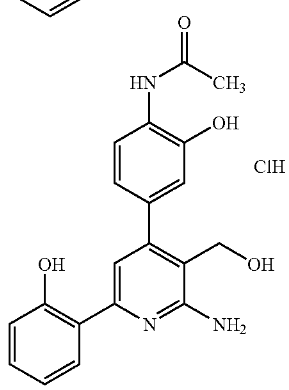 | 401,853 | | B | A |

Example 9

N-{4-[2-amino-3-cyano-6-(2-hydroxyphenyl)-4-pyridinyl]-2-[2-(1-piperidinyl)ethoxy]phenyl}acetamide ditrifluoroacetate

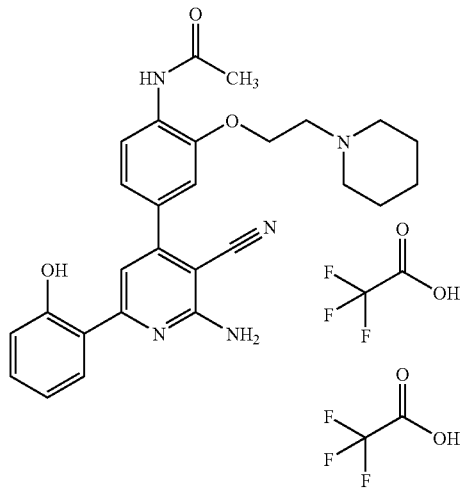

A mixture of 2-[(4-methoxybenzyl)oxy]acetophenone, 3-hydroxy-4-nitrobenzaldehyde, malononitrile, ammonium acetate and toluene was stirred under reflux for 3 hrs. The usual work-up and column chromatography gave 2-amino-4-(3-hydroxy-4-nitrophenyl)-6-{2-[(4-methoxybenzyl)oxy]-phenyl}nicotinonitrile.

A mixture of 2-amino-4-(3-hydroxy-4-nitrophenyl)-6-{2-[(4-methoxybenzyl)oxy]-phenyl}nicotinonitrile, cesium carbonate, potassium iodide and DMF was stirred at 80° C. overnight. The usual work-up and column chromatography gave 2-amino-6-{2-[(4-methoxybenzyl)oxy]phenyl}-4-{4-nitro-3-[2-(1-piperidinyl)ethoxy]-phenyl}nicotinonitrile.

A mixture of 2-amino-6-{2-[(4-methoxybenzyl)-oxy]phenyl}-4-{4-nitro-3-[2-(1-piperidinyl)ethoxy]-phenyl}-nicotinonitrile, SnCl$_2$ and DMF was stirred at room temperature overnight. The usual work-up and column chromatography gave 2-amino-4-{4-amino-3-[2-(1-piperidinyl)ethoxy]phenyl}-6-{2-[(4-methoxybenzyl)oxy]-phenyl}nicotinonitrile.

A mixture of 2-amino-4-{4-amino-3-[2-(1-piperidinyl)ethoxy]phenyl}-6-{2-[(4-methoxybenzyl)oxy]-phenyl}nicotinonitrile, acetyl chloride, pyridine and CH$_2$Cl$_2$ was stirred at 0° C. for 1 hr. and at room temperature for 2 hrs. The usual work-up and column chromatography gave N-{4-(2-amino-3-cyano-6-{2-[(4-methoxybenzyl)oxy]phenyl}-4-pyridinyl)-2-[2-(1-piperidinyl)ethoxy]-phenyl}acetamide.

A mixture of N-{4-(2-amino-3-cyano-6-{2-[(4-methoxybenzyl)oxy]phenyl}-4-pyridinyl)-2-[2-(1-piperidinyl)ethoxy]phenyl}acetamide and trifluoroacetic acid was stirred at room temperature for 3 hrs. Evaporation of trifluoroacetic acid gave N-{4-[2-amino-3-cyano-6-(2-hydroxyphenyl)-4-pyridinyl]-2-[2-(1-piperidinyl)ethoxy]-phenyl}acetamide ditrifluoroacetate.

Molecular weight: 699.612

Mass spectrometry: 472

In vitro activity grade: B

Cellular activity grade: (A954)-B

COMPARATIVE EXAMPLES

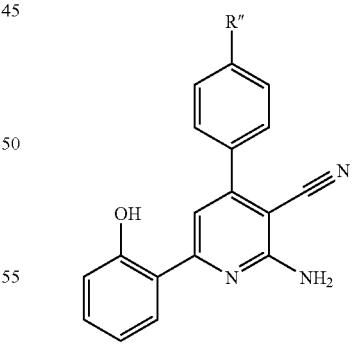

6-(2-Hydroxyphenyl)-4-(R"-phenyl)-3-cyano-2-aminopyridines (wherein R" is nitro or dimethylamino) disclosed in Mannna et al., (Eur. J. Med. Chem. 34 (1999) 245-254) were synthesized according to the methods disclosed in the document. The effects of the synthesized compounds were examined by the in vitro assay method and cellular assay method disclosed herein. These compounds did not show any IKK-beta inhibitory activity and cytokine inhibitory activity.

What is claimed is:

1. A 4-aryl pyridine derivative of the formula (I):

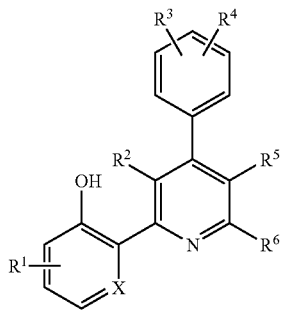

wherein

X is CH;

$R^1$ is hydrogen, hydroxy, halogen, $C_{1-6}$ alkyl, $C_{1-6}$ alkoxy, $C_{1-6}$ alkoxycarbonyl, nitro, amino, mono or di ($C_{1-6}$ alkyl)amino, phenylsulfonylamino, —$NHR^{11}$ or —O—$(CH_2)_n$—$R^{12}$, wherein $R^{11}$ is phenyl substituted $C_{1-6}$ alkyl, $C_{1-6}$ alkanoyl or $C_{1-6}$alkylsulfonyl, n represents an integer selected from 0 to 6, and $R^{12}$ is $C_{2-6}$ alkenyl, benzoyl, mono or di phenyl, mono or di ($C_{1-6}$ alkyl)-amino, $C_{1-6}$ alkanoyl, $C_{1-6}$ alkoxycarbonyl, or a 3 to 10 membered saturated or unsaturated ring having 0 to 3 heteroatoms selected from the group consisting of S, O and N, and said ring is optionally substituted by hydroxy, nitro, cyano, mono or di halogen, $C_{1-6}$ alkyl, halogen substituted $C_{1-6}$ alkyl, amino, mono or di ($C_{1-6}$ alkyl)amino, $C_{1-6}$ alkanoylamino, carbamoyl, $C_{1-6}$ alkoxy, $C_{1-6}$ alkoxycarbonyl, or phenyl;

$R^2$ is hydrogen, hydroxy, halogen, or $C_{1-6}$ alkyl;

$R^3$ is hydrogen, hydroxy, halogen, $C_{1-6}$ alkoxy, $C_{3-6}$ cycloalkyl substituted $C_{1-6}$ alkyloxy, —$NR^{31}R^{32}$, or a 3 to 6 membered saturated ring having 0 to 3 heteroatoms selected from the group consisting of O and N, and said ring is optionally substituted by $R^{33}$;

wherein $R^{31}$ is hydrogen or $C_{1-6}$ alkyl $R^{32}$ is hydrogen, $C_{1-6}$ alkanoyl, or $C_{1-6}$ alkyl optionally substituted by hydroxy or phenyl, $R^{33}$ is nitro, cyano, $C_{1-6}$ alkyl optionally substituted by hydroxy or amino, $C_{1-6}$ alkoxy, hydroxy substituted $C_{1-6}$ alkyloxy, amino substituted $C_{1-6}$ alkyloxy, $C_{1-6}$ alkanoyl, carbamoyl or —$NR^{33a}R^{33b}$ wherein $R^{33a}$ is hydrogen or $C_{1-6}$ alkyl $R^{33b}$ is hydrogen, $C_{1-6}$ alkyl optionally substituted by hydroxy or phenyl, $C_{1-6}$ alkanoyl, $C_{1-6}$ alkylsulfonyl, or trifluoroacetyl, $R^4$ is —NH—$COR^{41}$, wherein $R^{41}$ is $C_{1-6}$ alkyl optionally substituted by $R^{41a}$, $C_{1-6}$ alkoxy, oxotetrahydrofuryl, oxopyrrolidinyl, —CH(OH)$R^{41b}$, —CH($NH_2$)$R^{41c}$, —$NHR^{41c}$, or piperazino optionally substituted by $R^{41d}$, wherein $R^{41a}$ is carboxy, $C_{1-6}$ alkoxy, —CH($NH_2$)carboxy, —$NR^{41a-1}R^{41a-2}$, or a 3 to 10 membered saturated ring having 0 to 3 heteroatoms selected from the group consisting of O and N, and said ring is optionally substituted by carboxy, $C_{1-6}$ alkyl optionally substituted by hydroxy or benzodioxane, $C_{3-6}$ cycloalkyl, $C_{1-6}$ alkanoyl, carboxy, benzyl, $C_{1-6}$ alkoxycarbonyl, or furoyl, wherein $R^{41a-1}$ is hydrogen or $C_{1-6}$ alkyl optionally substituted by hydroxy, $C_{1-6}$ alkyloxy, $C_{3-8}$ cycloalkyl, or piperidino, $R^{41a-2}$ is hydrogen or $C_{1-6}$ alkyl optionally substituted by hydroxy, $C_{1-6}$ alkyloxy or $C_{3-6}$ cycloalkyl, $C_{1-6}$ alkoxy or a 3 to 6 membered saturated ring having 0 to 3 heteroatoms selected from the group consisting of O and N, and said ring is optionally substituted by carboxy, $C_{1-6}$ alkyl, $C_{1-6}$ alkanoyl, or $C_{1-6}$ alkyloxy, $R^{41b}$ is $C_{1-6}$ alkyl optionally substituted by carboxy or $C_{1-6}$ alkyloxy, $C_{1-6}$ alkoxy, or $C_{1-6}$ alkoxycarbonyl, $R^{41c}$ is carboxy, $C_{1-6}$ alkyl optionally substituted by carboxy or a 3 to 6 membered saturated ring having 0 to 3 heteroatoms selected from the group consisting of O and N, or $R^{41d}$ is $C_{1-6}$ alkyl optionally substituted by carboxy or $C_{1-6}$ alkyloxy, or $C_{1-6}$ alkoxy $R^{42}$ is $C_{1-6}$ alkoxy, carboxy, amino, —CH($NH_2$)-carboxy or a 5 to 7 membered saturated or unsaturated ring having 0 to 3 heteroatoms selected from the group consisting of O and N, and said ring is optionally substituted by hydroxy, nitro, mono or di halogen, $C_{1-6}$ alkyl, halogen substituted $C_{1-6}$ alkyl, amino, mono or di ($C_{1-6}$ alkyl)amino, or carbamoyl;

$R^{43}$ is carboxy, amino, —CH($NH_2$)-carboxy or a 5 to 7 membered saturated or unsaturated ring having 0 to 3 heteroatoms selected from the group consisting of O and N, and said ring is optionally substituted by hydroxy, nitro, mono or di halogen, $C_{1-6}$ alkyl, halogen substituted $C_{1-6}$ alkyl, amino, mono or di ($C_{1-6}$ alkyl)amino, or carbamoyl;

or $R^3$ and $R^4$ may form, together with the carbon atoms in the benzene ring, a 4 to 6 membered saturated ring having 0 to 3 heteroatoms selected from the group consisting of O and N, and said ring is optionally substituted by one or more substituents selected from the group consisting of hydroxy, nitro, mono or di halogen, $C_{1-6}$ alkyl, halogen substituted $C_{1-6}$ alkyl, oxo, amino, mono or di ($C_{1-6}$ alkyl)amino, and carbamoyl;

$R^5$ is hydrogen, cyano, carboxy, carbamoyl, $C_{1-6}$ alkyl optionally substituted by hydroxy or carbamoyl, and $C_{1-6}$ alkoxycarbonyl, and $R^6$ is amino or acetamido or $R^5$ and $R^6$ may form, together with the carbon atoms in the pyridine ring, a 5 to 7 membered saturated or unsaturated ring having 0 to 3 heteroatoms selected from the group consisting of O, S and N, and said ring optionally having substituents selected from the group consisting of halogen, nitro, cyano, oxo, thioxo, $C_{1-6}$ alkyl, $C_{1-6}$ alkylsulfonyl, $C_{1-6}$ alkoxy, $C_{1-6}$ alkoxycarbonyl, phenyl, $C_{1-6}$ alkanoyl, amino, $C_{1-6}$ alkylamino, $C_{1-6}$ alkanoylamino, carbamoyl, $C_{3-8}$ cycloalkylaminocarbonyl, $C_{1-6}$ alkylaminocarbonyl, halogen substituted $C_{1-6}$ alkylaminocarbonyl, di ($C_{1-6}$ alkyl)aminocarbonyl, benzoylamino, phenylsulfonyl, di($C_{1-6}$ alkyl)amino$C_{1-6}$ alkylaminocarbonyl, hydroindenylaminocarbonyl, diphenylmethylaminocarbonyl, pyrrolidinocarbonyl, $C_{1-6}$ alkyloxy $C_{1-6}$ alkyl amino carbonyl, morpholinocarbonyl, piperazinocarbonyl, phenyl$C_{1-6}$ alkylaminocarbonyl, carboxy$C_{1-6}$ alkylaminocarbonyl, $C_{3-8}$ cycloalkyl$C_{1-6}$ alkylaminocarbonyl, hydroxy $C_{1-6}$alkylaminocarbonyl, and methylsulfonylaminocarbonyl
or a salt thereof.

2. The compound or a salt thereof as claimed in claim 1, wherein

X is CH;

$R^1$ is hydrogen, halogen, $C_{1-6}$ alkyl, $C_{1-6}$ alkoxy or $C_{3-6}$ cycloalkyl substituted $C_{1-6}$ alkyloxy;

$R^2$ is hydrogen or halogen;

$R^3$ is hydrogen, hydroxy, halogen, $C_{1-6}$ alkoxy, $C_{3-6}$ cycloalkyl substituted $C_{1-6}$alkyloxy, amino, mono or di($C_{1-6}$ alkyl)amino, $C_{1-6}$ alkanoylamino, $C_{1-6}$ alkyl(hydroxy substituted $C_{1-6}$ alkyl)amino, $C_{1-6}$ alkyl(benzyl)amino, morpholino, piperidino, or pyrrolidino optionally substituted by $C_{1-6}$ alkyl, $C_{1-6}$ alkyloxy or hydroxy substituted $C_{1-6}$ alkyl, amino, di($C_{1-6}$ alkyl)amino, or trifluoroacetylamino;

$R^4$ is —NH—$COR^{41}$,
wherein
$R^{41}$ is $C_{1-6}$ alkyl optionally substituted by $R^{41a}$, $C_{1-6}$ alkoxy, $C_{1-6}$ alkyloxy substituted $C_{1-6}$ alkyl, oxotetrahydrofuryl, oxopyrrolidinyl, —CH(OH)$R^{41b}$, —CH(NH$_2$)$R^{41c}$, or —NHR$^{41c}$,
wherein
$R^{41a}$ is $C_{1-6}$ alkoxy, carboxy, —NHR$^{41a-1}$ (wherein $R^{41a-1}$ is hydrogen, or $C_{1-6}$ alkyl optionally substituted by hydroxy, $C_{1-6}$ alkyloxy, $C_{3-8}$ cycloalkyl, or piperidino), —CH(NH$_2$)—N($C_{1-6}$ alkyl)$R^{41a-2}$ (wherein $R^{41a-2}$ is $C_{1-6}$ alkyl or $C_{1-6}$ alkyl substituted pyrrolidinyl), pyrrolidinyl, piperidino optionally substituted by carboxy or $C_{1-6}$ alkoxycarbonyl, piperidino optionally fused with $C_{3-6}$ cycloalkyl, or piperazino optionally substituted by $C_{1-6}$ alkyl, hydroxy substituted $C_{1-6}$ alkyl, benzodioxane substituted $C_{1-6}$ alkyl, $C_{1-6}$ alkanoyl, $C_{3-6}$ cycloalkyl, benzyl, or furoyl,
$R^{41b}$ is $C_{1-6}$ alkyl optionally substituted by carboxy, or $C_{1-6}$ alkoxycarbonyl,
$R^{41c}$ is $C_{1-6}$ alkyl optionally substituted by carboxy or piperidino, or $R^3$ and $R^4$ may form, together with the carbon atoms in the benzene ring, a 5 membered saturated ring having 0 to 2 heteroatoms selected from the group consisting of O and N, and said ring is optionally substituted by $C_{1-6}$ alkyl, or oxo;

$R^5$ is hydrogen, carbamoyl, cyano, carboxy, $C_{1-6}$ alkoxycarbonyl, or hydroxy substituted $C_{1-6}$ alkyl; and $R^6$ is amino or $C_{1-6}$ alkanoylamino, or $R^5$ and $R^6$ may form, together with the carbon atoms in the pyridine ring, a 6 membered saturated or unsaturated ring having 0 to 3 heteroatoms selected from the group consisting of O, S and N, and said ring optionally having substituents selected from the group consisting of halogen, nitro, cyano, oxo, thioxo, $C_{1-6}$ alkyl, $C_{1-6}$ alkylsulfonyl, $C_{1-6}$ alkoxy, $C_{1-6}$ alkoxycarbonyl, phenyl, $C_{1-6}$ alkanoyl, amino, $C_{1-6}$ alkylamino, $C_{1-6}$ alkanoylamino, carbamoyl, $C_{3-8}$ cycloalkylaminocarbonyl, $C_{1-6}$ alkylaminocarbonyl, halogen substituted $C_{1-6}$ alkylaminocarbonyl, and di ($C_{1-6}$ alkyl)aminocarbonyl
or a salt thereof.

3. The compound or a salt thereof as claimed in claim 1, wherein

X is CH;

$R^1$ is hydrogen, halogen, $C_{1-6}$ alkoxy, or cyclopropyl methoxy;

$R^2$ is hydrogen;

$R^3$ is hydrogen, hydroxy, halogen, amino, mono or di($C_{1-6}$ alkyl)amino, acetamido, $C_{1-6}$alkoxy, cyclopropyl methoxy, $C_{1-6}$ alkyl(hydroxy substituted $C_{1-6}$ alkyl)amino, $C_{1-6}$ alkyl(benzyl)amino, morpholino, piperidino, or pyrrolidino optionally substituted by $C_{1-6}$ alkyl, hydroxy substituted $C_{1-6}$ alkyl, amino, di ($C_{1-6}$ alkyl)amino, or trifluoroacetylamino;

$R^4$ is —NH—$COR^{41}$,
wherein
$R^{41}$ is $C_{1-6}$ alkyl optionally substituted by $R^{41a}$, $C_{1-6}$ alkoxy, oxotetrahydrofuryl, oxopyrrolidinyl, —CH(OH)$R^{41b}$, or —CH(NH$_2$)$R^{41c}$,
wherein
$R^{41a}$ is $C_{1-6}$ alkoxy, carboxy, —CH(NH$_2$)-carboxy, —NHR$^{41a-1}$ (wherein $R^{41a-1}$ is hydrogen, $C_{1-6}$ alkyl optionally substituted by hydroxy, $C_{3-8}$ cycloalkyl, $C_{1-6}$ alkoxy, or piperidino), —N($C_{1-6}$ alkyl)$R^{41a-2}$ (wherein $R^{41a-2}$ is $C_{1-6}$ alkyl or $C_{1-6}$ alkyl substituted pyrrolidinyl), pyrrolidinyl, piperidino optionally substituted by carboxy or $C_{1-6}$ alkoxycarbonyl, piperidino fused with cyclohexane, or piperazino optionally substituted by $C_{1-6}$ alkyl, hydroxy substituted $C_{1-6}$ alkyl, benzodioxane substituted $C_{1-6}$ alkyl, benzyl, $C_{1-6}$ alkanoyl, cyclohexyl, or furoyl,
$R^{41b}$ is $C_{1-6}$ alkyl optionally substituted by carboxy or $C_{1-6}$ alkoxycarbonyl,
$R^{41c}$ is $C_{1-6}$ alkyl optionally substituted by carboxy, or $R^3$ and $R^4$ may form —NR$^{401}$—CO—O-(wherein $R^{401}$ is hydrogen or $C_{1-6}$ alkyl);

$R^5$ is hydrogen, carbamoyl, cyano, carboxy, or hydroxymethyl; and $R^6$ is amino or acetamido or $R^5$ and $R^6$ may form —$R^{50}$—CH$_2$—NH—, —$R^{50}$—CO—NH—, —$R^{50}$—SO$_2$—NH—, or —$R^{50}$—C(=S)—NH—
wherein
$R^{50}$ is —CHR$^{501}$—O—, —CH$_2$—N R$^{501}$—, —CO—NR$^{501}$—, (wherein R$^{501}$ is hydrogen, $C_{1-6}$ alkyl, $C_{1-6}$ alkanoyl, $C_{1-6}$ alkoxycarbonyl, carbamoyl, $C_{1-6}$ alkylsulfonyl, $C_{3-8}$ cycloalkylaminocarbonyl, $C_{1-6}$ alkylaminocarbonyl, di ($C_{1-6}$ alkyl)aminocarbonyl or phenyl)
or a salt thereof.

4. The compound as claimed in claim 1 selected from the group consisting of:

5-({3-[2-amino-3-cyano-6-(2-hydroxyphenyl)-4-pyridinyl]phenyl}amino)-4-hydroxy-5-oxopentanoate;

N-{3-[2-amino-3-cyano-6-(2-hydroxyphenyl)-4-pyridinyl]phenyl}-5-oxotetrahydro-2-furancarboxamide;

N$^4$-{3-[2-amino-3-cyano-6-(2-hydroxyphenyl)-4-pyridinyl]phenyl}-L-asparagine;

N$^1$-{3-[2-amino-3-cyano-6-(2-hydroxyphenyl)-4-pyridinyl]phenyl}-L-asparagine;

N-{3-[2-amino-3-cyano-6-(2-hydroxyphenyl)-4-pyridinyl]phenyl}-3-(1-piperidinyl)propanamide;

5-({4-[2-amino-3-cyano-6-(2-hydroxyphenyl)-4-pyridinyl]phenyl}amino)-4-hydroxy-5-oxopentanoate;

5-({5-[2-amino-3-cyano-6-(2-hydroxyphenyl)-4-pyridinyl]-2-chlorophenyl}amino)-4-hydroxy-5-oxopentanoate;

N-{3-[2-amino-3-cyano-6-(2-hydroxyphenyl)-4-pyridinyl]phenyl}-2-[4-(2-furoyl)-1-piperazinyl]acetamide;

N-{3-[2-amino-3-cyano-6-(2-hydroxyphenyl)-4-pyridinyl]phenyl}-3-(4-ethyl-1-piperazinyl)propanamide;

N-{3-[2-amino-3-cyano-6-(2-hydroxyphenyl)-4-pyridinyl]phenyl}-3-octahydro-1(2H)-quinolinylpropanamide;

$N^1$-{3-[2-amino-3-cyano-6-(2-hydroxyphenyl)-4-pyridinyl]phenyl}-$N^2$-cyclopentylglycinamide;

$N^1$-{3-[2-amino-3-cyano-6-(2-hydroxyphenyl)-4-pyridinyl]phenyl}-$N^2$-(cyclopropylmethyl)glycinamide;

$N^1$-{3-[2-amino-3-cyano-6-(2-hydroxyphenyl)-4-pyridinyl]phenyl}-$N^2$-propylglycinamide;

$N^1$-{3-[2-amino-3-cyano-6-(2-hydroxyphenyl)-4-pyridinyl]phenyl}-$N^2$-(3-hydroxypropyl)glycinamide;

$N^1$-{3-[2-amino-3-cyano-6-(2-hydroxyphenyl)-4-pyridinyl]phenyl}-$N^3$-(cyclopropylmethyl)-β-alaninamide;

$N^1$-{3-[2-amino-3-cyano-6-(2-hydroxyphenyl)-4-pyridinyl]phenyl}-$N^2$,$N^2$-dimethylglycinamide;

N-{3-[2-amino-3-cyano-6-(2-hydroxyphenyl)-4-pyridinyl]phenyl}-2-(1-pyrrolidinyl)acetamide;

$N^1$-{3-[2-amino-3-cyano-6-(2-hydroxyphenyl)-4-pyridinyl]phenyl}-$N^2$-[2(methyloxy)ethyl]glycinamide;

$N^1$-[5-[2-amino-3-cyano-6-(2-hydroxyphenyl)-4-pyridinyl]-2-(3-amino-1-pyrrolidinyl)phenyl]-β-alaninamide;

$N^1$-[5-[2-amino-3-cyano-6-(2-hydroxyphenyl)-4-pyridinyl]-2-(1-piperidinyl)phenyl]-β-alaninamide;

$N^1$-[5-[2-amino-3-cyano-6-(2-hydroxyphenyl)-4-pyridinyl]-4-pyridinyl]-2-(1-pyrrolidinyl)phenyl]-β-alaninamide;

$N^1$-{5-[2-amino-3-cyano-6-(2-hydroxyphenyl)-4-pyridinyl]-2-[ethyl(2-hydroxyethyl)amino]phenyl}-β-alaninamide;

$N^1$-[5-[2-amino-3-cyano-6-(2-hydroxyphenyl)-4-pyridinyl]-2-(4-morpholinyl)phenyl]-β-alaninamide;

$N^1$-[5-[2-amino-3-cyano-6-(2-hydroxyphenyl)-4-pyridinyl]-2-(dimethylamino)phenyl]-β-alaninamide;

N-{3-[2-amino-3-cyano-6-(2-hydroxyphenyl)-4-pyridinyl]-4-chlorophenyl}-3-(1-piperidinyl)propanamide;

$N^1$-{5-[2-amino-3-cyano-6-(2-hydroxyphenyl)-4-pyridinyl]-2-chlorophenyl}-$N^2$-(cyclopropylmethyl)glycinamide;

$N^1$-{5-[2-amino-3-cyano-6-(2-hydroxyphenyl)-4-pyridinyl]-2-chlorophenyl}-$N^2$-(2-methoxyethyl)glycinamide;

$N^1$-{5-[2-amino-3-cyano-6-(2-hydroxyphenyl)-4-pyridinyl]-2-chlorophenyl}-β-alaninamide;

N-{4-[2-amino-3-cyano-6-(2-hydroxyphenyl)-4-pyridinyl]-2-hydroxyphenyl}acetamide;

N-{5-[2-amino-3-cyano-6-(2-hydroxyphenyl)-4-pyridinyl]-2-chlorophenyl}-3-(1-piperidinyl)propanamide;

$N^1$-[5-[2-amino-3-cyano-6-(2-hydroxyphenyl)-4-pyridinyl]-2-(dimethylamino)phenyl]-$N^2$-(cyclopropylmethyl)glycinamide;

N-[5-[2-amino-3-cyano-6-(2-hydroxyphenyl)-4-pyridinyl]-2-(dimethylamino)phenyl]-3-(1-piperidinyl)propanamide;

$N^1$-{5-[2-amino-3-cyano-6-(2-hydroxyphenyl)-4-pyridinyl]-2-[(2S)-2-(hydroxymethyl)-1-pyrrolidinyl]phenyl}-L-leucinamide;

$N^1$-{5-[2-amino-3-cyano-6-(2-hydroxyphenyl)-4-pyridinyl]-2-[(3S)-3-(dimethylamino)-1-pyrrolidinyl]phenyl}-$N^2$-(cyclopropylmethyl)glycinamide;

$N^1$-(5-[2-amino-3-cyano-6-(2-hydroxyphenyl)-4-pyridinyl]-2-{3-[(trifluoroacetyl)amino]-1-pyrrolidinyl}phenyl)-L-leucinamide;

N-(5-[2-amino-3-cyano-6-(2-hydroxyphenyl)-4-pyridinyl]-2-{3-[(trifluoroacetyl)amino]-1-pyrrolidinyl}phenyl)-3-(1-piperidinyl)propanamide;

$N^1$-(5-[2-amino-3-cyano-6-(2-hydroxyphenyl)-4-pyridinyl]-2-{3-[(trifluoroacetyl)amino]-1-pyrrolidinyl}phenyl)-$N^2$-(2-methoxyethyl)glycinamide;

$N^1$-(5-[2-amino-3-cyano-6-(2-hydroxyphenyl)-4-pyridinyl]-2-{3-[(trifluoroacetyl)amino]-1-pyrrolidinyl}phenyl)-$N^2$-(cyclopropylmethyl)glycinamide;

N-{4-[2-amino-3-cyano-6-(2-hydroxyphenyl)-4-pyridinyl]-2-[2-(1-piperidinyl)ethoxy]phenyl}acetamide;

N-{4-[2-amino-3-(hydroxymethyl)-6-(2-hydroxyphenyl)-4-pyridinyl]-2-hydroxyphenyl}acetamide;

N-{4-[2-amino-6-[2-(cyclopropylmethoxy)-6-hydroxyphenyl]-3-(hydroxymethyl)-4-pyridinyl]-2-hydroxyphenyl}acetamide; and 7-[2-(cyclopropylmethoxy)-6-hydroxyphenyl]-5-(3-ethyl-2-oxo-2,3-dihydro-1,3-benzoxazol-6-yl)-1,4-dihydro-2H-pyrido[2,3-d][1,3]oxazin-2-one.

5. A pharmaceutical composition comprising the compound or a salt thereof as claimed in claim 1 as an active ingredient.

6. A pharmaceutical composition comprising the compound or a salt thereof as claimed in claim 1 together with one or more pharmaceutically acceptable excipients.

7. A method of treating an inflammatory disease in a subject comprising administering to a subject in need thereof, a therapeutically effective amount of one or more compounds of claim 1, wherein the disease is asthma, allergic rhinitis, atopic dermatitis, hives, conjunctivitis, vernal catarrh, chronic arthrorheumatism, systemic lupus erythematosus, psoriasis, diabrotic colitis, systemic inflammatory response syndrome, sepsis, polymyositis, dermatomyositis, polyarthritis nodosa, mixed connective tissue disease, Sjoegren's syndrome, or gout.

8. A method of treating ischemia in a subject comprising administering to a subject in need thereof, a therapeutically effective amount of one or more compounds of claim 1.

9. A method of treating a tumor in a subject comprising administering to a subject in need thereof, a therapeutically effective amount of one or more compounds of claim 1, wherein the tumor is a colorectal cancer tumor.

* * * * *